US009822052B2

(12) United States Patent
Levy et al.

(10) Patent No.: US 9,822,052 B2
(45) Date of Patent: Nov. 21, 2017

(54) NANOPARTICLE CATALYSTS FOR CONVERSION OF CYCLOHEXANOL TO CYCLOHEXANONE

(71) Applicants: AdvanSix Resins & Chemicals LLC, Parsippany, NJ (US); University of Southampton, Southampton (GB)

(72) Inventors: Alan B. Levy, Randolph, NJ (US); Scott R. Keenan, Marlton, NJ (US); Robert Raja, Fair Oak (GB); Arran M. Gill, Guiseley (GB); Matthew E. Potter, Leigh (GB); Sivan A. Van Aswegen, Tunbridge Wells (GB)

(73) Assignees: ADVANSIX RESINS & CHEMICALS LLC, Parsippany, NJ (US); UNIVERSITY OF SOUTHAMPTON, Southampton (GB)

(*) Notice: Subject to any disclaimer, the term of this patent is extended or adjusted under 35 U.S.C. 154(b) by 0 days.

(21) Appl. No.: 15/279,837

(22) Filed: Sep. 29, 2016

(65) Prior Publication Data
US 2017/0096380 A1    Apr. 6, 2017

Related U.S. Application Data

(60) Provisional application No. 62/235,684, filed on Oct. 1, 2015.

(51) Int. Cl.
| | |
|---|---|
| *C07C 45/35* | (2006.01) |
| *B01J 27/00* | (2006.01) |
| *B01J 37/00* | (2006.01) |
| *C07C 45/39* | (2006.01) |
| *B01J 27/13* | (2006.01) |
| *B01J 27/185* | (2006.01) |
| *B01J 37/04* | (2006.01) |
| *B01J 37/08* | (2006.01) |

(52) U.S. Cl.
CPC .............. *C07C 45/39* (2013.01); *B01J 27/13* (2013.01); *B01J 27/1856* (2013.01); *B01J 37/04* (2013.01); *B01J 37/088* (2013.01); *C07C 2601/14* (2017.05)

(58) Field of Classification Search
CPC ....... C07C 45/39; B01J 27/13; B01J 27/1856; B01J 37/04
USPC .......................................................... 568/360
See application file for complete search history.

(56) References Cited

U.S. PATENT DOCUMENTS

| 6,344,586 B1 | 2/2002 | Ichihashi et al. |
| 6,703,529 B1 | 3/2004 | Fodor et al. |
| 7,081,552 B2 | 7/2006 | Pirutko et al. |
| 2014/0275627 A1 | 9/2014 | Kweeder et al. |
| 2015/0141239 A1 | 5/2015 | Lin et al. |

FOREIGN PATENT DOCUMENTS

| CN | 101041615 A | 9/2007 |
| CN | 104478701 A | 4/2015 |
| KR | 100613309 B1 | 8/2006 |

OTHER PUBLICATIONS

Hinde et al. Probing the origin of in situ generated nanoparticles as sustainable oxidation catalysts. Dalton Transactions, 2013, vol. 42, 12600-12605.*
Williams et al. Complex anion inclusion compounds: flexible anion-exchange materials. Chemical Communications, 2013, vol. 49, 249-251.*
Beier, Matthias J., et al. "Selective Liquid-Phase Oxidation of Alcohols Catalyzed by a Silver-Based Catalyst Promoted by the Presence of Ceria." Journal of Catalysis: 266:320-330, 2009.
Fukuda, Osamu, et al. "A New Strategy for Catalytic Baeyer-Villiger Oxidation of KA-Oil With Molecular Oxygen Using N-Hydroxyphthalimide." Tetrahedron Letters, 42:3479-3481.
Li, Zhengrong and Wang, Tao. "Oxidation of Cyclohexanone and Cyclohexanol to Adipic Acid Using Hydrogen Peroxide and Supercritical Carbon Dioxide." State Key Lab of Chemical Engineering, Department of Chemical Engineering, Tsinghua University, Beijing 100084, China. Reference was first posted online Jan. 6, 2012: https://web.archive.org/web/20120101000000*/http://www.isasf.net/fileadmin/files/Docs/Arcachon/oraux/c21-CO27%20Wang.pdf, 3 pages.

* cited by examiner

*Primary Examiner* — Sikarl Witherspoon
(74) *Attorney, Agent, or Firm* — Faegre Baker Daniels LLC

(57) ABSTRACT

Methods for converting an alcohol, such as cyclohexanol to a ketone, such as cyclohexanone, include reacting the alcohol in the presence of a catalyst and oxygen to produce the ketone. In one exemplary embodiment, the catalyst comprises a microporous copper chloropyrophosphate framework including a plurality of noble metal nanoparticles. In one exemplary embodiment, the noble metal nanoparticles include at least one metal selected from the group consisting of platinum, palladium, and gold.

12 Claims, 52 Drawing Sheets

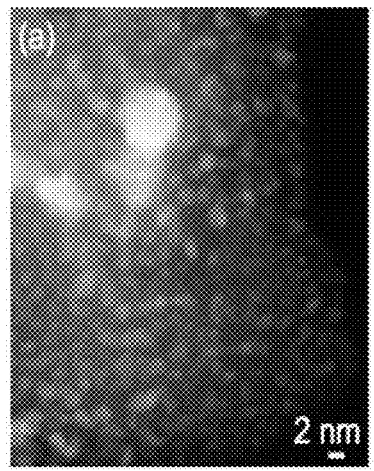 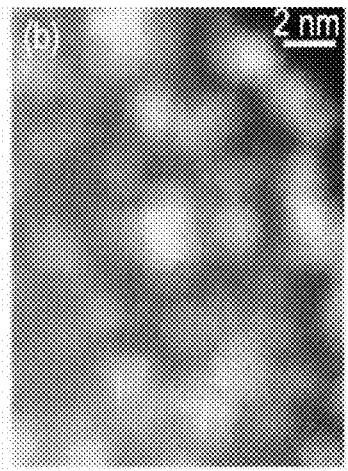 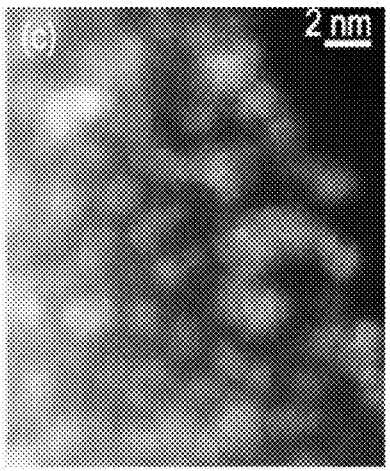
FIG. 13A          FIG. 13B          FIG. 13C
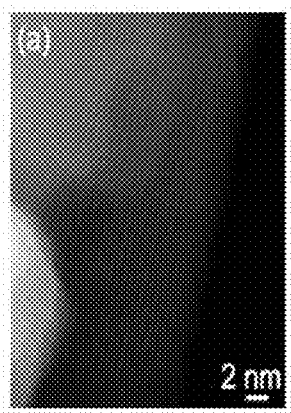 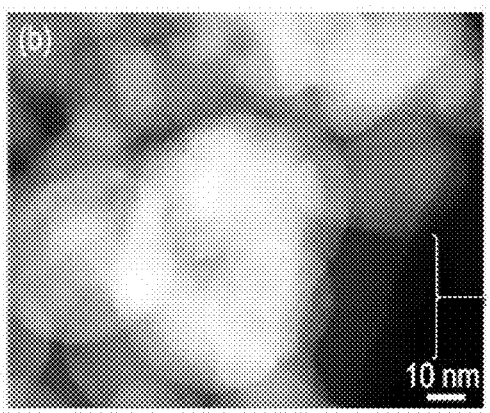 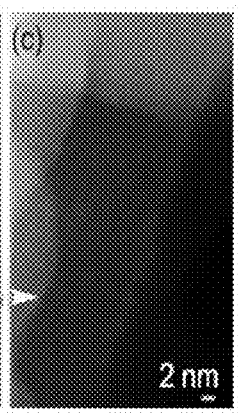
FIG. 14A          FIG. 14B          FIG. 14C

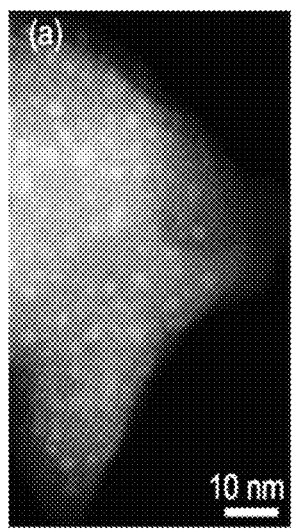 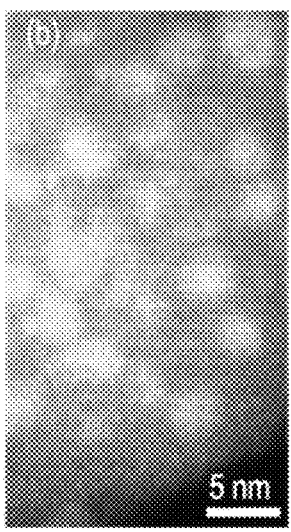 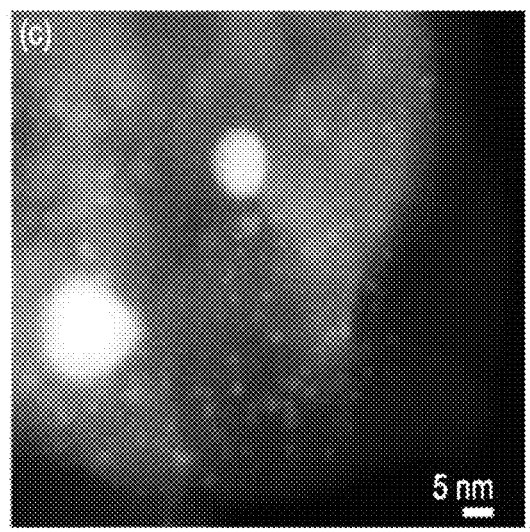
*FIG. 15A*  *FIG. 15B*  *FIG. 15C*

Reduced at 200° C    Reduced at 250° C    Reduced at 300° C    Reduced at 350° C

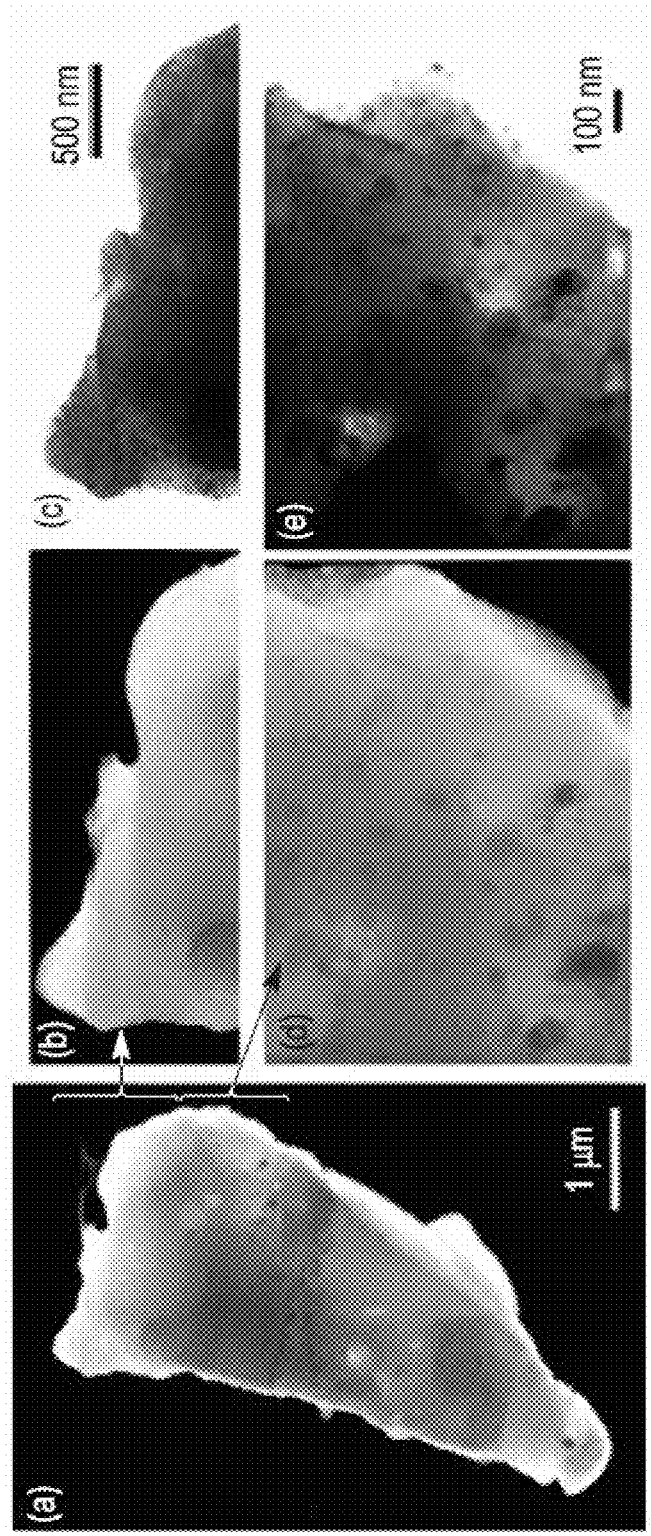

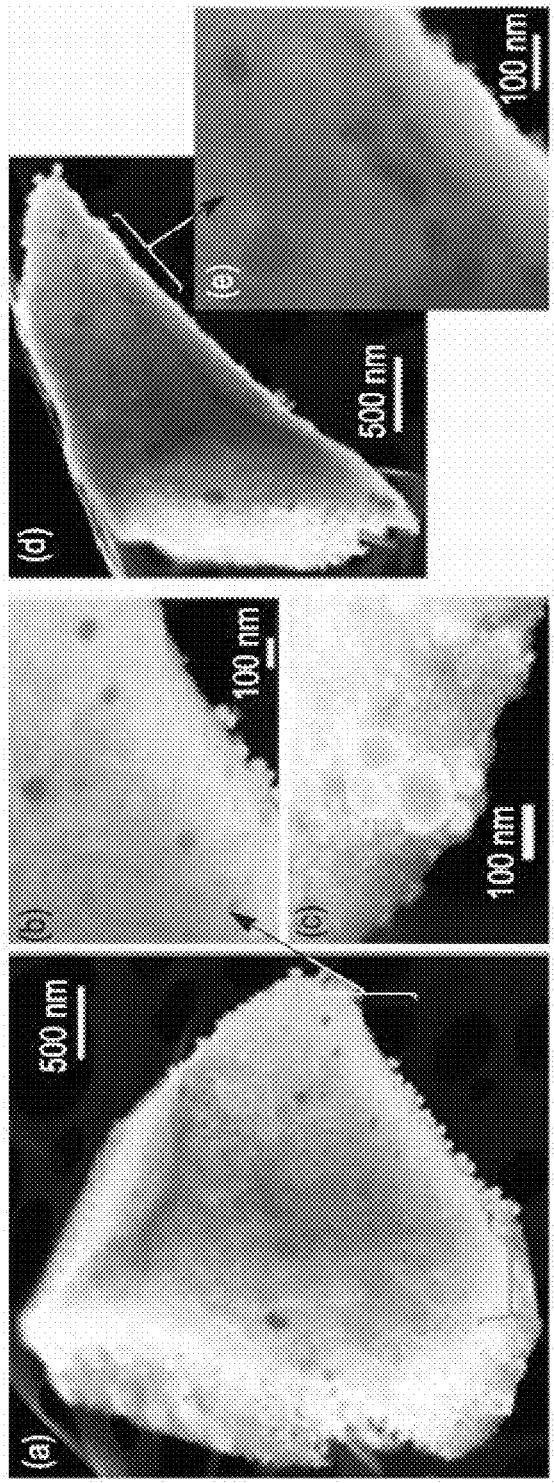

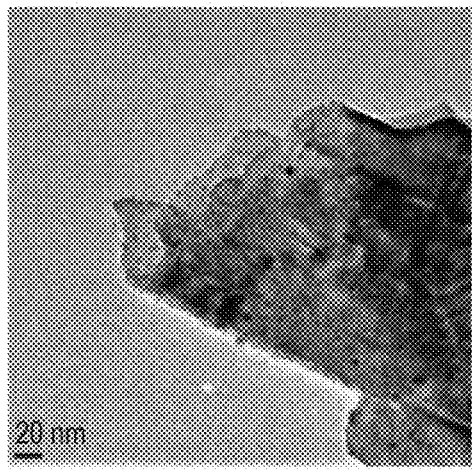 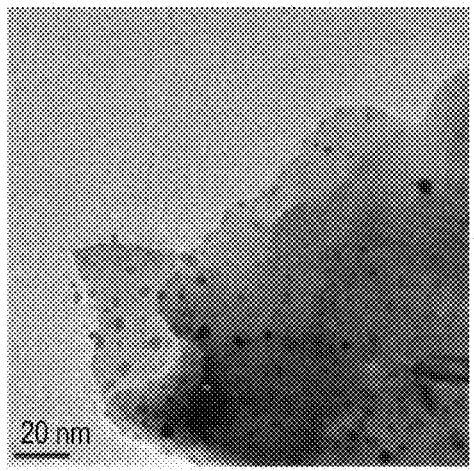
*FIG. 46A*  *FIG. 46B*
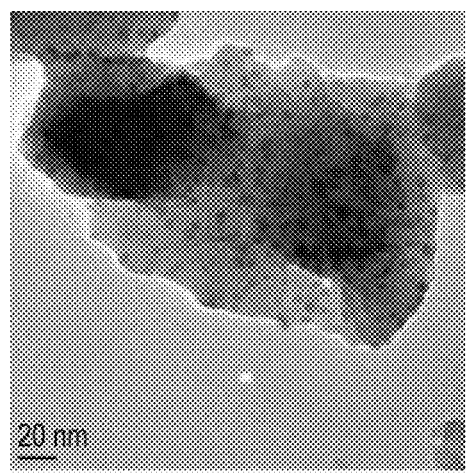
*FIG. 47*

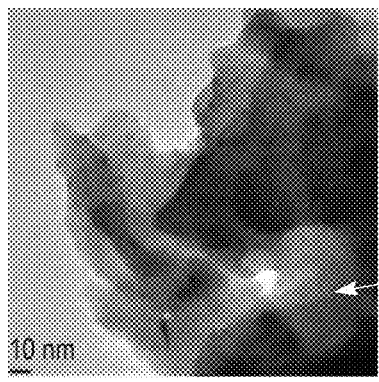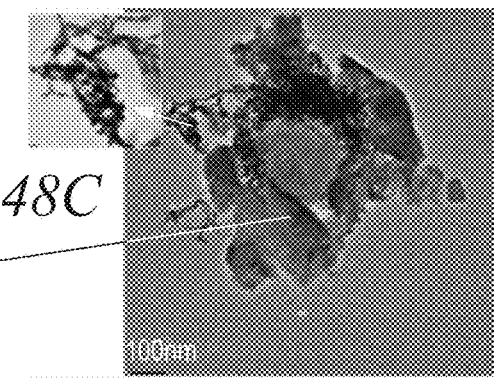
FIG. 48A  FIG. 48B
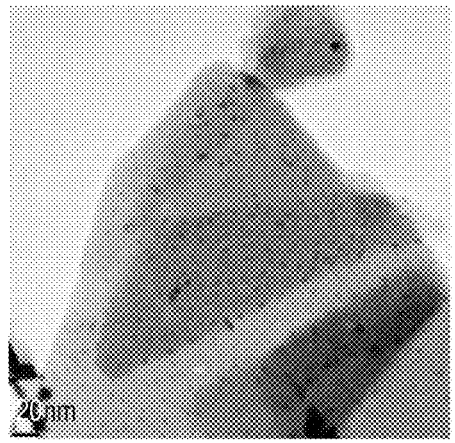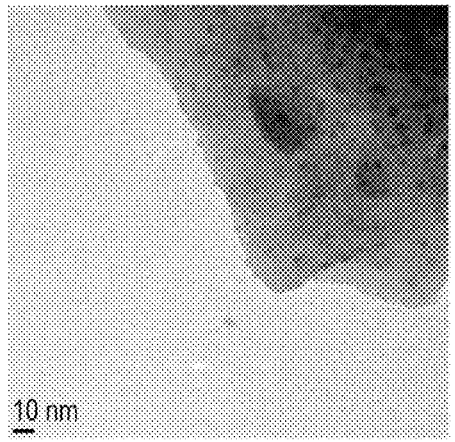
FIG. 49A  FIG. 49B

NANOPARTICLE CATALYSTS FOR CONVERSION OF CYCLOHEXANOL TO CYCLOHEXANONE

CROSS-REFERENCE TO RELATED APPLICATIONS

This application claims priority under 35 U.S.C. §119(e) to U.S. Provisional Patent Application No. 62/235,684, filed Oct. 1, 2015, the disclosure of which is hereby incorporated herein by reference in its entirety

FIELD

The present invention relates to catalysts, and in particular catalysts including noble metal nanoparticles useful for the conversion of cyclohexanol to cyclohexanone.

BACKGROUND

Cyclohexanone is commonly used in the production of ε-caprolactam, which is a raw material used in the production of nylon 6. Nylon 6 has many uses including as a raw material used in industry and manufacturing.

Cyclohexanone is typically produced industrially by the hydrogenation of phenol or the oxidation of cyclohexane. These typical processes produce the by-product cyclohexanol, leading to the formation of a mixture of cyclohexanone and cyclohexanol known as KA-oil.

Improvements in the foregoing processes are desired.

SUMMARY

The present disclosure provides catalysts and methods for the conversion of cyclohexanol to cyclohexanone. In one embodiment, the catalysts comprise a microporous copper chloropyrophosphate (CuClP) framework including a plurality of noble metal nanoparticle sites.

In one exemplary embodiment, a method of converting an alcohol to a ketone is provided. The method includes reacting the alcohol in the presence of a catalyst to produce the ketone, wherein the catalyst comprises a microporous copper chloropyrophosphate framework including a plurality of noble metal nanoparticles. In one more particular embodiment, the reaction is performed in the presence of oxygen. In one more particular embodiment, the alcohol is a cyclic alcohol. In an even more particular embodiment, the alcohol is cyclohexanol and the ketone is cyclohexanone. In an even more particular embodiment, the cyclohexanol is provided as a mixture of cyclohexanone and cyclohexanol, wherein the mixture comprises 5 wt. % to 95 wt. % cyclohexanol, 40 wt. % to 60 wt. % cyclohexanol, or about 50 wt. % cyclohexanol, based on the total weight of the cyclohexanol and cyclohexanone.

In one exemplary embodiment, a catalyst is provided. The catalyst comprises a microporous copper chloropyrophosphate framework including a plurality of noble metal nanoparticles.

In a more particular embodiment, the microporous copper chloropyrophosphate framework has the general formula:

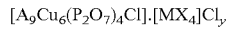

where: A is selected from K, Rb, Cs, and $NH_4$;
M is selected from Cu, Au, Pt, and Pd;
X is selected from Cl and Br; and
y is 2 when M is Pt, Pd, or Cu and y is 3 when M is Au.

In more particular embodiment of any of the above embodiments, the microporous copper chloropyrophosphate framework has a general formula selected from the group consisting of: $Rb_9Cu_6(P_2O_7)_4Cl_4(AuCl_4)$, $Rb_9Cu_6(P_2O_7)_4Cl_3(PtCl_4)$, and $Rb_9Cu_6(P_2O_7)_4Cl_3(PdCl_4)$.

In a more particular embodiment of any of the above embodiments, the catalyst comprises precursor complexes that result in isolated noble metal nanoparticle sites upon activation. In an even more particular embodiment, the precursor complexes are selected from the group consisting of $[PtCl_4]^{2-}$, $[PdCl_4]^{2-}$, and $[AuCl_4]^{-}$.

In one more particular embodiment of any of the above embodiments, the noble metal nanoparticles include at least one metal selected from the group consisting of platinum, palladium, and gold. In one more particular embodiment, the metal is platinum. In another more particular embodiment, the metal is palladium. In still another more particular embodiment, the metal is gold. In still another more particular embodiment, the noble metal nanoparticles include at least two metals selected from the group consisting of platinum, palladium, and gold, and even more particularly, the two metals are platinum and gold.

In one more particular embodiment, the catalyst comprises a microporous copper chloropyrophosphate framework including a plurality of mono-metallic platinum nanoparticles. In a more particular embodiment, the catalyst has been activated at a temperature of 175° C. or greater. In an even more particular embodiment, the catalyst has been activated at a temperature of about 200° C. In another more particular embodiment, the catalyst has been activated while exposed to a mixture of hydrogen and nitrogen.

In one more particular embodiment, the catalyst comprises a microporous copper chloropyrophosphate framework including a plurality of platinum and gold nanoparticles. In a more particular embodiment, the catalyst has been activated at a temperature of 200° C. or greater. In an even more particular embodiment, the catalyst has been activated at a temperature of about 300° C. In another more particular embodiment, the catalyst has been activated while exposed to a mixture of hydrogen and nitrogen.

In one more particular embodiment of any of the above embodiments, the metal is in the metallic state. In one more particular embodiment of any of the above embodiments, the metal has an oxidation state of zero.

In one exemplary embodiment, a method of making a catalyst is provided. The method includes mixing copper (II) fluoride, orthophosphoric acid, rubidium hydroxide, rubidium chloride, and a source of metal chloride; heating the mixture in a sealed container to form a catalyst precursor including precursor complexes; and activating the catalyst by heating the catalyst precursor at a temperature of at least 150° C. to convert the precursor complexes to noble metal nanoparticle sites. In a more particular embodiment, the catalyst precursor is heated at a temperature of at least 175° C. or at least 200° C. to activate the catalyst.

In one more particular embodiment, the source of metal chloride is selected from the group consisting of $K_2PtCl_4$, $K_2PdCl_4$, $HAuCl_4$, and $KAuCl_4$. In another more particular embodiment, the precursor complexes are selected from the group consisting of $[PtCl_4]^{2-}$, $[PdCl_4]^{2-}$, and $[AuCl_4]^{-}$.

The above mentioned and other features of the invention, and the manner of attaining them, will become more apparent and the invention itself will be better understood by reference to the following description of embodiments of the invention taken in conjunction with the accompanying drawings.

BRIEF DESCRIPTION OF THE DRAWINGS

FIGS. 13A, 13B, and 13C are related to Example 2 and illustrate ADF AC-STEM images of the Pt/CuClP material activated at 200° C.

FIGS. 14A, 14B, and 14C are related to Example 2 and illustrate ADF AC-STEM images of the Pd/CuClP material activated at 200° C.

FIGS. 15A, 15B, and 15C are related to Example 2 and illustrate ADF AC-STEM images of the Au/CuClP material activated at 200° C.

FIGS. 38A, 38B, 38C, 38D, and 38E are related to Example 2 and illustrate ADF and bright-field STEM images of the Au/CuClP material activated at 250° C.

FIGS. 39A, 39B, 39C, and 39D are related to Example 2 and illustrate ADF-STEM images of the Au/CuClP material activated at 350° C.

FIGS. 39A, 39B, 39C, 39D, and 39E are related to Example 2 and illustrate ADF-STEM images of the Au/CuClP material activated at 350° C.

FIGS. 46A and 46B are related to Example 4 and illustrate TEM images of the AuPd/CuClP material activated at 200° C.

FIG. 47 is related to Example 4 and illustrates a TEM image of the Pt/Pd/CuClP material activated at 150° C.

FIGS. 48A, 48B, and 48C are related to Example 4 and illustrate TEM images of the PtPd/CuClP material activated at 200° C.

FIGS. 49A and 49B are related to Example 4 and illustrate TEM images of the AuPt/CuClP material activated at 200° C.

DETAILED DESCRIPTION

The present disclosure is directed to catalysts and methods for the conversion of cyclohexanol to cyclohexanone.

In one exemplary embodiment, the catalyst is based on a microporous copper chloropyrophosphate (CuClP) framework bearing flexible anion exchange properties. FIG. 1 illustrates an exemplary catalyst 102 having a copper chloropyrophosphate microporous framework architecture. The copper chloropyrophosphates (CuClPs) are a family of microporous framework materials having have the general formula:

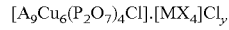

$[A_9Cu_6(P_2O_7)_4Cl] \cdot [MX_4]Cl_y$ where: A is selected from K, Rb, Cs, and $NH_4$;
M is selected from Cu, Au, Pt, and Pd;
X is selected from Cl and Br; and
y is 2 when M is Pt, Pd, or Cu and y is 3 when M is Au.

In one more particular embodiment, the copper chloropyrophosphate has a formula selected from the group consisting of: $Rb_9Cu_6(P_2O_7)_4Cl_4(AuCl_4)$, $Rb_9Cu_6(P_2O_7)_4Cl_3(PtCl_4)$ and $Rb_9Cu_6(P_2O_7)_4Cl_3(PdCl_4)$. In one more particular embodiment, the formula is $Rb_9Cu_6(P_2O_7)_4Cl_4(AuCl_4)$. In another more particular embodiment, the formula is $Rb_9Cu_6(P_2O_7)_4Cl_3(PtCl_4)$. In another more particular embodiment, the formula is $Rb_9Cu_6(P_2O_7)_4Cl_3(PdCl_4)$.

Figure 1A:
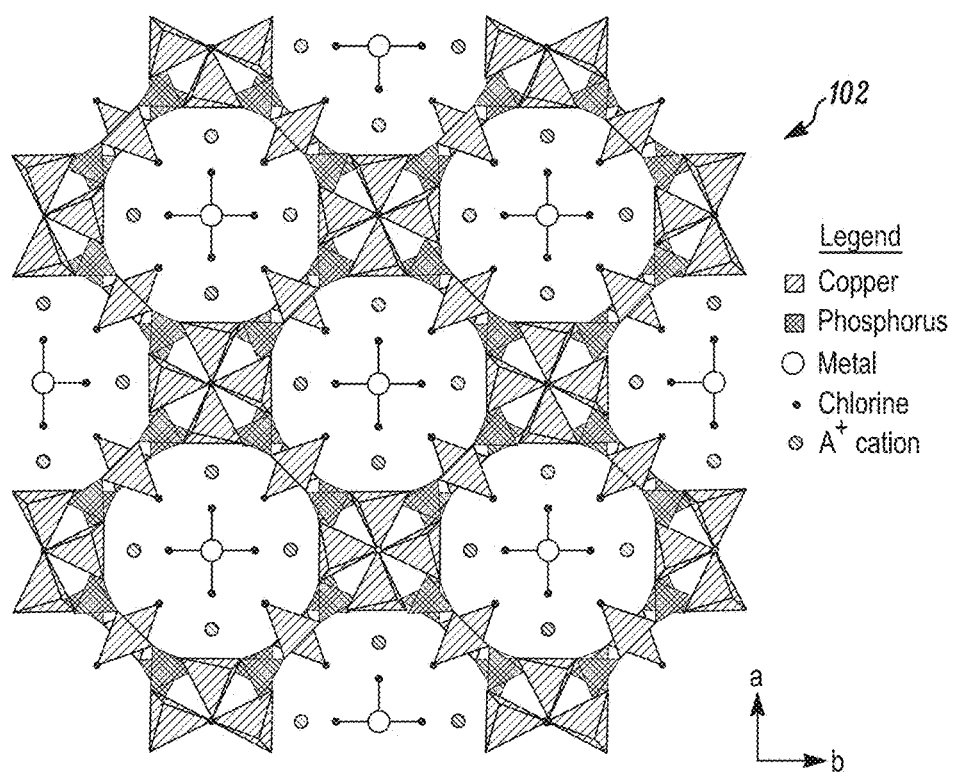
FIG. 1A illustrates an exemplary copper chloropyrophosphate framework as viewed down the c-axis.
Figure 1B:
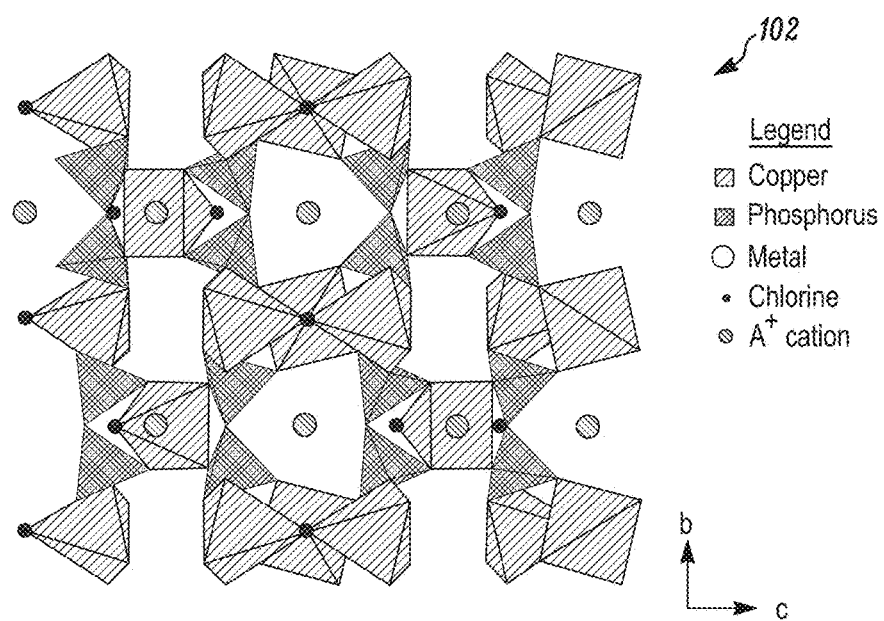
FIG. 1B illustrates the exemplary copper chloropyrophosphate framework of FIG. 1A as viewed down the a-axis.

In one exemplary embodiment, the catalyst comprises a copper (II) framework including 1-dimensional channels with diameters of about 13 Å. An exemplary framework is shown in the a-b plane down the c-axis in FIG. 1A and in the b-c plane down the a-axis in FIG. 1B. The oxygen atoms have been omitted for clarity in FIGS. 1A and 1B. As shown in FIG. 1, the framework is composed of a $\mu^4$ chloride ion at the apex of $4 \times CuO_4$ square-based pyramids. These quartets are linked by pyrophosphate, $P_2O_7$, groups to form one dimensional chains, with the cavities between $[CuO_4]_4Cl[P_2O_7]_4$ blocks along the c-direction occupied by $A^+$ cations. The $[CuO_4]_4Cl[P_2O_7]_4$ units are crosslinked, via a shared oxygen atom on a $P_2O_7$ unit, in the ab plane by square-planar $CuO_4$ groups. This produces a square grid of one-dimensional channels with dimensions approx. 12×12 Å. The channels are lined with $A^+$ cations and, bar structure, chloride ions weakly coordinated to the cross-linking $CuO_4$ square planar units (Cu—Cl approx. 2.7 Å). The orientation of the resulting $CuO_4Cl$ square-based pyramids alternates along the c-axis. The relative orientation of successive $P_2O_7$ di-tetrahedral units in the $[CuO_4]_4Cl[P_2O_7]_4$ blocks along the c-axis allows the structure to flex with expansion and contraction of the channels to incorporate of $A^+$ cations and $[MX_4]$ anions of differing sizes.

The CuClP materials are a series of complex anion-inclusion compounds that contain weakly coordinated square planar $MCl_4$ groups (e.g. $[AuCl_4]^-[PtCl_4]^{2-}$, $[PdCl_4]^{2-}$) that stack neatly on one another in the channels. Without wishing to be bound by any particular theory, it is believed that upon activation, such as by calcination, these anions were found to be extruded from the channels, and generate isolated noble metallic nanoparticles with a size distribution of 2-10 nm.

In one exemplary embodiment, a catalyst is provided. The catalyst comprises a microporous copper chloropyrophosphate framework including a plurality of noble metal nanoparticles.

In one exemplary embodiment, the catalyst comprises a plurality of noble metal nanoparticle sites. Exemplary noble metals include platinum, palladium, and gold. In one exemplary embodiments, the noble metal is in the metallic state or has an oxidation state of zero.

In one exemplary embodiment, the catalyst comprises noble metal nanoparticles of a single metal, referred to herein as mono-metallic noble metal catalysts. Exemplary mono-metallic noble metal catalysts include catalysts with exactly one of platinum, palladium, or gold noble metal nanoparticle sites.

In one exemplary embodiment, the catalyst comprises noble metal nanoparticles of two metals, referred to herein as bi-metallic noble metal catalysts. Exemplary bi-metallic noble metal catalysts include catalysts with exactly two metal selected from the group consisting of platinum, palladium, and gold, such as platinum and palladium, platinum and gold, and palladium and gold.

In one exemplary embodiment, the catalyst comprises a plurality of precursor complexes. Exemplary precursor complexes include metal chloride ions such as $[PtCl_4]^{2-}$, $[PdCl_4]^{2-}$, and $[AuCl_4]^-$. In one exemplary embodiment, the precursor complexes are converted to the noble metal nanoparticle sites by activating the catalyst. Exemplary methods of activating the catalyst include heating the catalyst in the presence of hydrogen at a temperature as little as 150° C., 175° C., 200° C., as great as 250° C., 300° C., 350° C. or higher, or within any temperature range defined between any two of the foregoing values, such as at least 150° C., at least 175° C., at least 200° C., at least 300° C., 150° C. to 300° C., 150° C. to 250° C., 175° C. to 200° C., or 200° C. to 350° C., for as little as 30 minutes, 1 hour, 1.5 hours, as long as 2 hours, 2.5 hours, 3 hours, or longer, or within any range defined between any two of the foregoing values, such as at least 30 minutes, at least 2 hours, 1.5 hours to 3 hours, or 2 hours to 3 hours. In one more particular embodiment, the catalyst is heated in a hydrogenous environment. In another more particular embodiment, the catalyst is activated by heating the catalyst under a flow of 5% hydrogen/nitrogen at a flow rate of 150 mL·min$^{-1}$.

In one exemplary embodiment, the catalyst is an Au/CuClP mono-metallic material activated by heating the material in the presence of hydrogen at a temperature of about 350° C. In one exemplary embodiment, the catalyst is a Pt/CuClP mono-metallic material activated by heating the material in the presence of hydrogen at a temperature of about 200° C. In one exemplary embodiment, the catalyst is a Pd/CuClP mono-metallic activated by heating the material in the presence of hydrogen at a temperature of about 150° C. In one exemplary embodiment, the catalyst is a PtPd/CuClP bi-metallic material activated by heating the material in the presence of hydrogen at a temperature of 150° C. to 200° C. or about 200° C. In one exemplary embodiment, the catalyst is an AuPt/CuClP bi-metallic material activated by heating the material in the presence of hydrogen at a temperature of 200° C. to 350° C., 250° C. to 300° C., or about 300° C.

In one embodiment, an exemplary catalyst is made by mixing copper (II) fluoride, orthophosphoric acid, rubidium hydroxide, rubidium chloride, and a source of metal chloride; heating the mixture in a sealed container to form a catalyst precursor including precursor complexes. In one exemplary embodiment, a mono-metallic catalyst is formed by selecting a single source of metal chloride. In another exemplary embodiment, a bi-metallic catalyst is formed by selecting two sources of metal chlorides, each containing a different metal. Exemplary sources of metal chloride include $K_2PtCl_4$, $K_2PdCl_4$, and $HAuCl_4$. In some exemplary embodiments, the catalyst comprises the metal in an amount as little as about 0.1 wt. %, 0.5 wt. %, 1 wt. %, as great as 2 wt. %, 5 wt. %, 10 wt. %, 15 wt. %, or within any range defined between any two of the foregoing values, such as 0.1 wt. % to 15 wt. %, or 1 wt. % to 10 wt. % for example.

In one exemplary embodiment, nanoparticles of substantially uniform size are formed based on the extrusion of metal chloride precursor complex anions, such as $MCl_x$ where M=Au, Pt or Pd, from a crystalline microporous copper chloropyrophosphate framework. The framework is illustratively of CU-2 topology and has flexible anion-exchange properties. As illustratively shown in FIGS. 1A and 1B, the parent CU-2 framework consists of a $\mu^4$ chloride ion at the apex of 4×CuO$_4$Cl square-based pyramids. These quartets are linked by pyrophosphate, $P_2O_7$, groups, to form one dimensional chains, with the cavities between $[CuO_4]_4$ $Cl[P_2O_7]_4$ blocks along the c-direction occupied by A$^+$ cations. The $[CuO_4]_4Cl[P_2O_7]_4$ units are cross-linked, via a shared oxygen atom on a $P_2O_7$ unit, in the a-b plane by square-planar CuO$_4$ groups, this produces producing a square grid of 1-dimensional channels extending through the catalyst in the c-axis direction with dimensions ~12×12 Å. In some exemplary embodiments, the channels are lined with A$^+$ cations and/or chloride ions, with weakly coordinated (Cu—Cl ~2.7 Å) to the cross-linking CuO$_4$ square planar units. The orientation of the resulting CuO$_4$Cl square-based pyramids alternates for copper sites along the c-axis. Without wishing to be held to any particular theory, it is believed that the relative orientation of successive $P_2O_7$ di-tetrahedral units in the $[CuO_4]_4Cl[P_2O_7]_4$ blocks along the c-axis allows the structure to flex with expansion and contraction of the channels to incorporate of A$^+$ cations and $[MX_4]$ anions of differing sizes. For a specific anion a linear relationships exists between cation radius, lattice parameters and the torsional angle (O—P . . . P—O) between neighboring pyrophosphate units. The channels contain site-disordered free (fluoro- or hydrogen-) phosphate tetrahedra $[P(O/OH/F)_4]$ (see. FIG. 1). In some more particular embodiments, the phosphate anions are replaced with square planar species ($CuCl_4^{2-}$ is a flattened tetrahedron, $D_{2d}$) which stack with their faces orientated perpendicular to the channel direction This elongation and compression of the channels is believed to produce an interaction between cross-linking CuO$_4$ unit copper site and the oxygen of a free phosphate anion within the channels, with a Cu—O distance of 2.285 Å; it also is believed to allow for the formation of a more ideal coordination geometry.

Figure 2A:
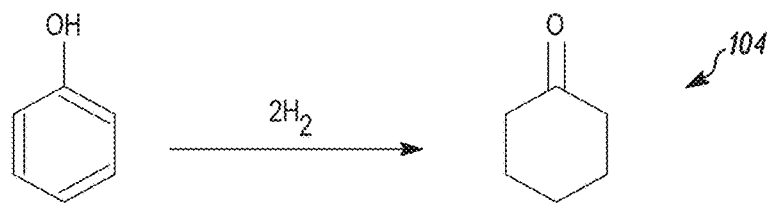
FIG. 2A illustrates the hydrogenation of phenol to form cyclohexanone.
Figure 2B:
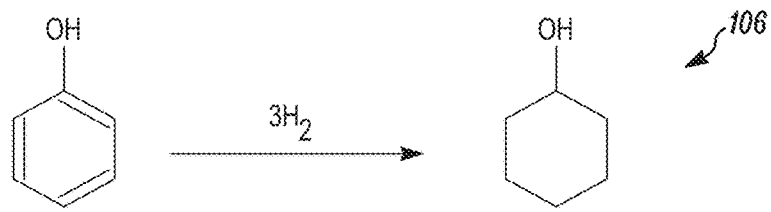
FIG. 2B illustrates the hydrogenation of phenol to form cyclohexanol.

As illustrated by the reaction 104 in FIG. 2A, phenol can be hydrogenated in the presence of a catalyst, to form cyclohexanone. Exemplary catalysts include palladium, platinum, ruthenium, and other suitable catalysts. However, a portion of the phenol is hydrogenated to form cyclohexanol according to reaction 106 in FIG. 2B.

Figure 3:
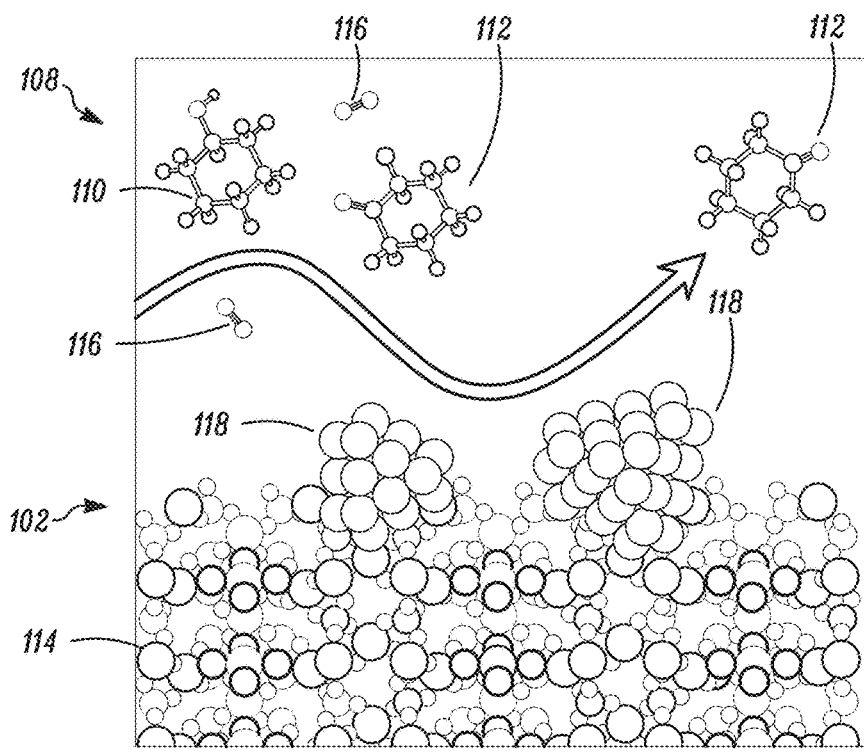
FIG. 3 illustrates the reaction of the mixture of cyclohexanone and cyclohexanol to cyclohexanone with an exemplary catalyst.

As shown in FIG. 3, a mixture 108 of cyclohexanol 110 and cyclohexanone 112 is brought in to proximity with the catalyst 102 and oxygen 116. The catalyst 102 illustratively includes a microporous copper chloropyrophosphate framework 114 and a plurality of noble metal nanoparticles 118 that serve as activation sites for the conversion of cyclohexanol 110 to cyclohexanone 112.

In one exemplary embodiment, the cyclohexanol to be converted to cyclohexanone is provided as a mixture of cyclohexanone and cyclohexanol. In some exemplary embodiments, the weight percent of cyclohexanol is as little as 5 wt. %, 10 wt. %, 20 wt. %, 25 wt. %, 30 wt. %, 40 wt. %, 45 wt. %, 50 wt. %, as great as 55 wt. %, 60 wt. %, 70 wt. %, 75 wt. %, 80 wt. %, 90 wt. %, 95 wt. %, based on the total weight of the cyclohexanol and cyclohexanone in the mixture, or within any range defined between any two of the foregoing values, such as 5 wt. % to 95 wt. %, 20 wt. % to 80 wt. %, 40 wt. % to 60 wt. %, or 45 wt. % to 55 wt. %. In one exemplary embodiment, the mixture comprises about 50 wt. % cyclohexanol, based on the total weight of the cyclohexanol and cyclohexanone.

In one exemplary embodiment, the catalytic conversion of cyclohexanol to cyclohexanone is typically performed at a temperature beneath 250° C. In one exemplary embodiment, the catalytic conversion of cyclohexanol to cyclohexanone is typically performed at a temperature beneath 350° C. In other embodiments, the reaction may be performed at a temperature as low as about 150° C., 180° C., 190° C., as high as 200° C., 210° C., 220° C., 250° C., or within any range defined between any pair of the foregoing values, such as 150° C. to 250° C., 180° C. to 220° C., or 190° C. to 210° C. In one exemplary embodiment, the catalytic conversion of cyclohexanol to cyclohexanone is performed at atmospheric pressure; in other exemplary embodiments, higher or lower pressures may be used.

The efficiency of the conversion may be expressed in terms of conversion of cyclohexanol, selectivity of the desired cyclohexanone product, or yield. Conversion is a measure of the amount of cyclohexanol reactant that is consumed by the reaction. Higher conversions are more desirable. The conversion is calculated as:

$$\text{Conversion (mol \%)} = 100\% \times \left(1 - \frac{\text{moles of reactant remaining}}{\text{moles of reactant supplied}}\right)$$

Selectivity is a measure of the amount of the desired cyclohexanone product that is produced relative to all reaction products. Higher selectivities are more desirable. Lower selectivities indicate a higher percentage of reactant being used to form undesired products. The selectivity is calculated as:

$$\text{Selectivity (mol \%)} =$$
$$100\% \times \frac{\text{moles of desired cyclohexanone product produced}}{\text{moles of reactant supplied} - \text{moles of reactant remaining}}$$

Yield is a measurement that combines selectivity and conversion. Yield indicates how much of the incoming reactant is reacted to form the desired cyclohexanone. The yield is calculated as:

Yield (mol %)=Selectivity (mol %)×Conversion (mol %)/100%

In some exemplary embodiments, the methods according to the present disclosure result in high conversion and selectivity for the desired cyclohexanone.

In one embodiment, the conversion of cyclohexanol is 50% or higher. In a more particular embodiment, the conversion is from about 50% to about 100%. For example, the conversion may be as low as about 50%, 60%, 70%, 70%, 75% or as high as about 80%, 85%, 90%, 95%, 97.5%, 99%, 99.5%, approaching 100%, or 100%, or may be within any range defined between any pair of the foregoing values.

In one embodiment, the selectivity of cyclohexanone is 50% or higher. In a more particular embodiment, the selectivity is as low as about 50%, 55%, 60%, 65%, or as high as about 70%, 75%, 80%, 85%, 90%, 95%, 97.5%, 99%, 99.5%, approaching 100%, or may be within any range defined between any pair of the foregoing values.

In one embodiment, the yield is 30% or higher. In a more particular embodiment, the yield is as low as about 30%, 35%, 40%, 45%, 50%, 55%, 60%, 65%, or as high as about 70%, 75%, 80%, 85%, 90%, 95%, 97.5%, 99%, 99.5%, approaching 100%, or may be within any range defined between any pair of the foregoing values.

Example 1: Synthesis and Activation of Catalyst

Synthesis: Chemicals for synthesis were purchased from Sigma Aldrich or Fisher Scientific and used without further purification, except RbCl, which was dried under vacuum at 100° C.

Copper(II) fluoride (0.1168 g, 1.150 mmol), 85 wt. % orthophosphoric acid (0.2 mL, 2.922 mmol), 50 wt. % RbOH (0.24 mL, 2.037 mmol), RbCl (0.28 g; 2.316 mmol) and a source of $MCl_x$; $HAuCl_4 \cdot xH_2O$ (0.0489 g, 0.144 mmol, 7 wt. % Au), $K_2PtCl_4$ (0.0598 g, 0.144 mmol, 7 wt. % Pt) or $K_2PdCl_4$ (0.0470 g, 0.144 mmol, 4 wt. % Pd) were mixed in the Teflon® liner of a custom-made 23 mL hydrothermal vessel. The vessel was sealed and heated to 175° C. for 2 days.

Copper(II) fluoride (0.1168 g, 1.15 mmol), rubidium chloride (0.2800 g, 2.32 mmol) and a source of metal chloride salt selected from 0.0489 g (0.144 mmol) gold(III) chloride hydrate, 0.0515 g (0.124 mmol) potassium tetrachloroplatinate, or 0.0405 g (0.124 mmol) potassium tetrachloropalladate were accurately weighed out to 4 decimal places and ground in an agate pestle and mortar for 2 minutes to homogenize.

The mixture was added to the Teflon® liner of a 23 mL hydrothermal vessel, and 85% orthophosphoric acid in water (0.20 mL, 2.92 mmol) was added dropwise wetting the entire contents. The mixture was sonicated for 5 minutes to encourage mixing. 0.24 mL (2.38 mmol) of 50 wt. % rubidium hydroxide in water was added dropwise, wetting the entire contents, and the mixture was sonicated for 10-15 minutes until the mixture was homogenous. Caution was taken due to production of hydrogen fluoride gas.

The hydrothermal vessel was sealed and heated to 175° C. for 48 hours in a convection oven. The vessels were allowed to cool naturally before collecting the product by filtration, washing with deionized water (100 mL) and drying overnight at 80° C.

Products formed as brilliant green cuboid crystals for both the Au and Pt material, and as light brown crystals for the Pd material.

Activation Procedure: Gases were sourced from BOC Industrial Gases and used as purchased. Materials were activated by reduction under a flow of 5% $H_2/N_2$ at approx. 150 $mLmin^{-1}$, for 2 hours at the specified temperature, generating the active nanoparticle catalysts. After reduction, the Au material appeared unchanged in color when activated at temperatures below 250° C., but a dark red color when activated at temperatures above 250° C., while the Pd material appeared black in color and the Pt catalyst a darker khaki-green.

Example 2: Characterization of Catalysts

X-Ray Photoelectron Spectroscopy (XPS) and X-Ray Absorption Spectroscopy (XAS)

X-ray photoelectron spectroscopy (XPS) was employed to probe the nature of noble metal species adjacent to the surface of the microporous framework, with respect to different activation temperatures. XPS analysis was performed using a Thermo Scientific K-Alpha instrument equipped with monochromated Al $K_\alpha$ source at the EPSRC XPS User's Service (NEXUS), University of Newcastle. A flood gun was used for charge compensation. A pass energy of 200 eV and a step size of 1.0 eV was employed for all survey spectra while a pass energy of 40 eV and a step size of 0.1 eV was used for high-resolution spectra of the elements of interest. All XPS spectra were calibrated against the carbon and/or oxygen 1s peaks, and high resolution spectra were fitted with Shirley backgrounds before peak analysis using the CasaXPS software.

Figure 4A:
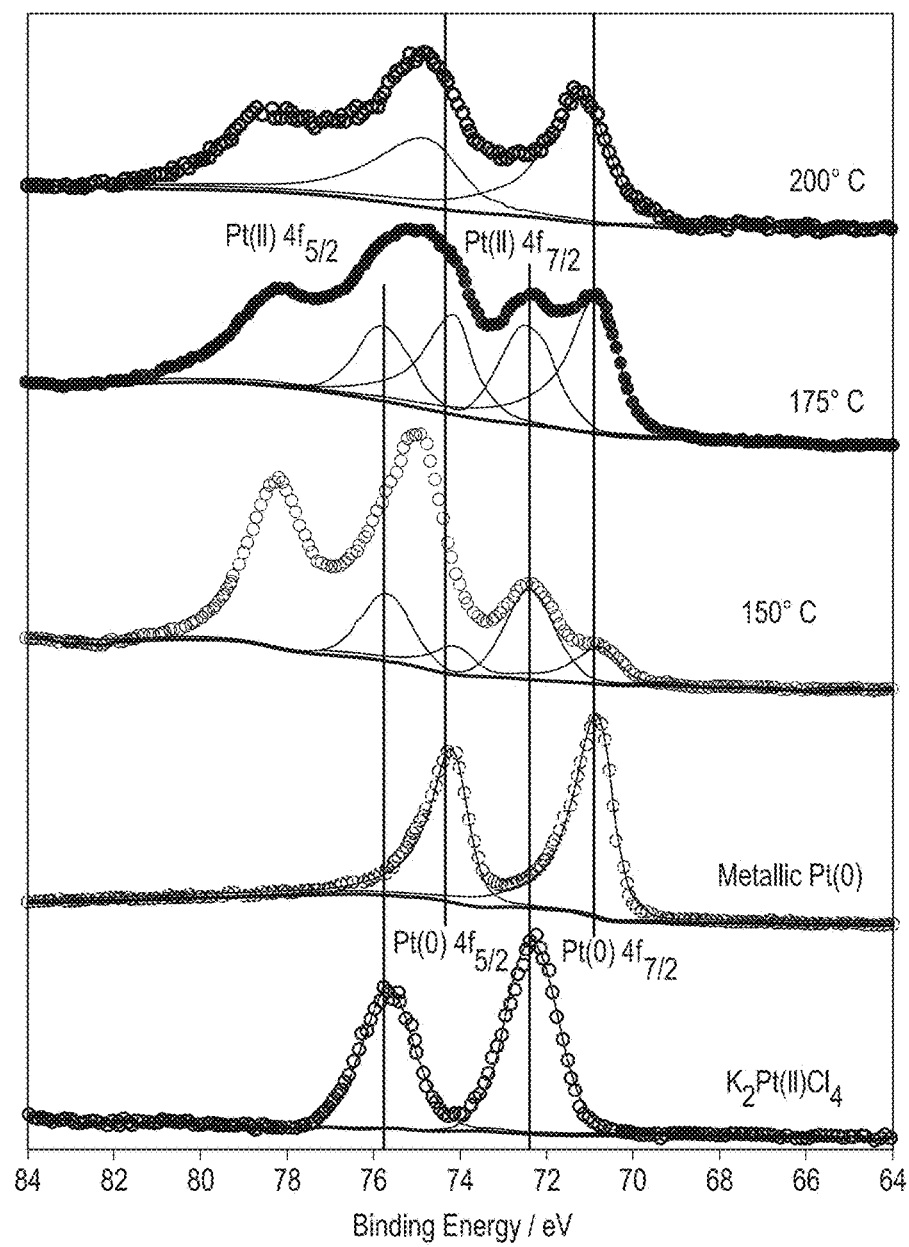
FIGS. 4A and 4B are related to Example 2 and illustrate stacked XPS spectra, with data fits and appropriate reference samples, of exemplary Pt/CuClP catalyst materials activated at different temperatures.

FIG. 4A illustrates stacked XPS data with data fits and appropriate reference samples for the Pt/CuClP materials activated at different temperatures, with the appropriate standards for comparisons showing the progressive decrease in Pt(II) content and the mirrored increase in Pt(0) species with increased activation temperature, with the final sample exhibiting complete formation of Pt(0).

Figure 4B:
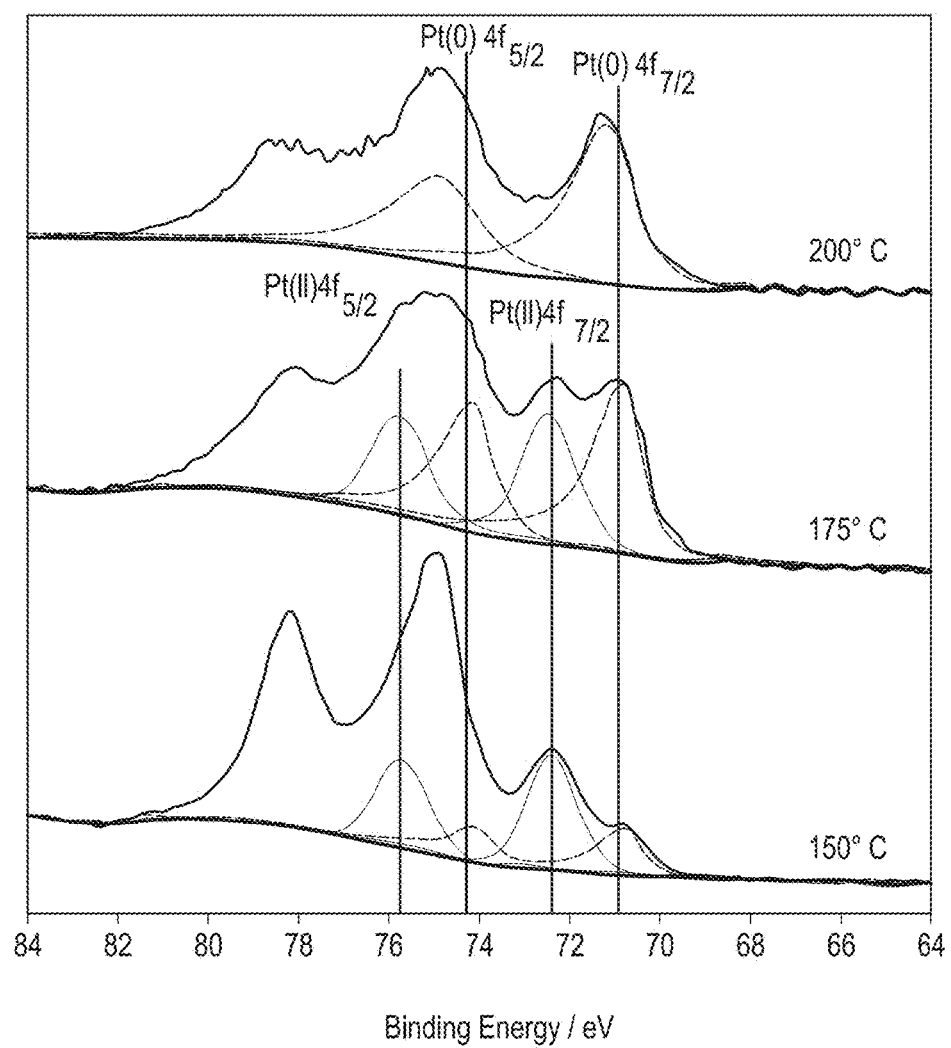
Figure 5:
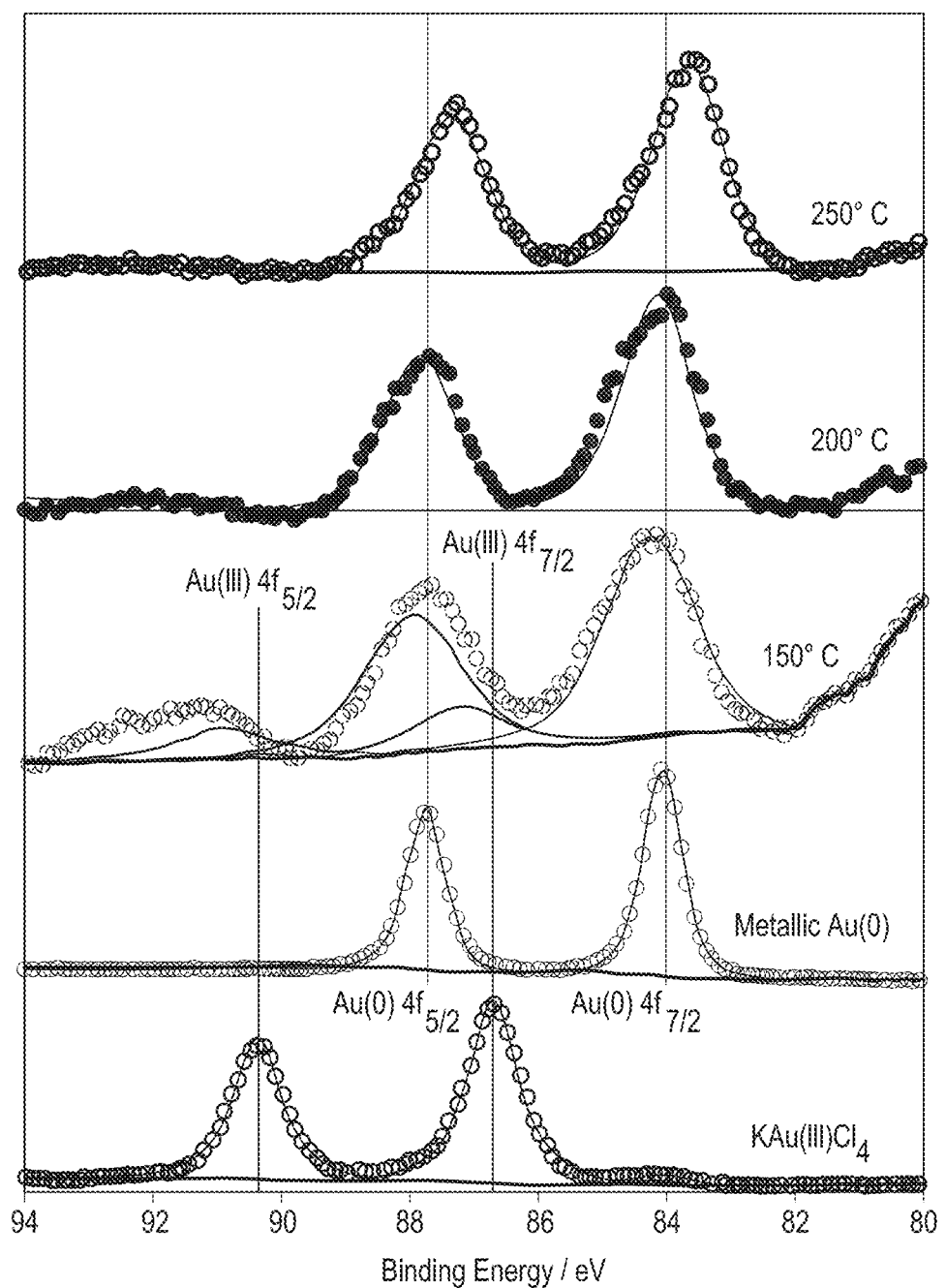
FIG. 5 is related to Example 2 and illustrates stacked XPS spectra, with data fits and appropriate reference samples, of exemplary Au/CuClP catalyst materials activated at different temperatures.
Figure 20A:
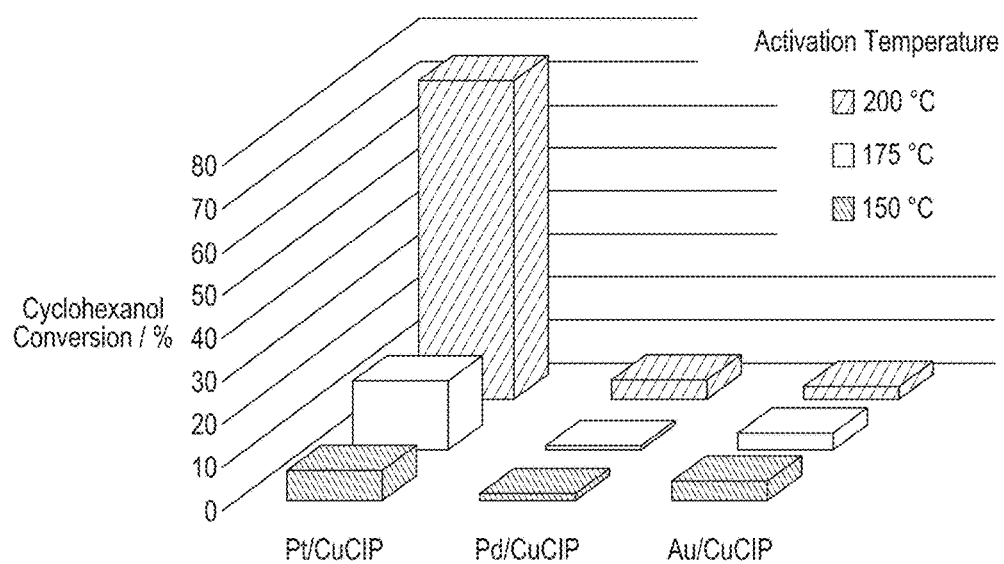
FIG. 20A is related to Example 3 and illustrates the aerobic production of cyclohexanone with supported nanoparticle/CuClP catalysts activated at different temperatures.

FIG. 4B depicts the XPS spectra with data fits and appropriate reference samples of the three Pt/CuClP species reduced using different activation temperatures. A clear trend was observed for the Pt/CuClP catalyst, which showed a transition from a mixture of Pt(II) and Pt(0) with $4f_{7/2}$ peaks at 72.4 eV and 70.8 eV respectively, to purely Pt(0) species, as the activation temperature was progressively increased from 150 to 200° C.: (FIG. 20A). Furthermore, it was established that an activation temperature of 200° C. was sufficient for the complete reduction of the Pt precursors to form nanoparticles under these activation conditions FIG. 5 illustrates stacked XPS data with data fits and appropriate reference samples for the Au/CuClP materials activated at different temperatures, with the appropriate standards for comparisons showing the loss of Au(III) content and the complete formation of Au(0) at temperatures above 200° C.)

XAS for palladium, platinum, and gold were carried out on the B18 beam line at the Diamond Light Source, Didcot, UK. Measurements were performed using a QEXAFS set-up with a fast-scanning Si (111) or Si (311) double crystal monochromator. The normal time resolution of the spectra reported herein was 1 min/spectrum ($k_{max}$=16), on average six scans were acquired to improve the signal-to-noise level of the data. All samples were diluted with cellulose and pressed into pellets to optimize the effective edge-step of the XAFS data and measured in transmission mode using ion chamber detectors. All transmission XAFS spectra were acquired concurrently with the appropriate reference foil placed between $I_t$ and $I_{ref}$. XAS data processing and EXAFS (extended X-ray absorption fine structure) analysis were performed using IFEFFIT with the Horae package (Athena and Artemis). The amplitude reduction factor, $S_0^2$, was derived from EXAFS data analysis of known compounds, and used as a fixed input parameter.

Figure 6A:
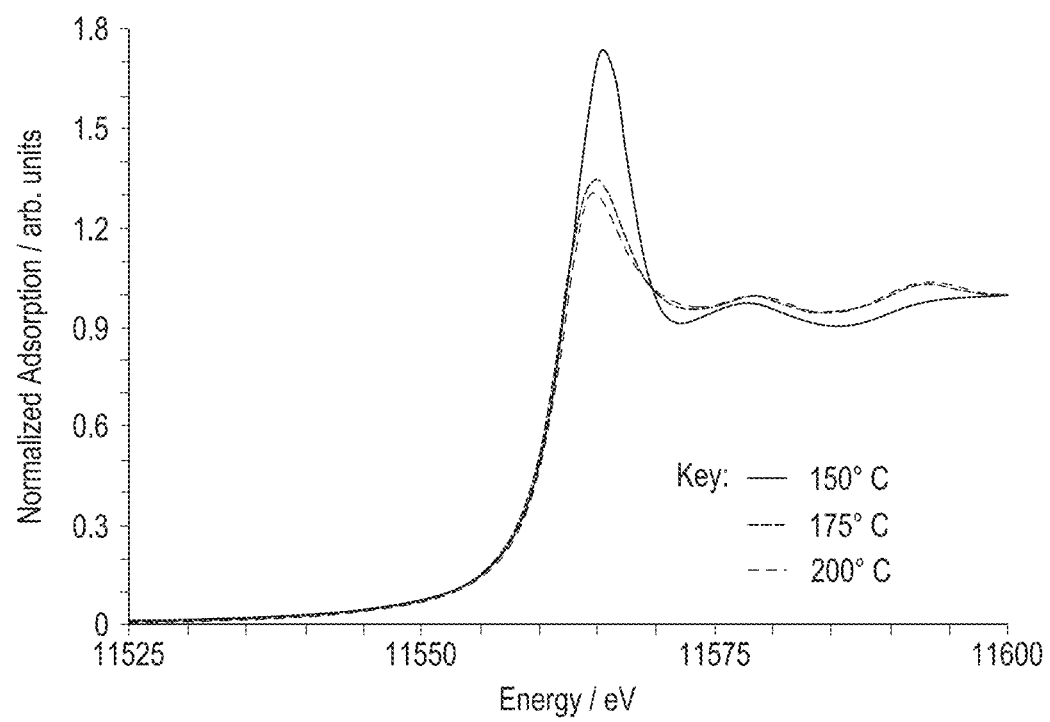
FIG. 6A is related to Example 2 and illustrates stacked Pt $L_3$ edge XANES data for exemplary Pt/CuClP catalyst materials activated at different temperatures.

FIG. 6A illustrates stacked X-ray absorption near edge structure (XANES) data for the Pt/CuClP materials activated at different temperatures, showing the progressive decrease in white line intensity as the activation temperature is increased, signifying the decrease in Pt oxidation state.

Figure 6B:
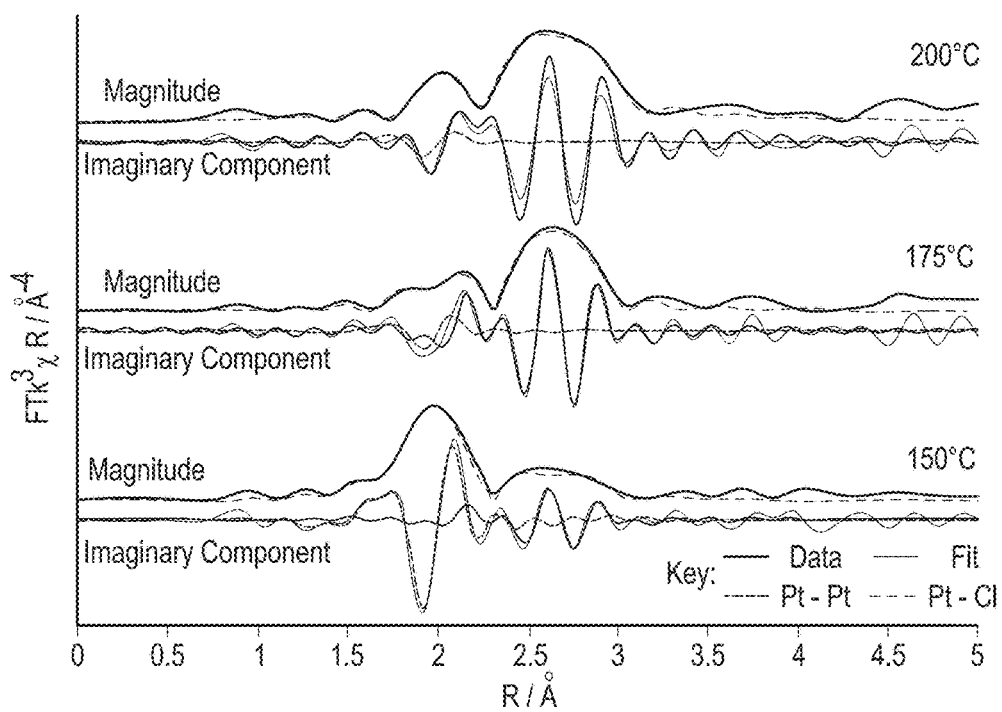
FIG. 6B is related to Example 2 and illustrates the magnitude and imaginary component of the $k^3$ weighted Fourier transform for the EXAFS data, with data fits, of three exemplary Pt/CuClP catalyst species reduced using different activation temperatures.

FIG. 6B illustrates the magnitude and imaginary component of the $k^3$ weighted Fourier transform for the fitted EXAFS data of the three Pt/CuClP species reduced using different activation temperatures.

Both the XPS and XAS techniques demonstrate the progressive reduction of the $[PtCl_4]^{2-}$ precursor towards the metallic Pt(0) species with increase in temperature. FIG. 4B is plotted with reference samples in FIG. 4A. For FIG. 6B the associated scattering paths are included for the imaginary component and the fitting parameters are displayed in Table 1.

TABLE 1

Pt EXAFS fitting parameters for the fits displayed in FIG. 6B.

| Sample | Abs Sc | N | R/Å | $2\sigma^2/Å^2$ | $E_f$/eV | $R_{factor}$ |
|---|---|---|---|---|---|---|
| Pt/CuClP 150° C. | Pt-Cl | 3.7 (2) | 2.320 (5) | 0.0027 (3) | 9.5 (8) | 0.012 |
| | Pt-Pt | 3.4 (5) | 2.768 (7) | 0.0056 (5) | | |
| Pt/CuClP 175° C. | Pt-Cl | 0.8 (1) | 2.31 (9) | 0.0026 (8) | 7.9 (7) | 0.006 |
| | Pt-Pt | 8.9 (3) | 2.76 (2) | 0.0059 (1) | | |
| Pt/CuClP 200° C. | Pt-Cl | 0.4 (1) | 2.32 (2) | 0.003 (2) | 7.6 (6) | 0.006 |
| | Pt-Pt | 9.6 (4) | 2.760 (3) | 0.0059 (2) | | |

Pt sample-$S_0^2$ = 0.91 as deduced by Pt foil standard; Fit range 3 < k < 14, 1.15 < R < 3;
# of independent points = 12.

Figure 7:
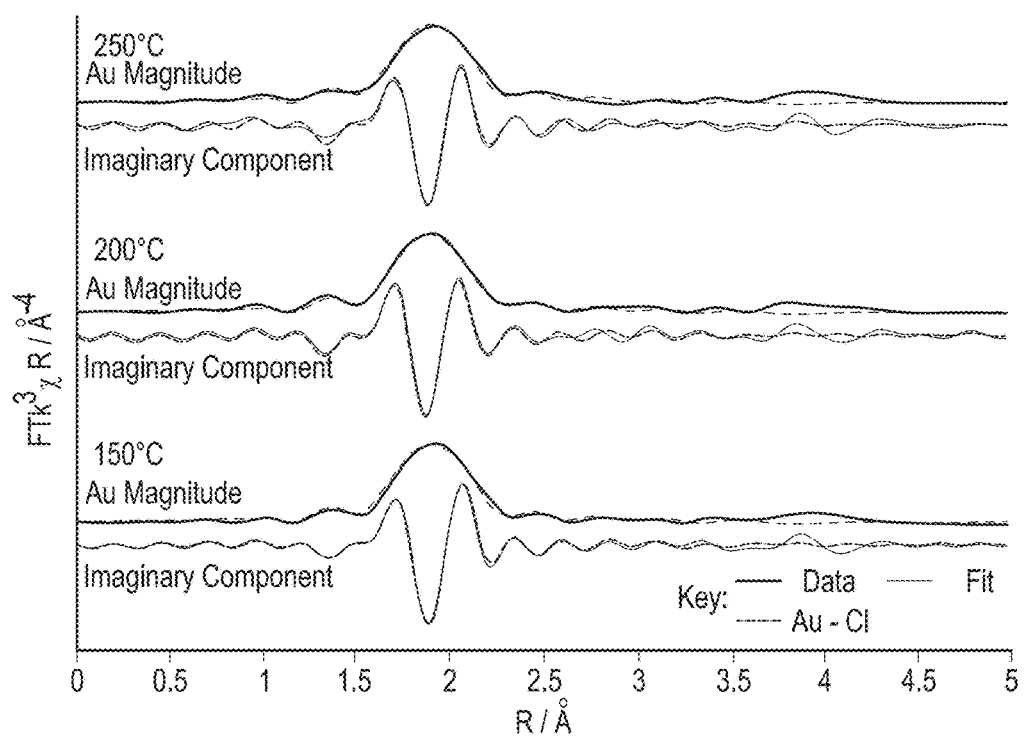
FIG. 7 is related to Example 2 and illustrates the magnitude and imaginary component of the $k^3$ weighted Fourier transform for the EXAFS data, with data fits, of three exemplary Au/CuClP catalyst species reduced under increasing activation temperatures.

FIG. 7 illustrates the magnitude and imaginary component of the $k^3$ weighted Fourier transform for the fitted EXAFS data of the three Au/CuClP species reduced under increasing activation temperatures, exhibiting the majority $[AuCl_4]^-$ precursor, with minimal signs for the reduction from the Au(III) towards Au(0) in the bulk. Associated scattering paths are included for the imaginary component and the fitting parameters are provided in Table 2.

TABLE 2

Au EXAFS fitting parameters for the fits displayed in FIG. 7.

| Sample | Abs Sc | N | R/Å | $2\sigma^2/Å^2$ | $E_f$/eV | $R_{factor}$ |
|---|---|---|---|---|---|---|
| Au/CuClP 150° C. | Au-Cl | 3.7 (1) | 2.287 (4) | 0.0027 (2) | 9.9 (6) | 0.004 |
| Au/CuClP 200° C. | Au-Cl | 2.24 (7) | 2.269 (4) | 0.0028 (3) | 7.3 (7) | 0.009 |
| Au/CuClP 250° C. | Au-Cl | 3.1 (1) | 2.282 (5) | 0.0029 (3) | 9.4 (9) | 0.010 |

Au sample-$S_0^2$ = 0.75 as deduced by KAuCl$_4$ standard; Fit range 3.5 < k < 12.5, 1.1 < R < 3;
# of independent points = 10.

Figure 8:
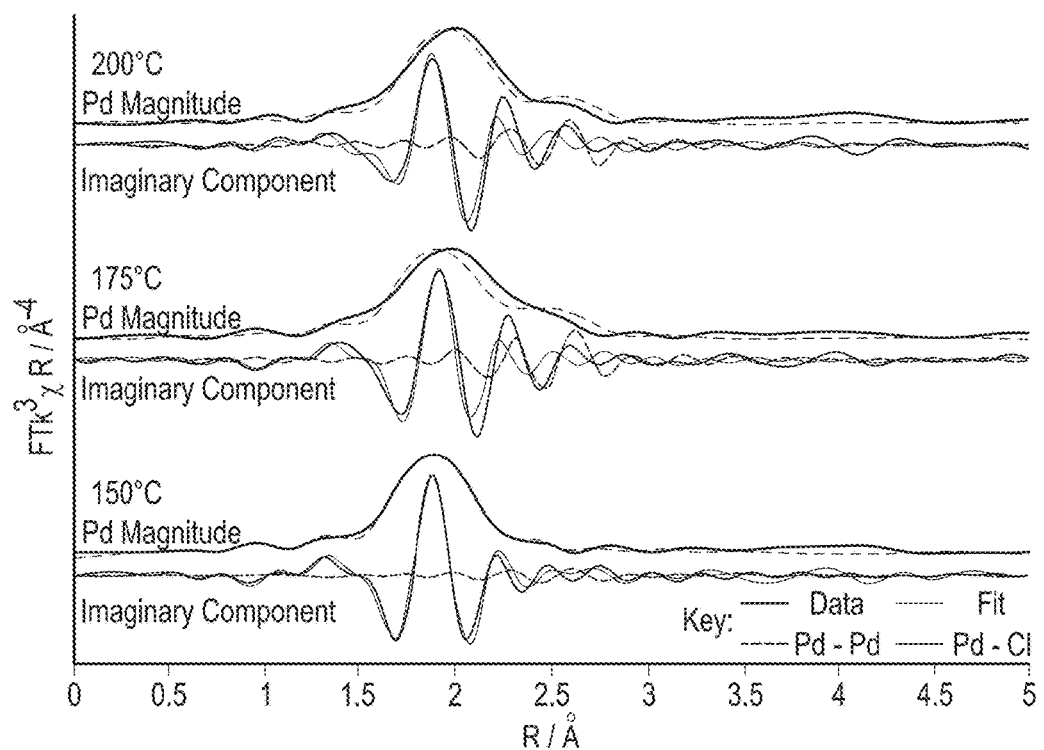
FIG. 8 is related to Example 2 and illustrates the magnitude and imaginary component of the $k^3$ weighted Fourier transform for the EXAFS data, with data fits, of three exemplary Pd/CuClP catalyst species reduced under increasing activation temperatures.

FIG. 8 illustrates the magnitude and imaginary component of the $k^3$ weighted Fourier transform for the fitted EXAFS data of the three Pd/CuClP species reduced under increasing activation temperatures, demonstrating a minor reduction in Pd—Cl contribution with increase in activation temperature. Associated scattering paths are included for the imaginary component and the fitting parameters are provided in Table 3.

TABLE 3

Pd EXAFS fitting parameters for the fits displayed in FIG. 8.

| Sample | Abs Sc | N | R/Å | $2\sigma^2/Å^2$ | $E_f$/eV | $R_{factor}$ |
|---|---|---|---|---|---|---|
| Pd/CuClP 150° C. | Pd-Cl | 4.2 (1) | 2.322 (5) | 0.0028 (4) | 5.2 (7) | 0.007 |
| | Pd-Pd | 0.3 (2) | 2.76 (3) | 0.003 (3) | | |
| Pd/CuClP 175° C. | Pd-Cl | 3.2 (3) | 2.35 (1) | 0.003 (1) | 4 (2) | 0.041 |
| | Pd-Pd | 0.9 (4) | 2.77 (3) | 0.003 (2) | | |
| Pd/CuClP 200° C. | Pd-Cl | 3.4 (3) | 2.35 (1) | 0.0027 (7) | 13 (1) | 0.025 |
| | Pd-Pd | 0.9 (4) | 2.77 (2) | 0.002 (2) | | |

Pd sample-$S_0^2$ = 0.82 as deduced by PdCl$_2$ standard; Fit range 3 < k < 12, 1 < R < 3;
# of independent points = 11.

XAS was used to probe the coordination geometry and local structural environment of the active sites with a view to gaining a better understanding on nanoparticle formation and extrusion, with progressive increase in activation temperatures. Concurrent trends with the XPS are exhibited in both the EXAFS (FIG. 6B) and XANES (FIG. 6A) data of the Pt/CuClP material, with evident progressive reduction of the $[PtCl_4]^{2-}$ precursor species across the bulk of the sample. FIG. 6B demonstrates the significant decrease in contribution from Pt—Cl neighboring atoms with a concurrent increase in Pt—Pt neighbors as a function of activation temperature. Analogously, due to the direct relationship between the white-line intensity of the $L_3$-edge and the number of unoccupied Pt 5d states, the diminishing white line energies displayed in FIG. 6A suggest that the Pt species are approaching the metallic state with progressive increase in activation temperature.

Figure 9:
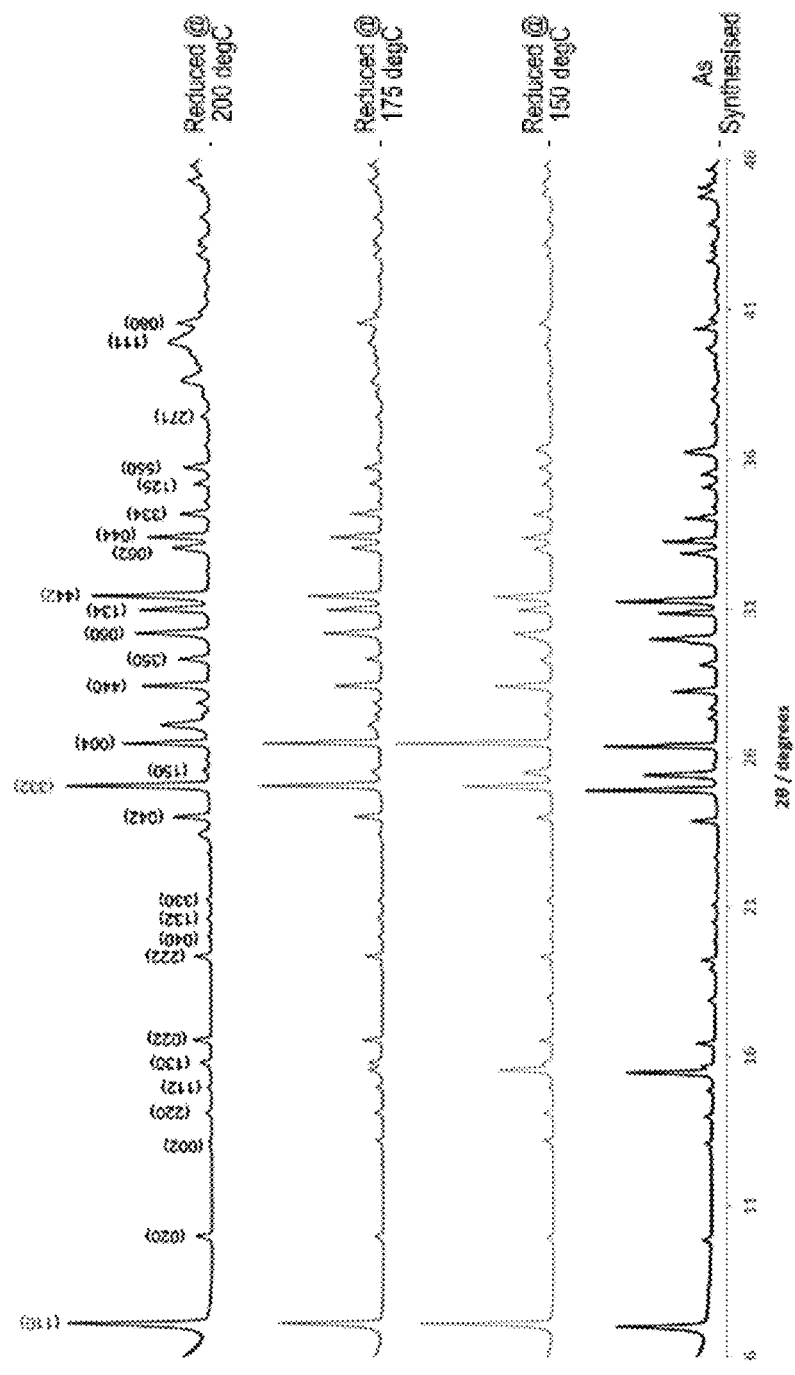
FIG. 9 is related to Example 2 and illustrates indexed powdered X-ray diffraction of Pt/CuClP materials activated at different temperatures with the pre-activation, as-synthesized sample.

In addition, Table 1 shows that Pt—Pt bond lengths remain consistent with that expected of Pt nanoparticles above 2.4 nm (2.76 Å) and that the coordination numbers of the first shell Pt—Pt scattering path are also lower at 9.6(4) than would be expected of bulk Pt metal at 12. This indicates that an overwhelming majority of the $[PtCl_4]^{2-}$ precursor are reduced to their metallic state with increase in activation temperature, as evidenced by the drastic reduction in the average number of adjacent Cl atoms around the central Pt species. These observations juxtaposed with those of the Au and Pd systems highlight the ease of extrusion of $[PtCl_4]^{2-}$ species from the micropores, while corresponding powder X-ray diffraction (PXRD) data confirms the retention of the structural integrity of the surrounding framework architecture (FIG. 9). In the case of Pt, it is clear that the absence of discrete precursor anions within the pores is not detrimental to the overall stability of the microporous framework structure (FIG. 9). This is in contrast to that of the Pd/CuClP catalyst (FIG. 12) where, at temperatures above 200° C., the structural integrity becomes susceptible to additional phase impurities and degradation of the framework. Without wishing to be held to any particular theory, it is believed that this could be indicative of stronger interactions between the discrete $[PdCl_4]^{2-}$ anions and the internal pores of the framework.

The Au XAS (FIG. 7) emphasizes that the $[AuCl_4]^-$ precursor requires much higher activation temperatures, despite the XPS showing surface species, with slightly reduced binding energies characteristic of nanoparticulate Au, being generated above 200° C. (FIG. 5). This suggests that although metallic Au species form on the surface of these materials at 200° C., higher temperatures and/or alternate activation conditions might be required to achieve comparable extrusions to the Pt catalyst.

Powder X-Ray Diffraction (PXRD)

X-Ray diffraction patterns were collected on a Bruker D2 Phaser diffractometer. FIG. 9 provides indexed PXRD spectra of the Pt/CuClP materials activated at different temperatures with the pre-activation, as-synthesized sample for comparison demonstrating both the structural integrity of the material at the various activation temperatures and a broad signal at 40° assigned to the metallic Pt (111) reflection. Additionally the broad nature of the peak is indicative of small particle (nanoparticulate) size.

Figure 10:
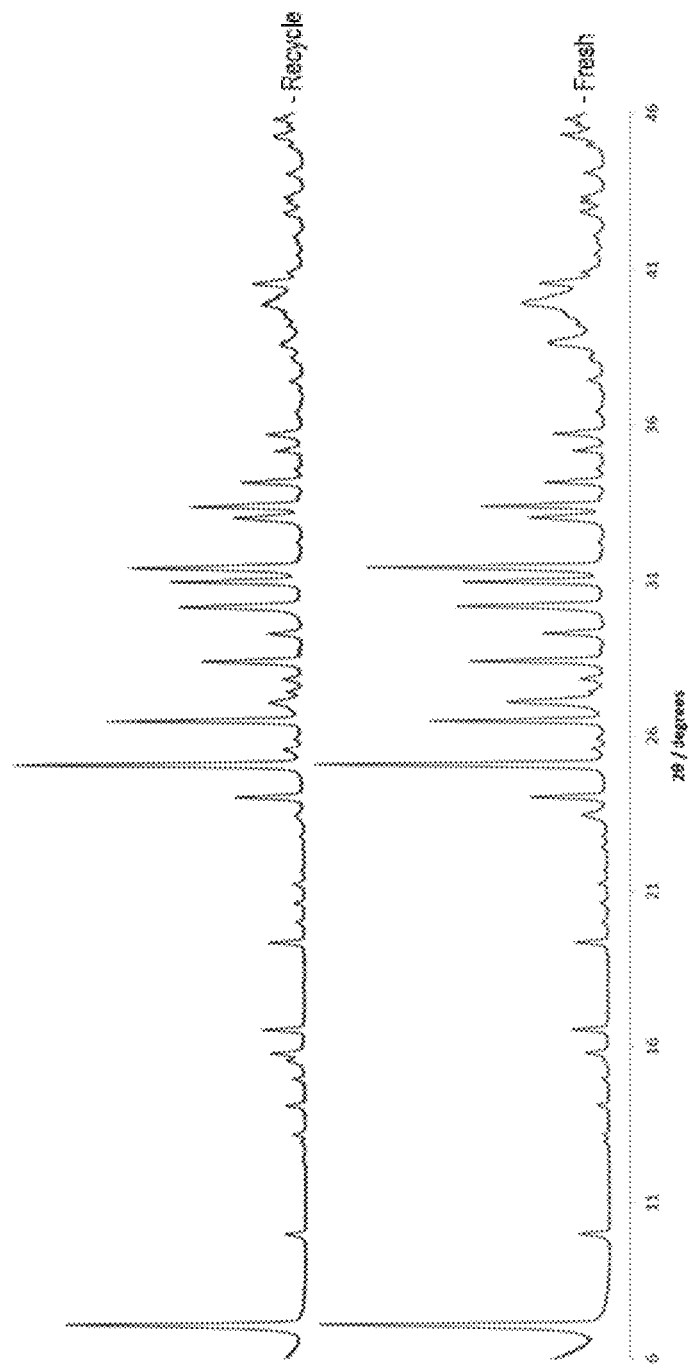
FIG. 10 is related to Example 2 and illustrates powdered X-ray diffraction of Pt/CuClP materials activated at 200° C. both before (fresh) and after catalysis (recycle) in the oxidation of KA-oil for 6 hr.

FIG. 10 provides PXRD spectra of the Pt/CuClP materials activated at 200° C. both before (fresh) and after catalysis (recycle) in the oxidation of KA-oil for 6 hr, signifying the robust nature and extended lifetime of these catalytic materials.

Figure 11:
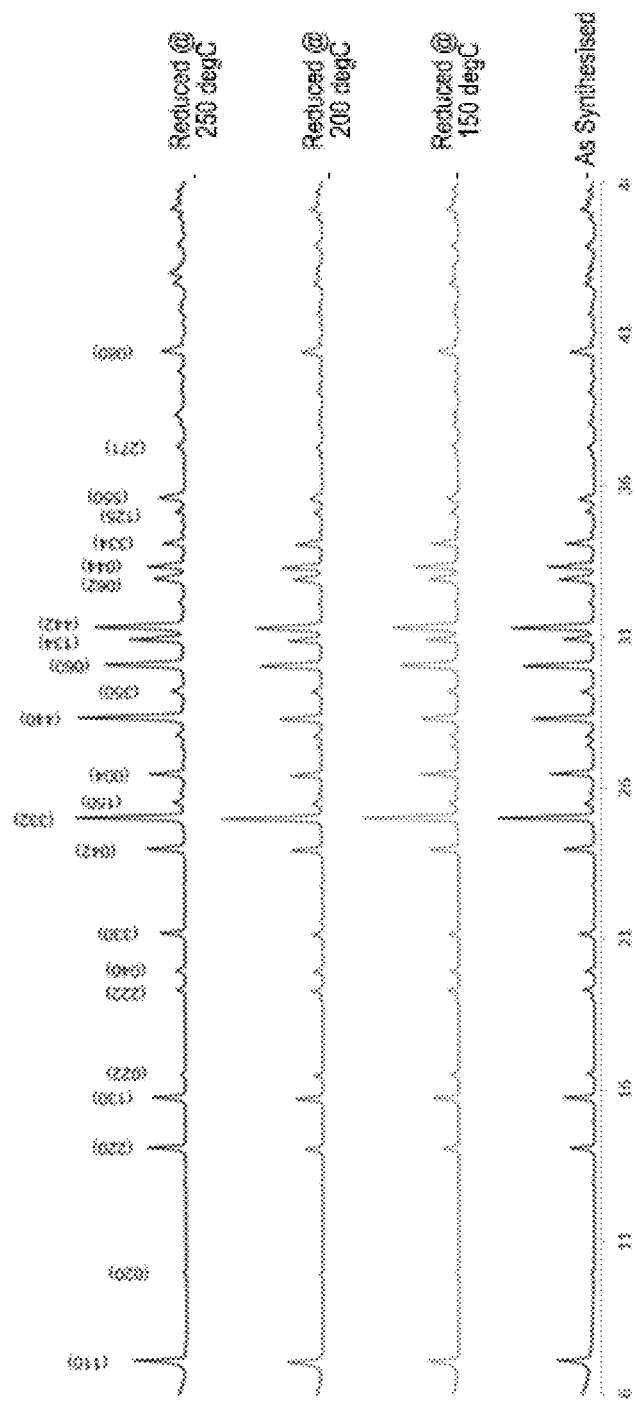
FIG. 11 is related to Example 2 and illustrated indexed powdered X-ray diffraction of Au/CuClP materials activated at different temperatures with the pre-activation, as-synthesized sample for comparison demonstrating the structural integrity of the material at the various activation temperatures.

FIG. 11 provides indexed PXRD spectra of the Au/CuClP materials activated at different temperatures with the pre-activation, as-synthesized sample for comparison demonstrating the structural integrity of the material at the various activation temperatures.

Figure 12:
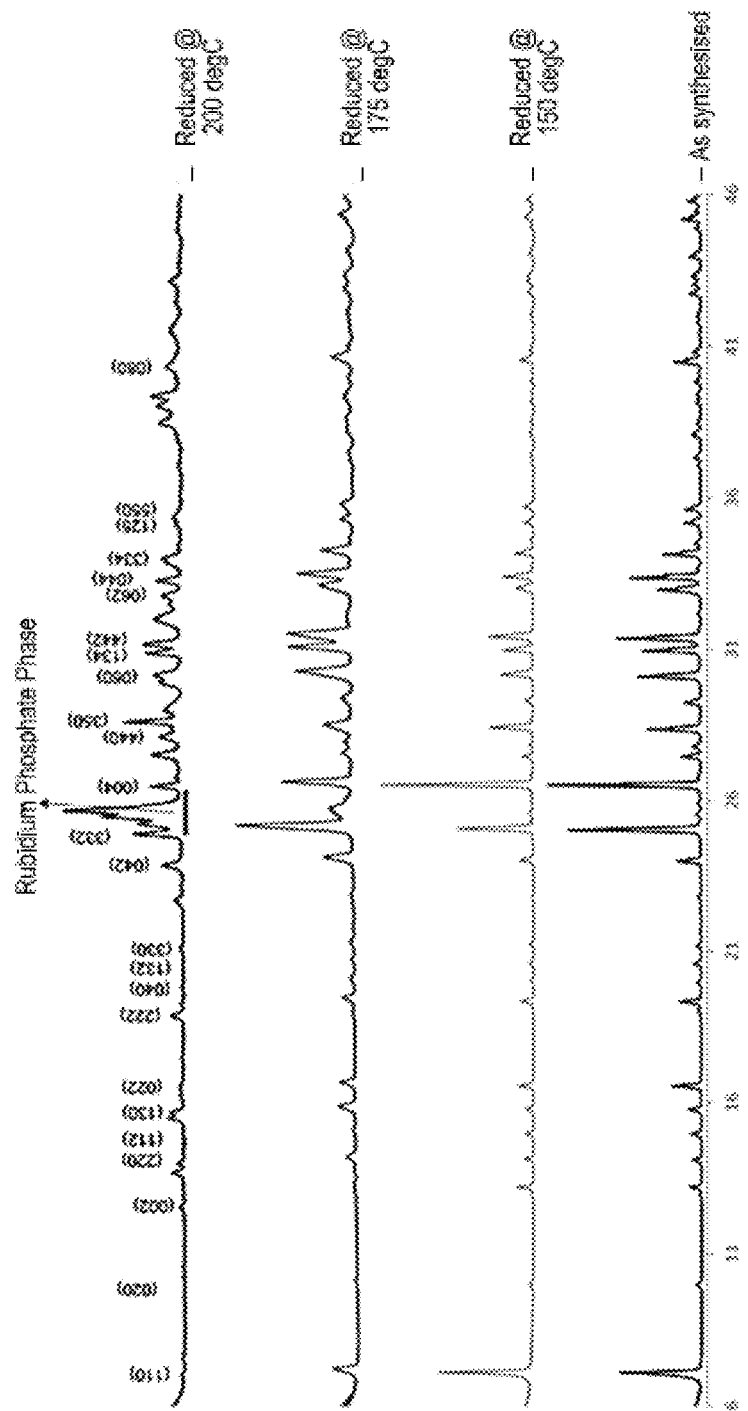
FIG. 12 is related to Example 2 and illustrates indexed powdered X-ray diffraction of Pd/CuClP materials activated at different temperatures with the pre-activation, as-synthesized sample for comparison, demonstrating the structural integrity of the material up to 175° C. and then the introduction of additional rubidium phosphate phases at temperatures close to 200° C.
Figure 16A:
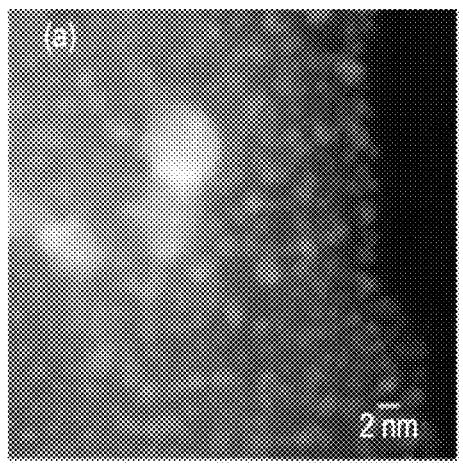
FIGS. 16A, 16B, 16C, 16D, 16E, and 16F are related to Example 2 and illustrate ADF AC-STEM images of the respective nanoparticle (NP)-framework materials activated at 200° C.
Figure 16B:
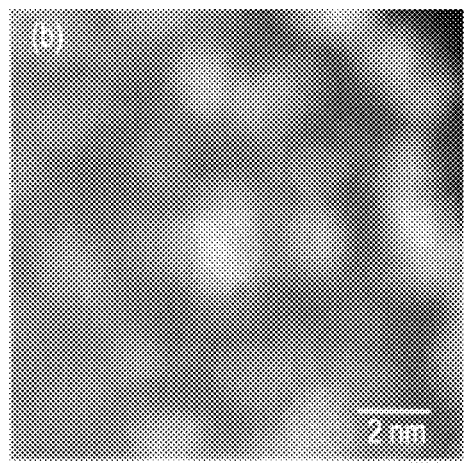
Figure 16C:
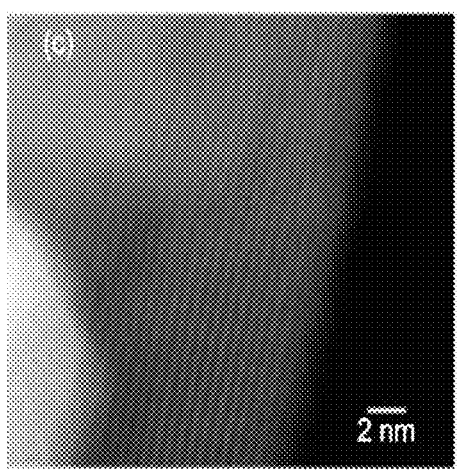
Figure 16D:
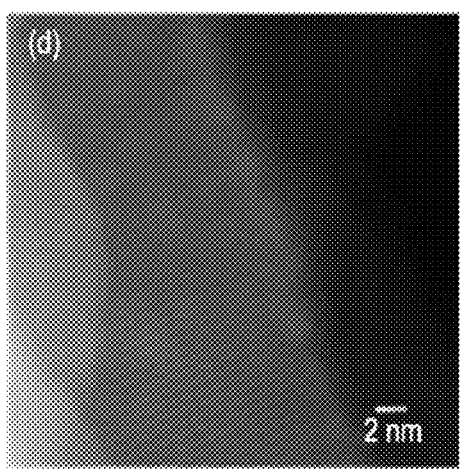
Figure 16E:
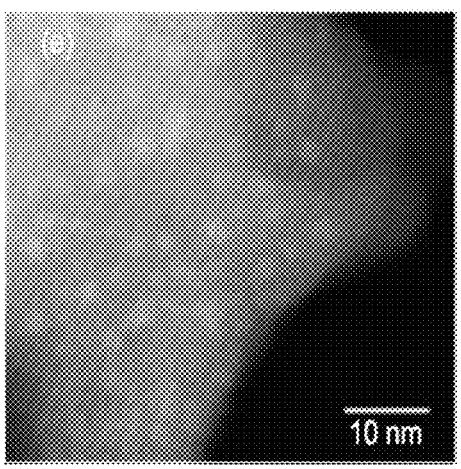
Figure 16F:
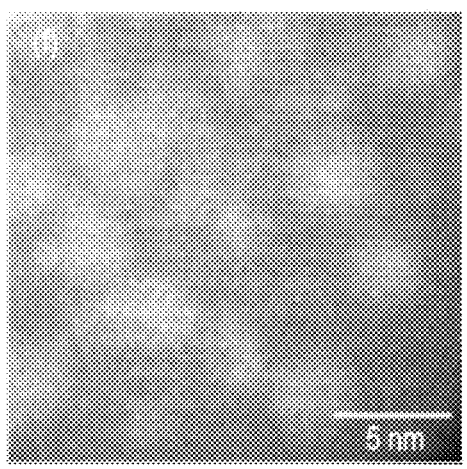

FIG. 12 provides indexed PXRD spectra of the Pd/CuClP materials activated at different temperatures with the pre-activation, as-synthesized sample for comparison, demonstrating the structural integrity of the material up to 175° C. and then the introduction of additional rubidium phosphate phases at temperatures close to 200° C.

Transmission Electron Microscopy (TEM)

Aberration-corrected TEM was performed on an FEI Titan[3] 80-300 (S)TEM equipped with a CEOS CESCOR aberration corrector in the probe forming lens. The Titan was operated at 80 or 300 kV, employing annular dark-field (ADF) aberration-corrected scanning TEM (AC-STEM) as the primary investigative technique. Samples were prepared for the STEM analysis by dusting the dry powder onto standard copper TEM support grids with holey carbon support film. Between analyses, samples were stored in a vacuum desiccator with anhydrous calcium sulfate desiccant. Under various combinations of electron beam current, dwell time and pixel size (magnification), and at both 80 and 300 kV, all samples were found to be highly susceptible to beam-induced damage. Considerable care was therefore taken to obtain representative images before overwhelming beam-induced modification of the samples occurred.

FIGS. 13-16 present various ADF AC-STEM images.

FIG. 13 presents ADF AC-STEM images of the Pt/CuClP material activated at 200° C. FIG. 13A shows nanoparticle formation across the framework (nanoparticle size in this area ~2-3 nm in diameter). FIGS. 13B and 13C present high-resolution images of the nanoparticles, in which the measured d-spacing's are consistent with nanocrystalline Pt. The crystalline integrity of the framework is also rendered visible, by virtue of the framework lattice planes containing heavy-metal atoms.

FIG. 14 presents ADF AC-STEM images of the Pd/CuClP material activated at 200° C. FIG. 14A shows the crystalline structure of the framework rendered visible by the framework lattice planes containing heavy metal atoms. Here no nanoparticle formation is observed. FIGS. 14B and 14C show limited nanoparticle formation, with a suggestion of higher propensity to form on the surface of the support, as highlighted in FIG. 14C.

FIG. 15 presents ADF AC-STEM images of the Au/CuClP material activated at 200° C. Nanoparticle formation is abundant across the framework, whose crystalline structure is rendered visible in both FIGS. 15A and 15B via heavy metal atom containing lattice planes of the framework. As shown in FIG. 15C, in addition to the small nanoparticles, significant larger nanoparticles are also present.

FIG. 16 presents ADF AC-STEM images of the respective nanoparticle-framework materials activated at 200° C. The crystalline structure of the framework is rendered visible via the lattice planes containing heavy atoms. FIGS. 16A and 16B show an abundance of Pt nanoparticles with $[PtCl_4]^{2-}$ precursor. FIGS. 16C and 16D show a paucity or limited Pd nanoparticle formation. FIGS. 16E and 16F show a prevalence of Au nanoparticles.

High-resolution studies, using AC-STEM, have shown in detail the abundant formation of nanocrystalline Pt nanoparticles (2-5 nm in diameter), which are well-dispersed on the copper chloropyrophosphate framework, whose crystalline integrity could also be visualized directly (FIGS. 13A-C, 16A, and 16B). In this regard it is apparent that the atomic number contrast and often 'direct interpretability' of ADF STEM imaging, combined with the high-spatial resolution enabled by AC optics, can yield significant insight into the crystallographic structures of both the extruded nanoparticles and the microporous framework. The much more limited nanoparticle formation in the Pd/CuClP system is also readily apparent from AC-STEM, as exemplified in FIGS. 14A-C, 16C, and 16D. Complementary compositional studies using STEM-EDXS also confirmed the well-defined nature of the Pt/CuClP and Pd/CuClP systems, with abundance and paucity of nanoparticles, respectively (FIGS. 15A and 15B).

Energy-Dispersive X-Ray Spectroscopy (EDXS)

EDXS was performed on an FEI Tecnai Osiris 80-200 (S)TEM operated at 80 kV, equipped with an FEI Super-X EDXS system. Spectral processing was performed using the FEI TIA and HyperSpy (http://hyperspy.org) software packages.

Figure 17:
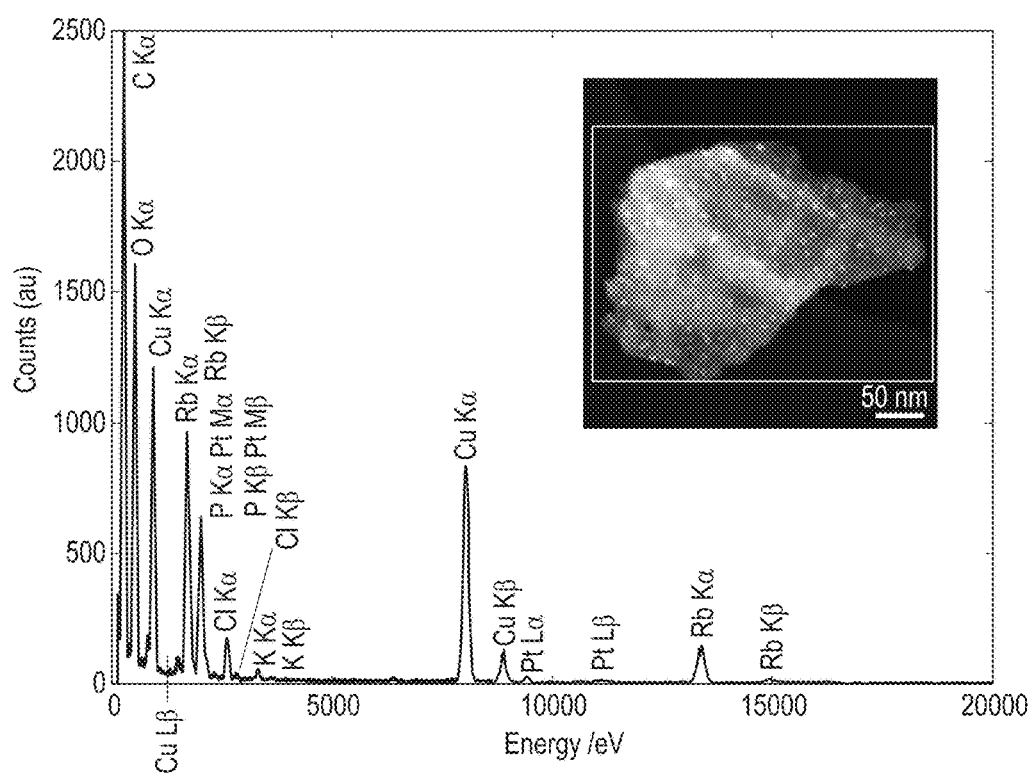
FIG. 17 is related to Example 2 and provides an EDXS spectra for the Pt/CuClP material activated at 200° C.
Figure 18:
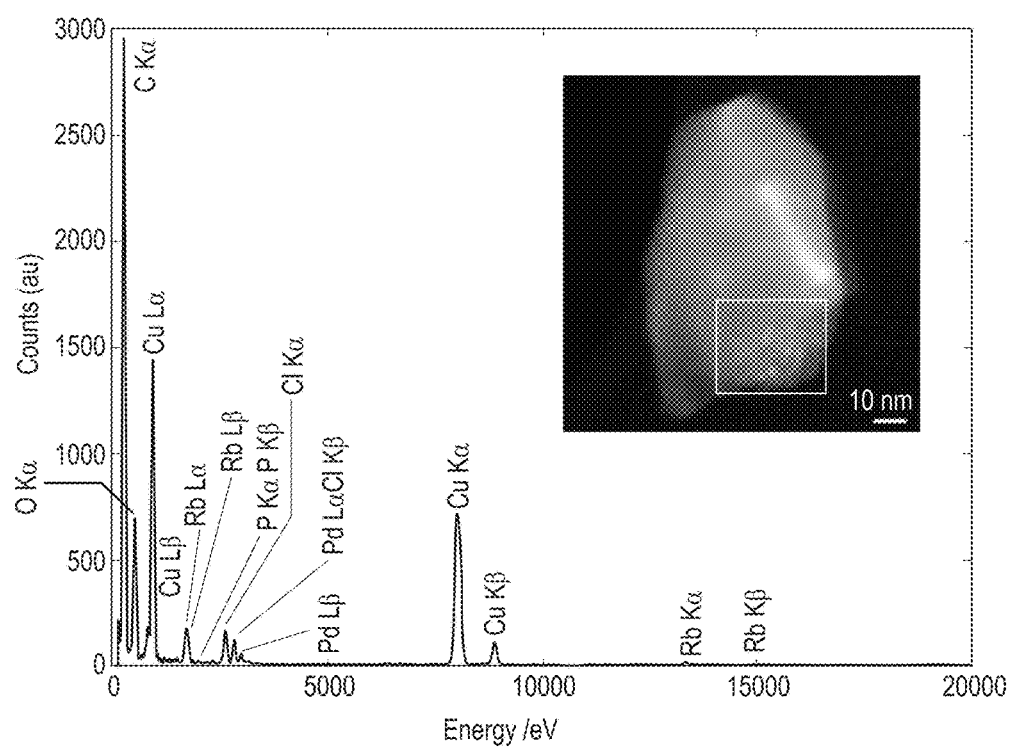
FIG. 18 is related to Example 2 and provides an EDXS spectra for the Pd/CuClP material activated at 200° C.
Figure 19:
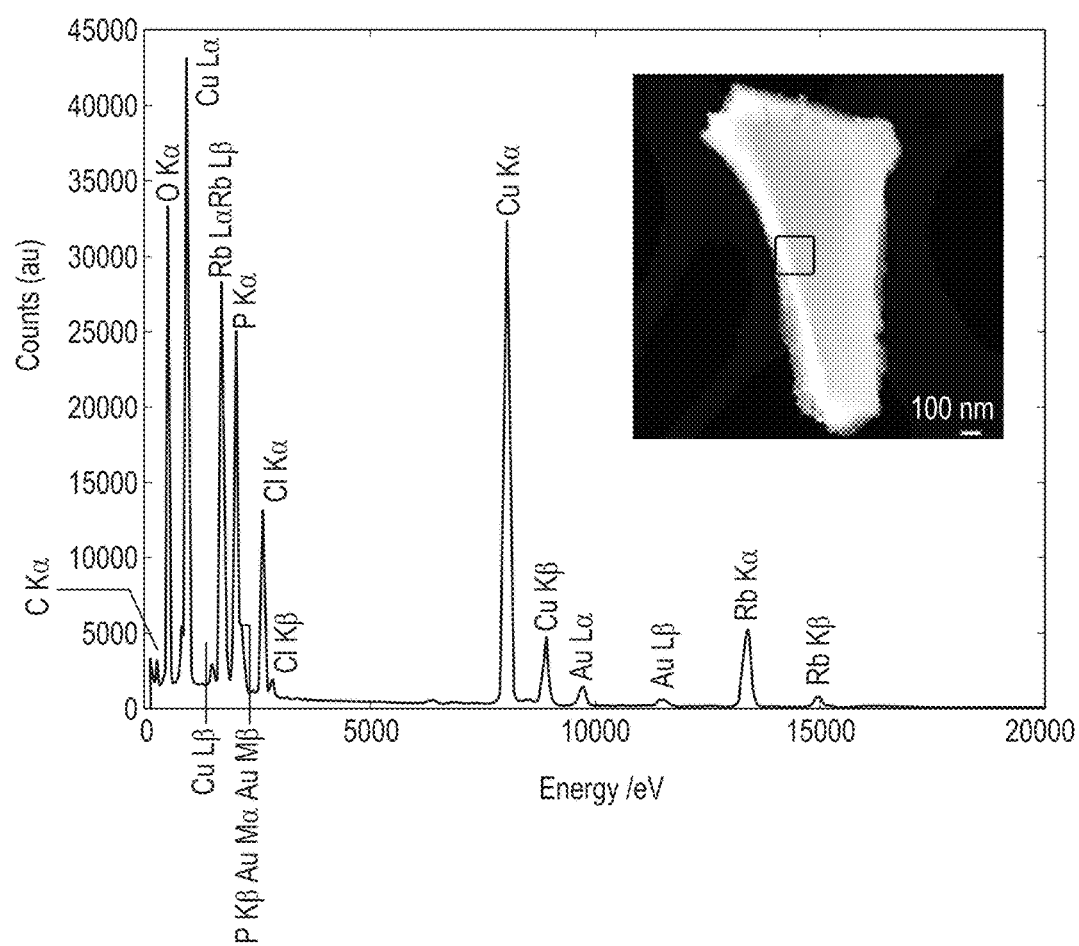
FIG. 19 is related to Example 2 and provides an EDXS spectra for the Au/CuClP material activated at 200° C.

The results are provided in FIGS. 17-19. For each figure, the area analyzed is indicated by the box in the inset ADF-STEM image. FIG. 17 provides an EDXS spectra for the Pt/CuClP material activated at 200° C. FIG. 18 provides an EDXS spectra for the Pd/CuClP material activated at 200° C. FIG. 19 provides an EDXS spectra for the Au/CuClP material activated at 200° C.

To verify overall composition, for all samples, EDX spectra were acquired and integrated from large regions across the micron-sized as well as smaller fragments of the samples. Characteristic regions of the samples typically showed presence of the expected constituent elements (viz. Pt, Pd or Au and Cu, Rb, Cl, O, P), as seen in the example spectra of FIGS. 17-19. Some (usually small in size and prevalence) fragments showed presence of F, Ca, or Si impurities and/or absence of expected constituent elements, which may be remnants from the synthesis process, contamination during synthesis, sample storage or TEM sample preparation, or the result of segregation over time.

The potentially more complex phenomena in the Au/CuClP system (as seen from the EXAFS) was also systematically investigated in AC-STEM and STEM-EDXS studies, including samples activated at different temperatures. As shown in FIGS. 15, 16E, 16F, and 37, regions of extensive well-defined small nanoparticle formation could be observed for the Au/CuClP system, even when the sample was activated at 200° C. (analogous to the Pt/CuClP). Consistent with the XPS studies, these would appear to predominate at thin or surface regions of the framework. Further, STEM and spatially resolved STEM-EDXS elemental mapping also indicates the potential for Au/Cu alloying or joint extrusion.

By employing a combination of complimentary structural, spectroscopic and high-resolution microscopy techniques, we have contrasted the varying degrees of nanoparticle formation and the superior properties of the $[PtCl_4]^{2-}$ precursor to yield well-defined, isolated nanoparticles (predominantly 2-3 nm) within microporous framework architectures. The local structural environment, and the precise nature and location of these active sites, is exigent for their performance (approaching yields of >90% by adapting a 'closed-loop' system) in the aerobic oxidation of KA-oil, under continuous-flow conditions.

Figure 35:
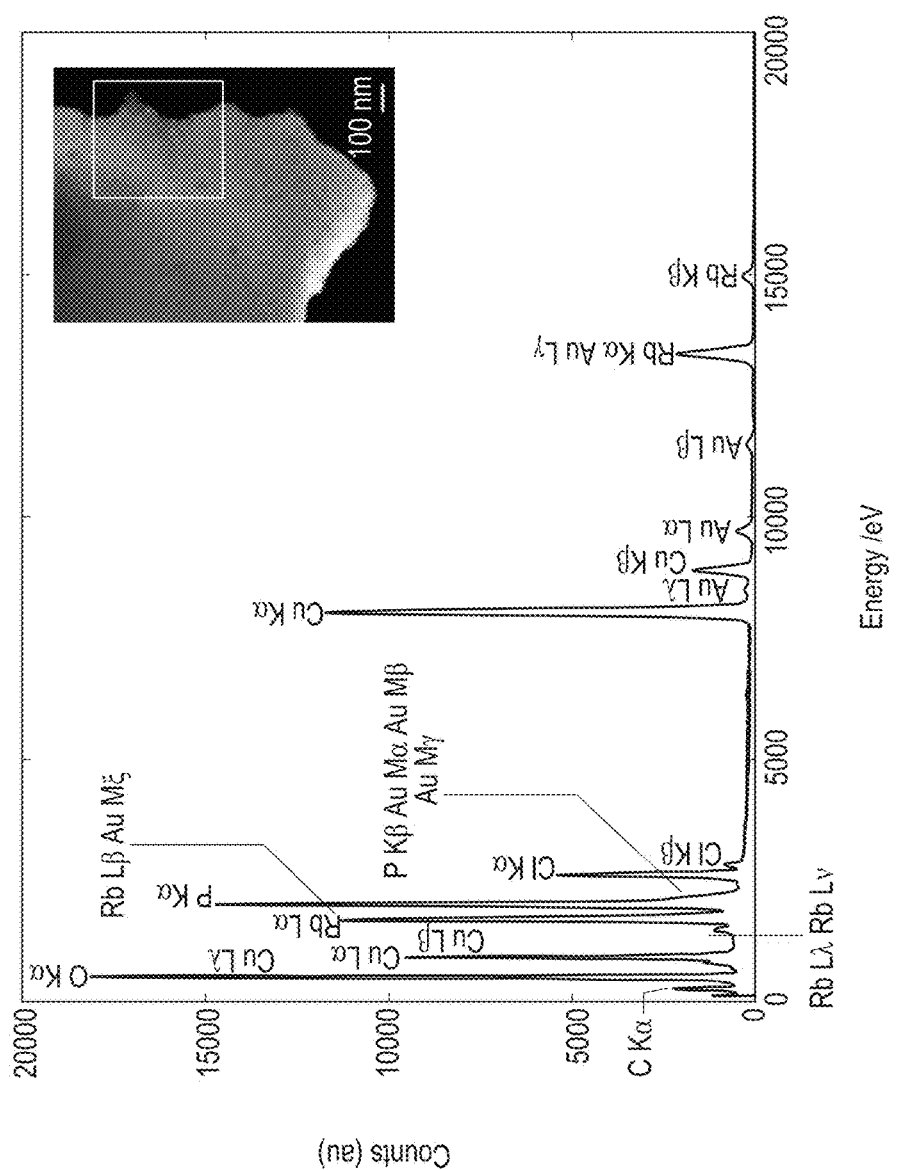
FIG. 35 is related to Example 2 and illustrates an EDXS spectra for the Au/CuClP material activated at 250° C.
Figure 36:
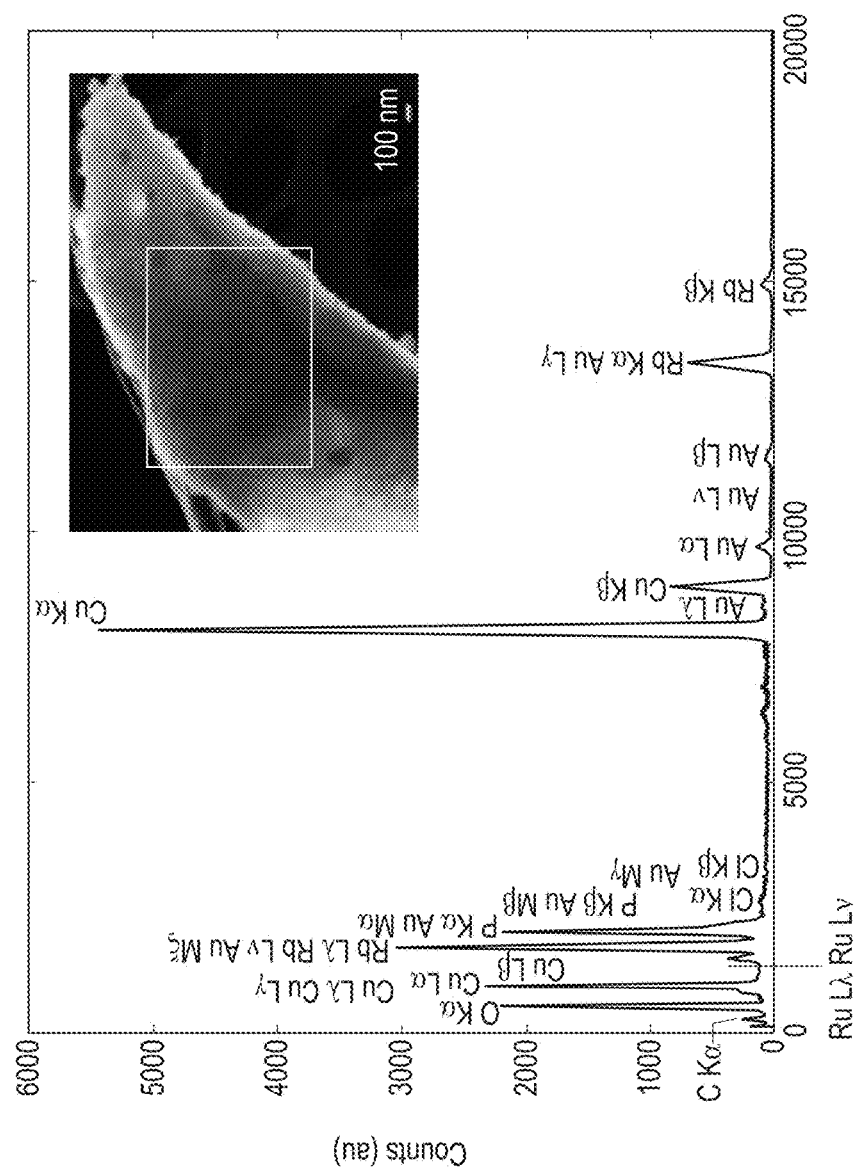
FIG. 36 is related to Example 2 and illustrates an EDXS spectra for the Au/CuClP material activated at 350° C.
Figures 37A, 37B, 37C, 37D:
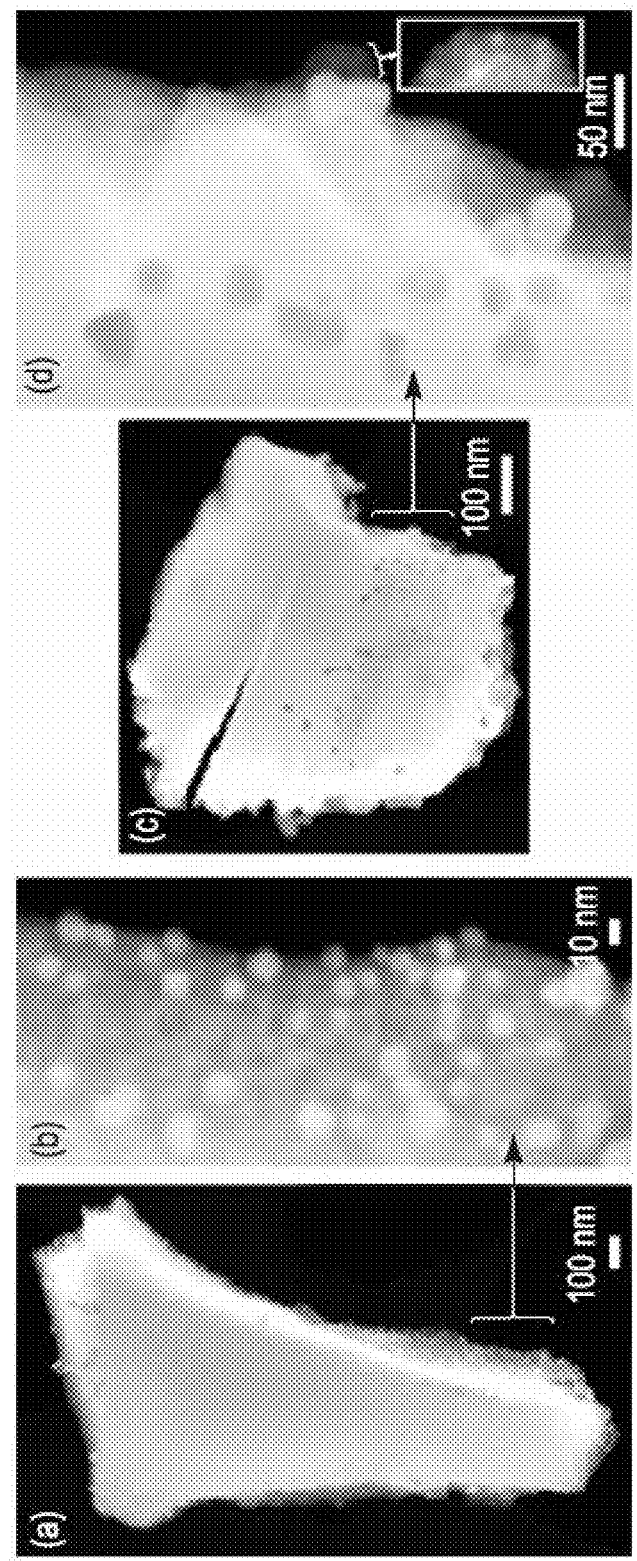
FIGS. 37A, 37B, 37C, and 37D are related to Example 2 and illustrate ADF-STEM images of the Au/CuClP material activated at 200° C.

To investigate the effects of different activation temperatures on the morphology and composition of the Au/CuClP materials, further STEM imaging and EDXS investigations were undertaken using the Tecnai Osiris. To ensure correct interpretation, note that some of the ADF images in this section show contrast inversion at thicker regions of the sample and often at the larger nanoparticles. Elemental maps were obtained by integrating the area under the relevant X-ray peaks, using the HyperSpy software package (http://hyperspy.org), with the particular peaks chosen to minimize effects of peak overlap. As the samples were supported on Cu TEM grids, the Cu $L_\alpha$ rather than Cu $K_\alpha$ peak has been used for the Cu maps; the former being more representative of Cu in the sample itself. FIG. 35 illustrates an EDXS spectra for the Au/CuClP material activated at 250° C. FIG. 36 illustrates an EDXS spectra for the Au/CuClP material activated at 350° C. The area analysed for elemental content is indicated by the box in the inset ADF-STEM image.

FIGS. 37-39 illustrate ADF-STEM images of the Au/CuClP material activated at various temperatures. A combination of EDXS point spectra, line scans and spectrum images were performed to probe the chemical identity of the nanoparticles and distribution of elements within the framework. These confirmed the identity of smaller (2-5 nm) and larger (>10 nm) nanoparticles as dominantly Au, although some nanoparticles were found to be dominantly Cu, often concomitant with substantial agglomeration of elements from the framework.

FIGS. 37A-D illustrate ADF-STEM images of the Au/CuClP material activated at 200° C. Medium/small nanoparticle formation is visible at the periphery of the fragments of the sample, as highlighted in FIGS. 37B and 37D. A limited number of larger nanoparticles are visible, particularly in FIG. 37D, but the majority of the fragments of the sample show smooth intensity, indicative of a more pristine framework (compared to the strong mottled contrast and extensive nanoparticle formation seen in FIGS. 39B and 39D).

FIGS. 38A-E illustrate ADF and bright-field STEM images of the Au/CuClP material activated at 250° C. ADF images such as shown in FIGS. 38A, 38B, and 38D, and bright-field STEM images, such as shown in FIGS. 38C and 38E illustrate the morphology of the sample. In addition to abundant small nanoparticle formation, particularly illustrated in FIG. 38C, there is also considerable large nanoparticle formation. Variation in image contrast throughout the bulk of the framework. Without wishing to be held to any particular theory, this is believed to suggest morphological and compositional re-distributions as a result of the heat treatment process.

Figure 40A:
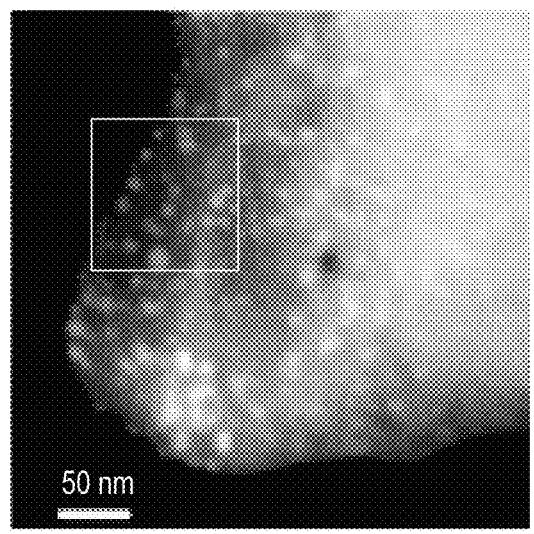
FIG. 40C is related to Example 2 and provides an EDXS spectrum for the small nanoparticles in FIGS. 40A-B.
FIG. 40D is related to Example 2 and provides elemental maps obtained from the EDXS spectrum of FIG. 40C.
Figure 40B:
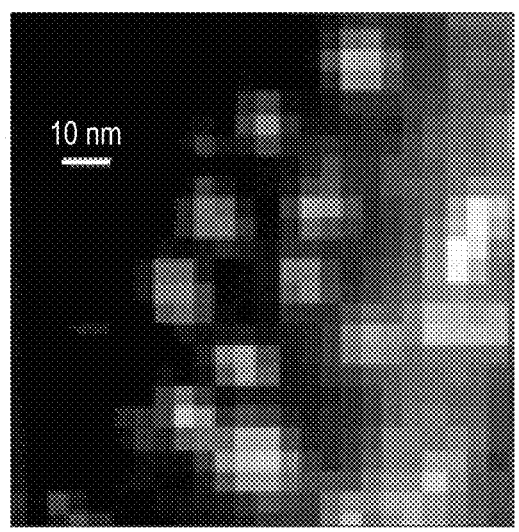
Figure 40C:
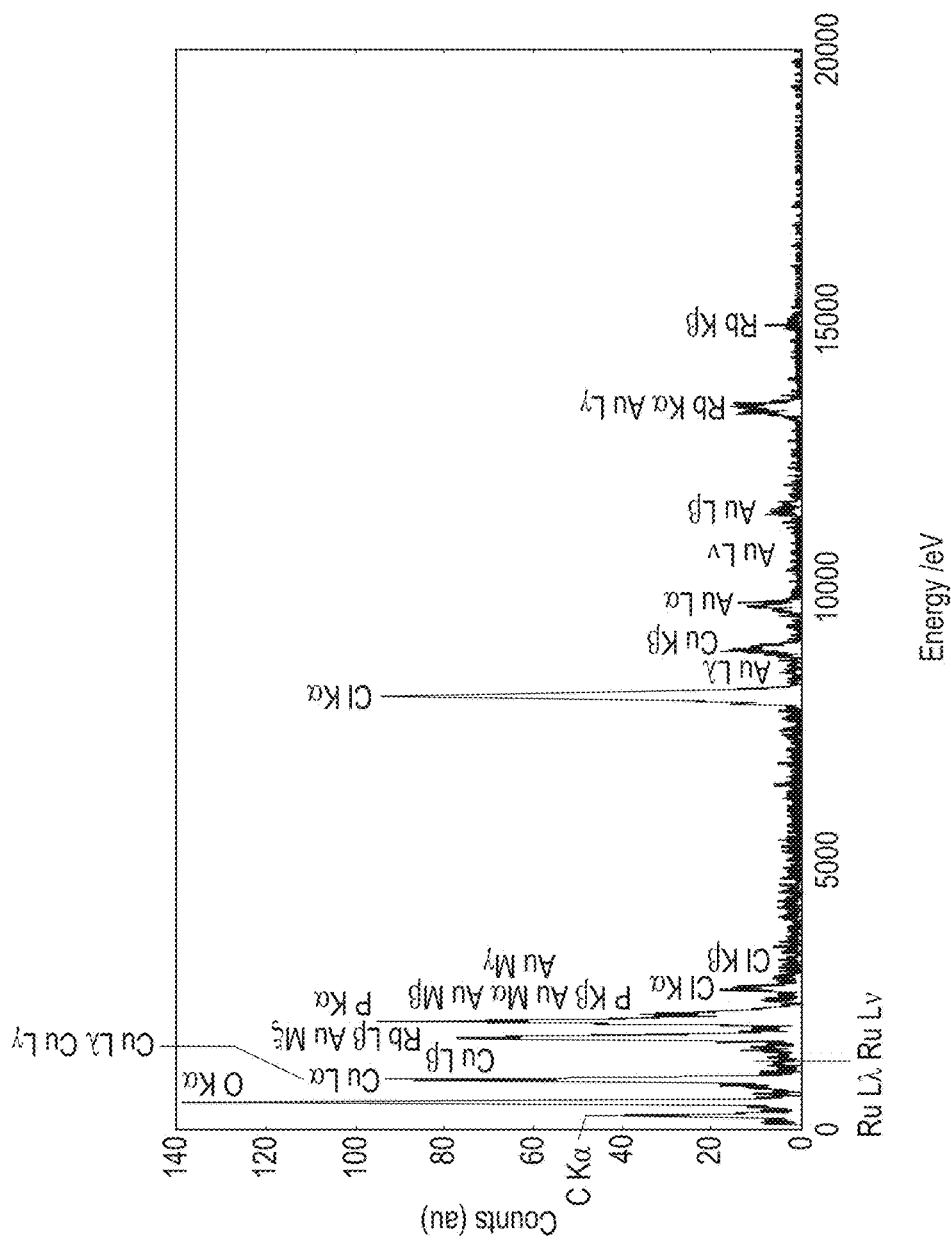
Figure 40D:
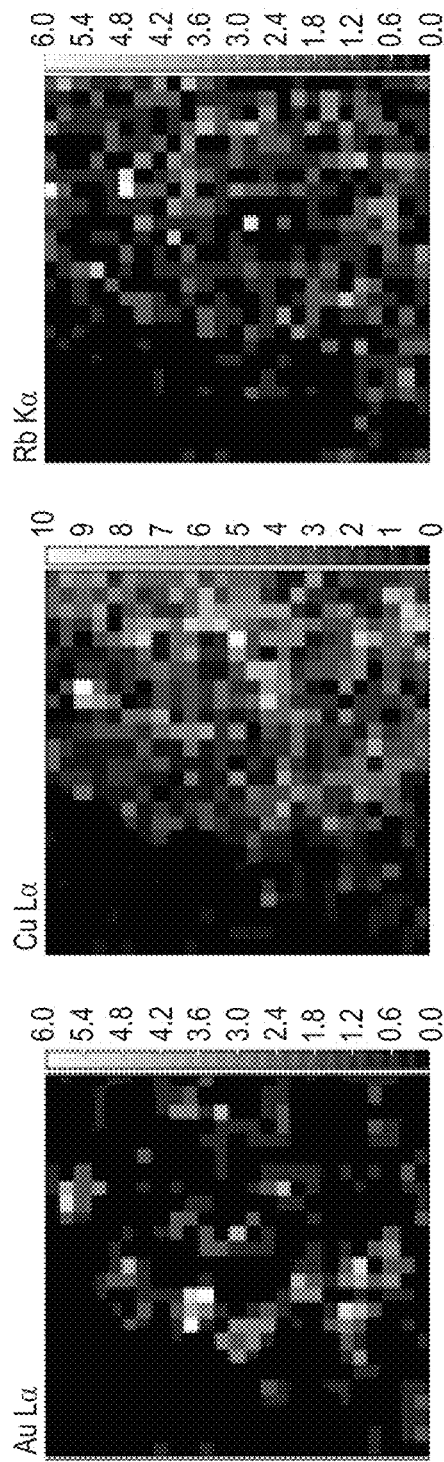
Figure 40D:
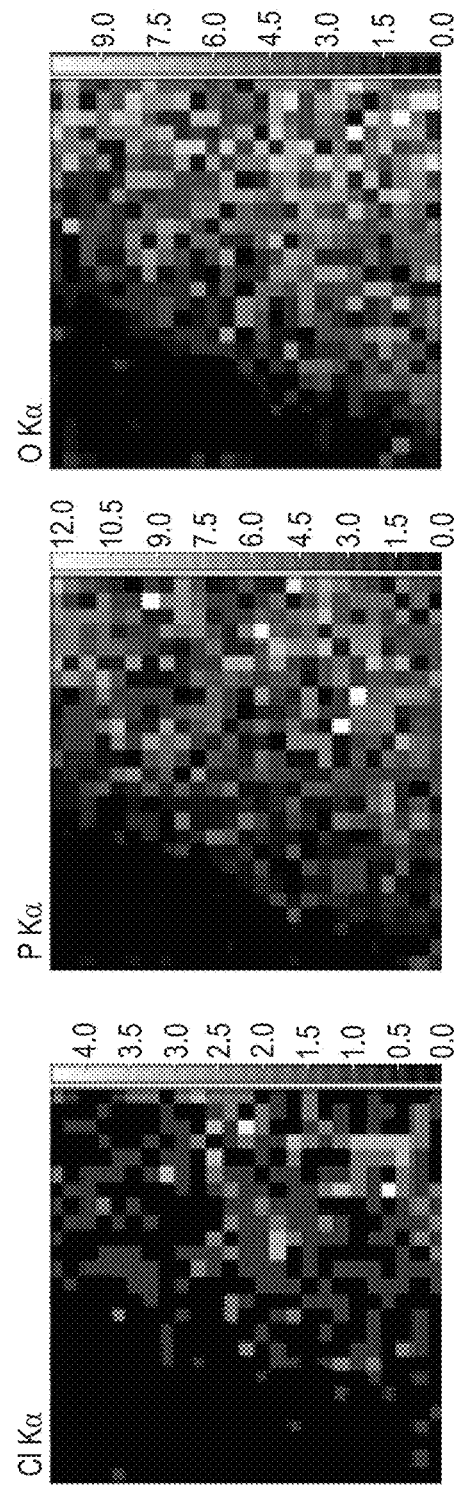
Figure 41A:
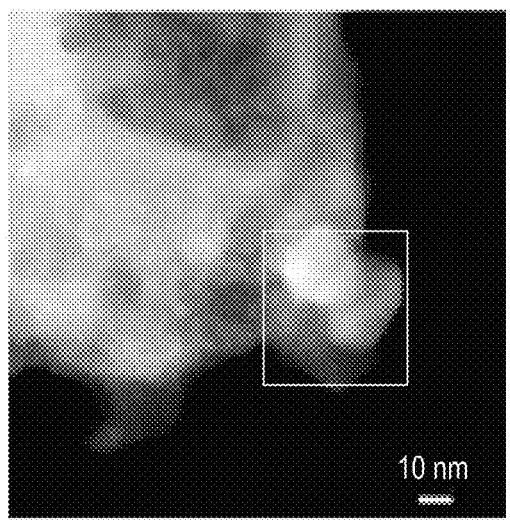
FIGS. 41A and 41B are related to Example 2 and illustrates ADF images of the large faceted nanoparticles in the Au/CuClP sample activated at 350° C.
Figure 41B:
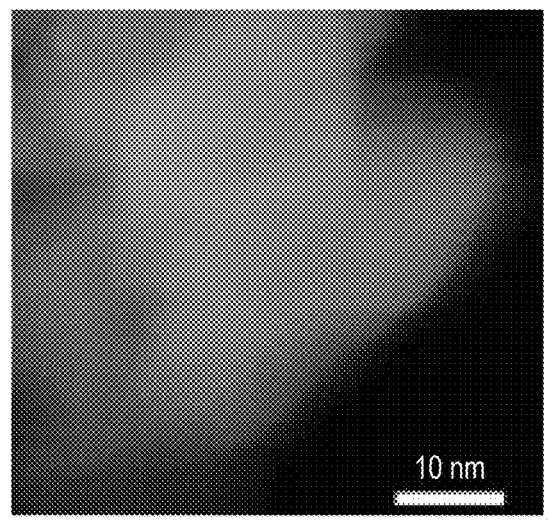
Figure 41C:
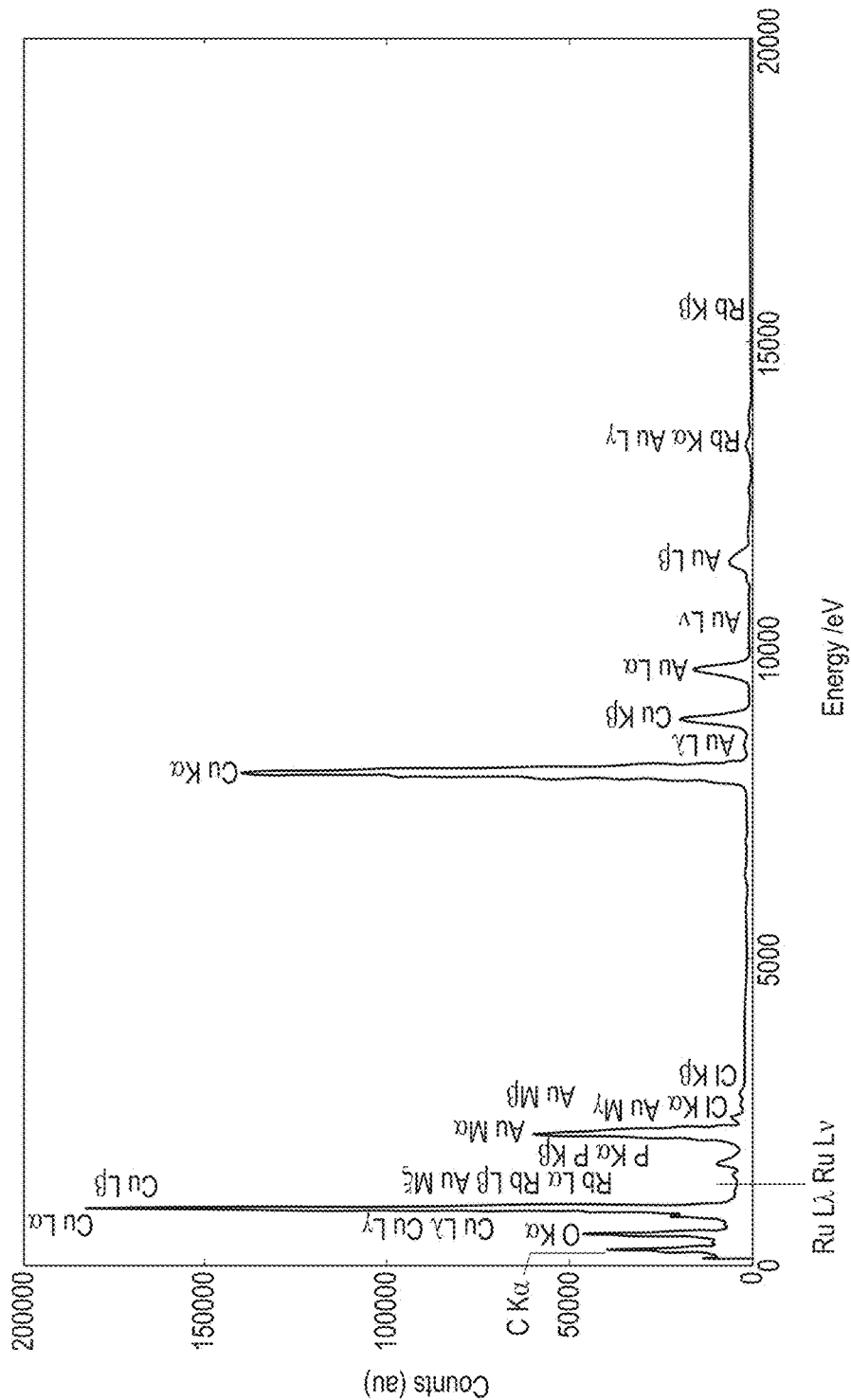
FIG. 41C is related to Example 2 and provides an EDXS spectrum for the large faceted nanoparticles in FIGS. 41A-B.
Figure 41D:
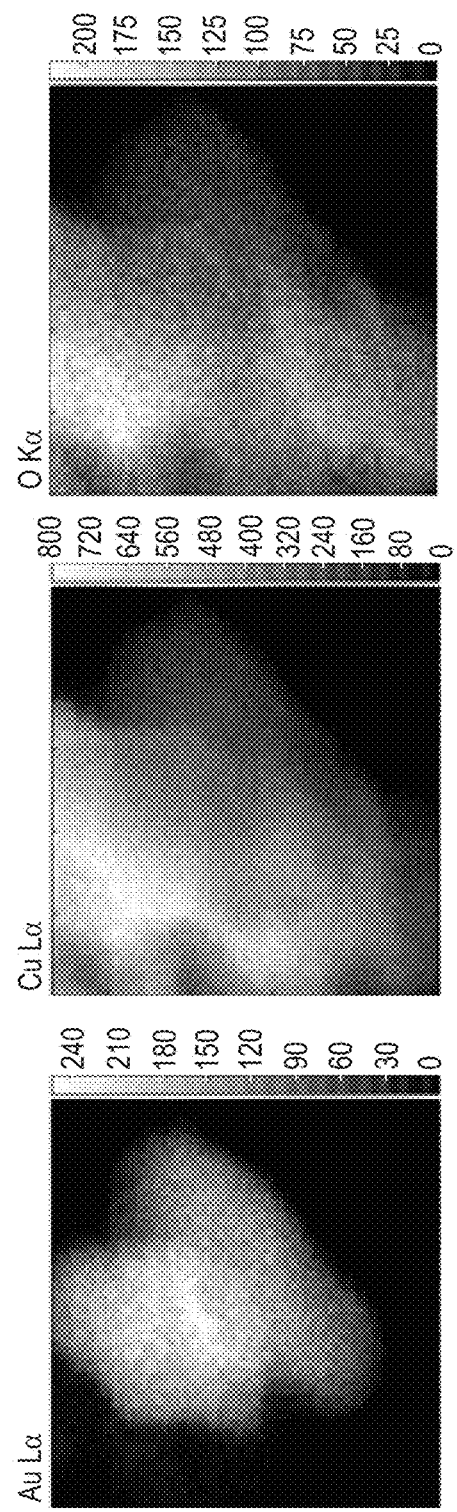
FIG. 41D is related to Example 2 and provides elemental maps obtained from the EDXS spectrum of FIG. 41C.

FIGS. 39A-E illustrate ADF-STEM images of the Au/CuClP material activated at 350° C. ADF-STEM images revealing the morphology of the Au/CuClP sample activated at 350° C. Extensive large nanoparticle formation and variation in image contrast throughout the bulk suggests substantial morphological and compositional re-distributions as a result of the heat treatment process FIG. 40 illustrates images of the small nanoparticles in the Au/CuClP sample activated at 250° C. FIG. 40A shows an ADF image of the region analysed prior to EDXS. FIG. 40B shows an ADF image acquired simultaneous to EDXS mapping. FIG. 40C illustrates an EDXS sum-spectrum, obtained by summing all spectra from the spectrum image. FIG. 40D illustrates elemental maps obtained from the spectrum image by peak integration. As illustrated in FIG. 40D, the spectrum image, acquired with a relatively short dwell time and coarse pixel size to minimise beam-induced modification of the sample, associates the Au signal with the nanoparticles, with the other elements distributed more evenly across the framework support.

FIG. 41 illustrates images of the large faceted nanoparticles in the Au/CuClP sample activated at 350° C. FIG. 41A shows an ADF image of the region analysed prior to EDXS. FIG. 41B shows an ADF image acquired simultaneous to EDXS mapping. FIG. 41C illustrates an EDXS sum-spectrum, obtained by summing all spectra from the spectrum image. FIG. 41D illustrates elemental maps obtained from the spectrum image by peak integration. As shown in FIG. 41D, even though significant spatial drift has occurred during the spectrum image acquisition, the spectrum image supports that the large faceted nanoparticles are Au, while the supporting framework is Cu rich. (Rb, P and Cl maps not shown here due to peak overlap and dominance of the Au signal in this spectrum image).

FIG. 42 illustrates images of the large nanoparticles and agglomerations in the framework support in the Au/CuClP sample activated at 350° C. FIG. 42A shows an ADF image of the region analysed prior to EDXS. FIG. 42B shows an ADF image acquired simultaneous to EDXS mapping. FIG.

Figure 42A:
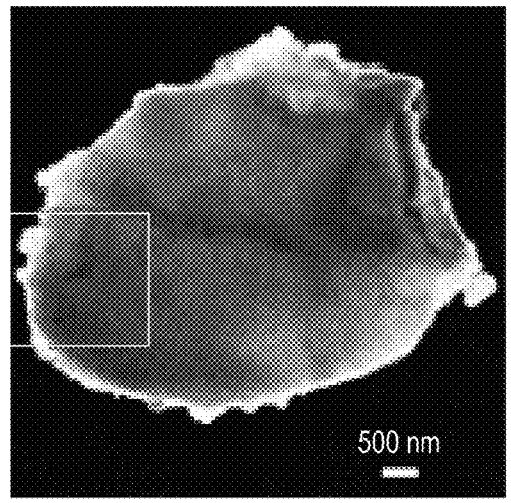
FIGS. 42A and 42B are related to Example 2 and illustrates ADF images of the large nanoparticles and agglomerations in the framework support in the Au/CuClP sample activated at 350° C.
Figure 42B:
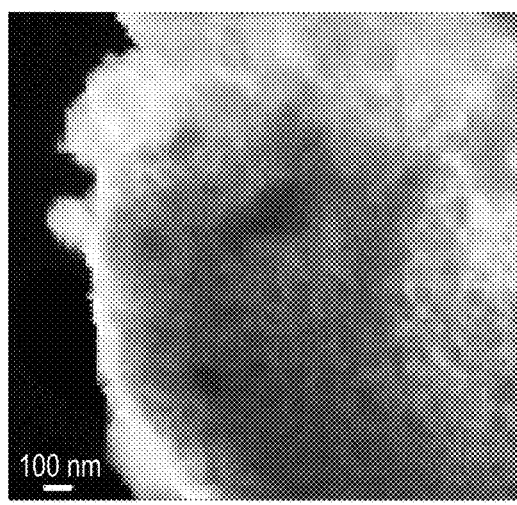
Figure 42C:
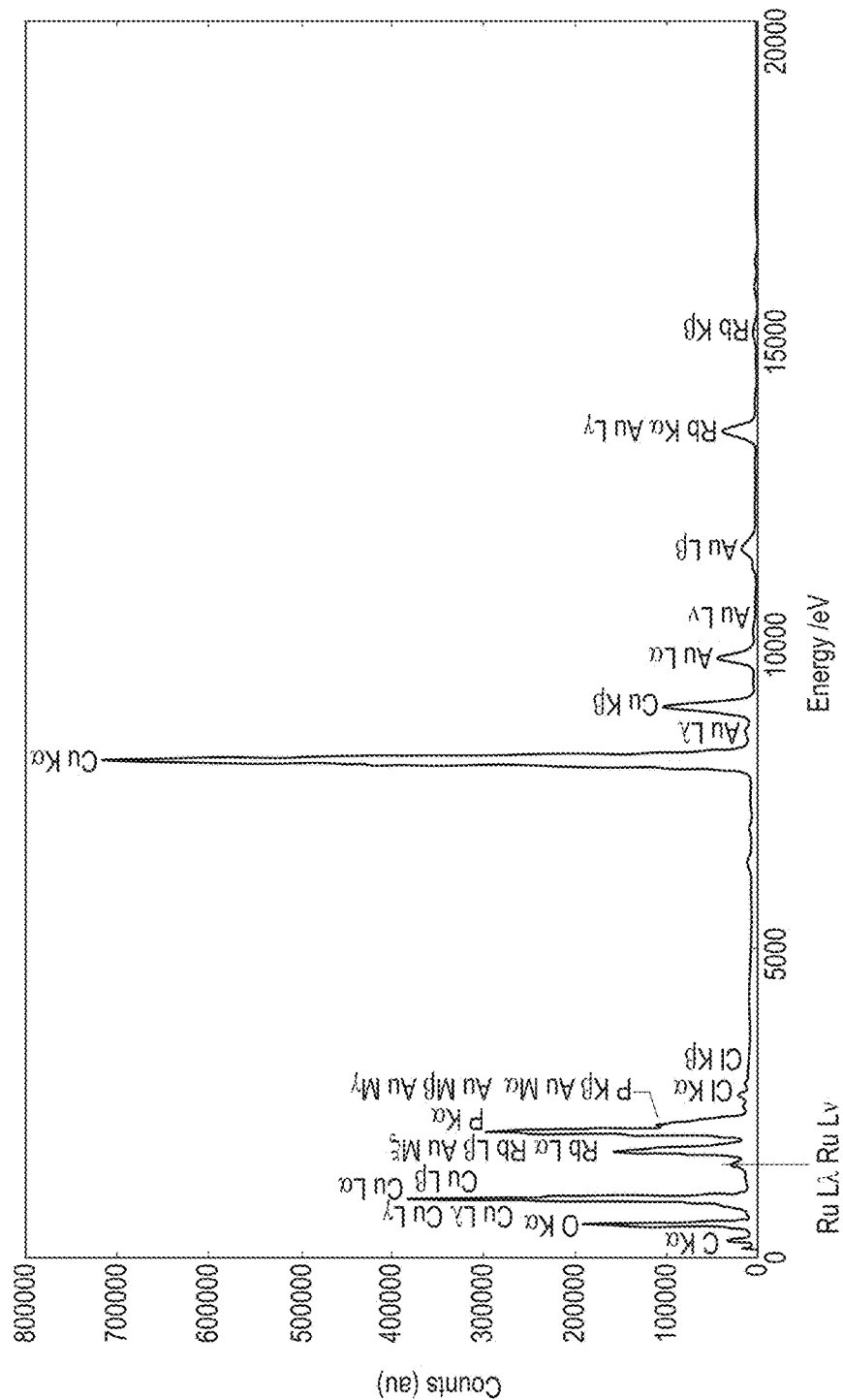
FIG. 42C is related to Example 2 and provides an EDXS spectrum for the large nanoparticles and agglomerations in the framework support in FIGS. 42A-B.
Figure 42D:
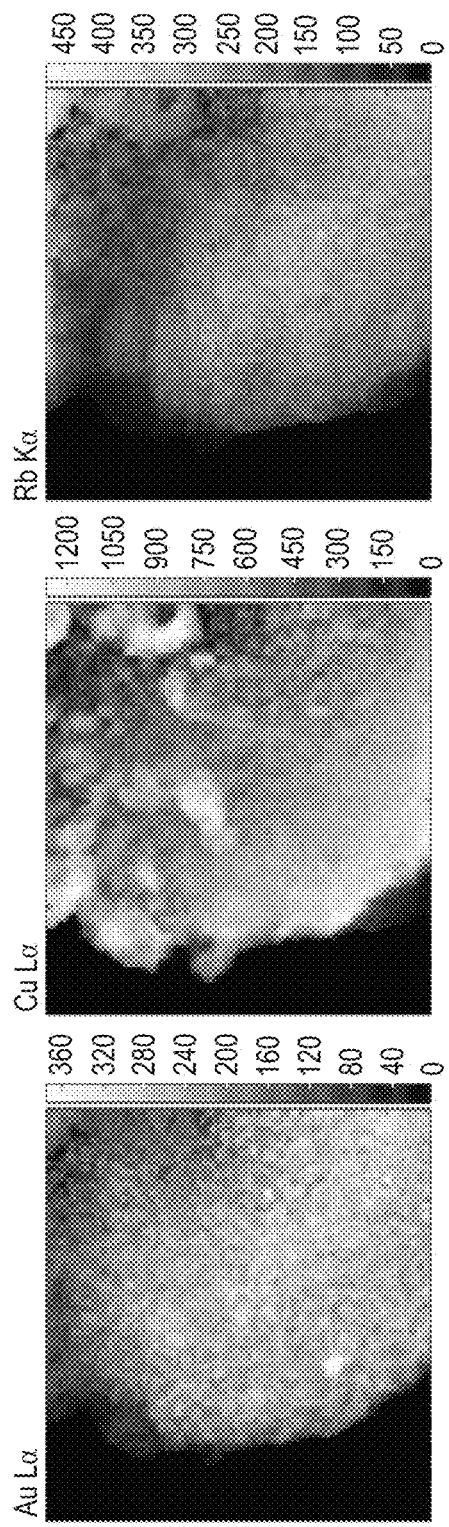
FIG. 42D is related to Example 2 and provides elemental maps obtained from the EDXS spectrum of FIG. 42C.
Figure 42D:
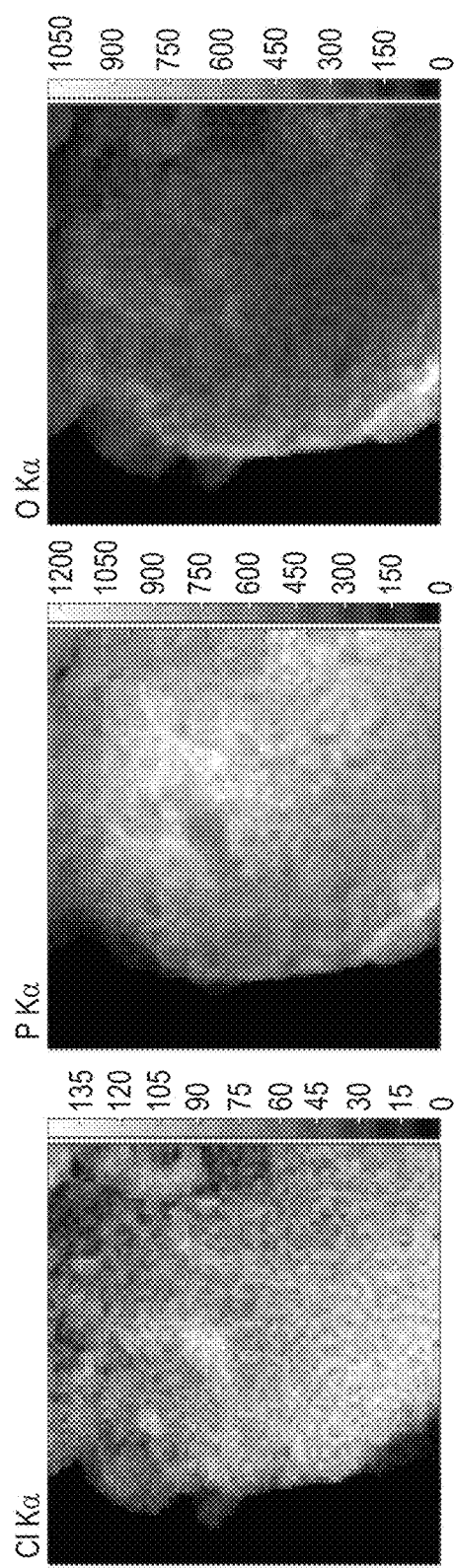
Figure 43:
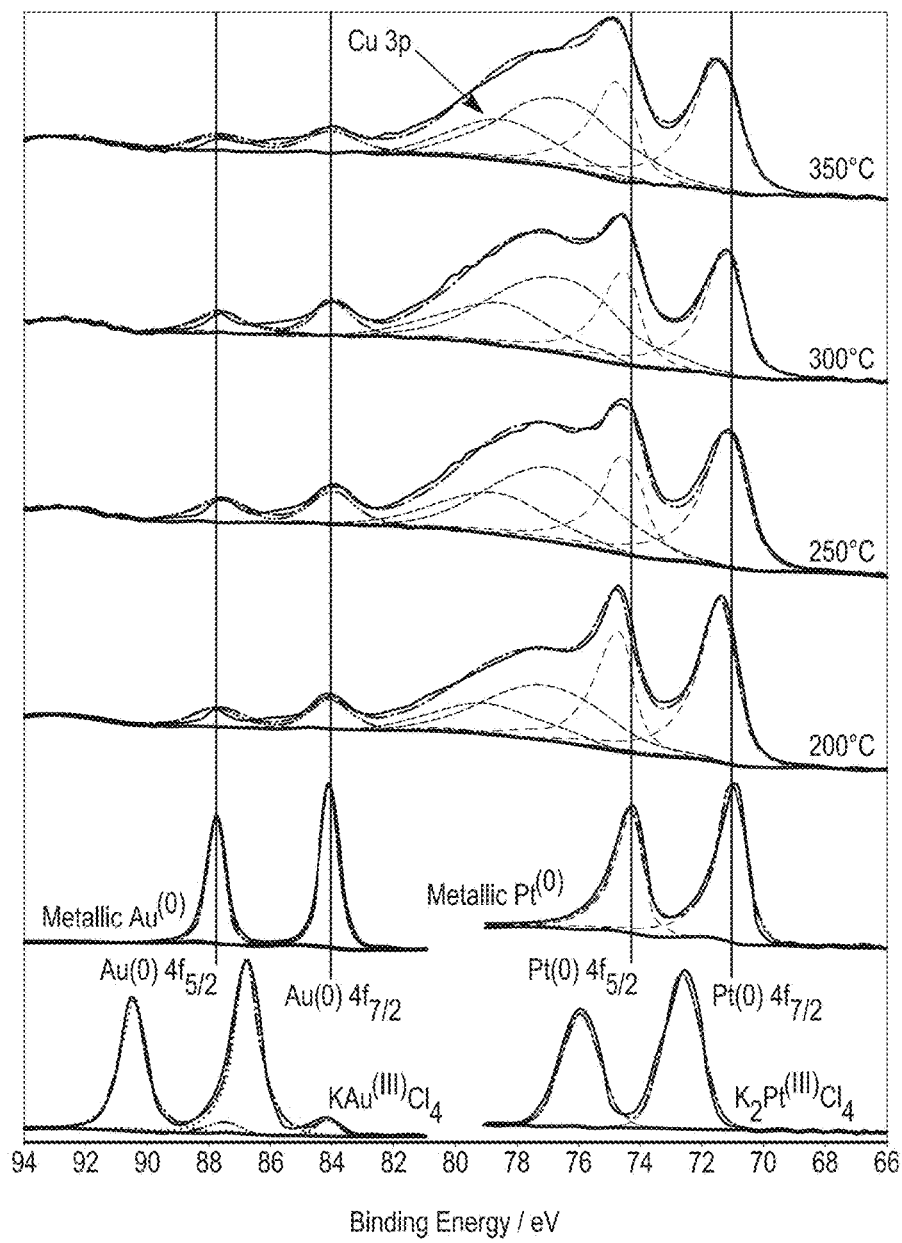
FIG. 43 is related to Example 4 and illustrates stacked XPS spectra, with data fits and appropriate reference samples, of exemplary AuPt/CuClP catalyst materials activated at different temperatures.
Figure 44A:
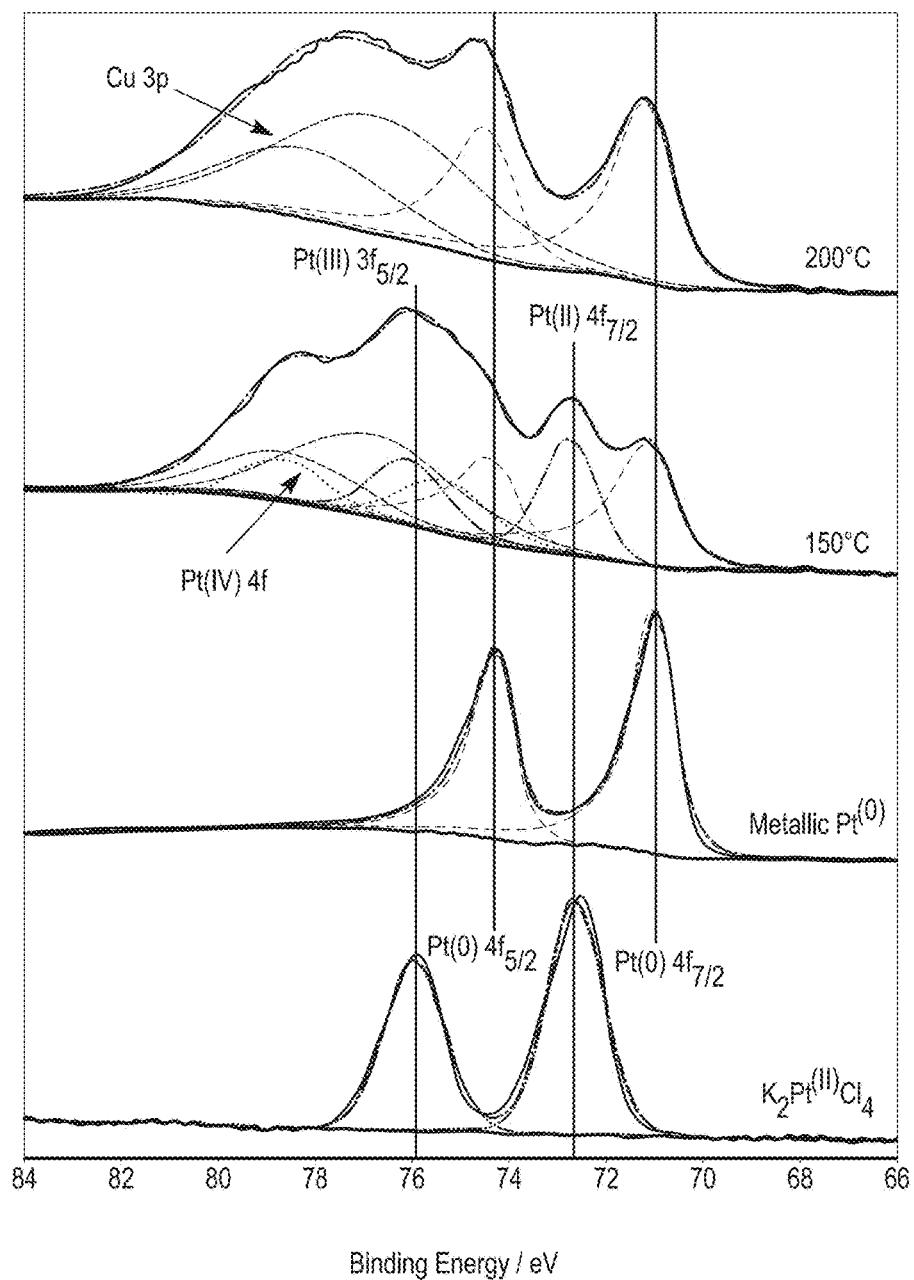
FIGS. 44A and 44B are related to Example 4 and illustrate stacked XPS spectra, with data fits and appropriate reference samples, of exemplary PtPd/CuClP catalyst materials activated at different temperatures.
Figure 44B:
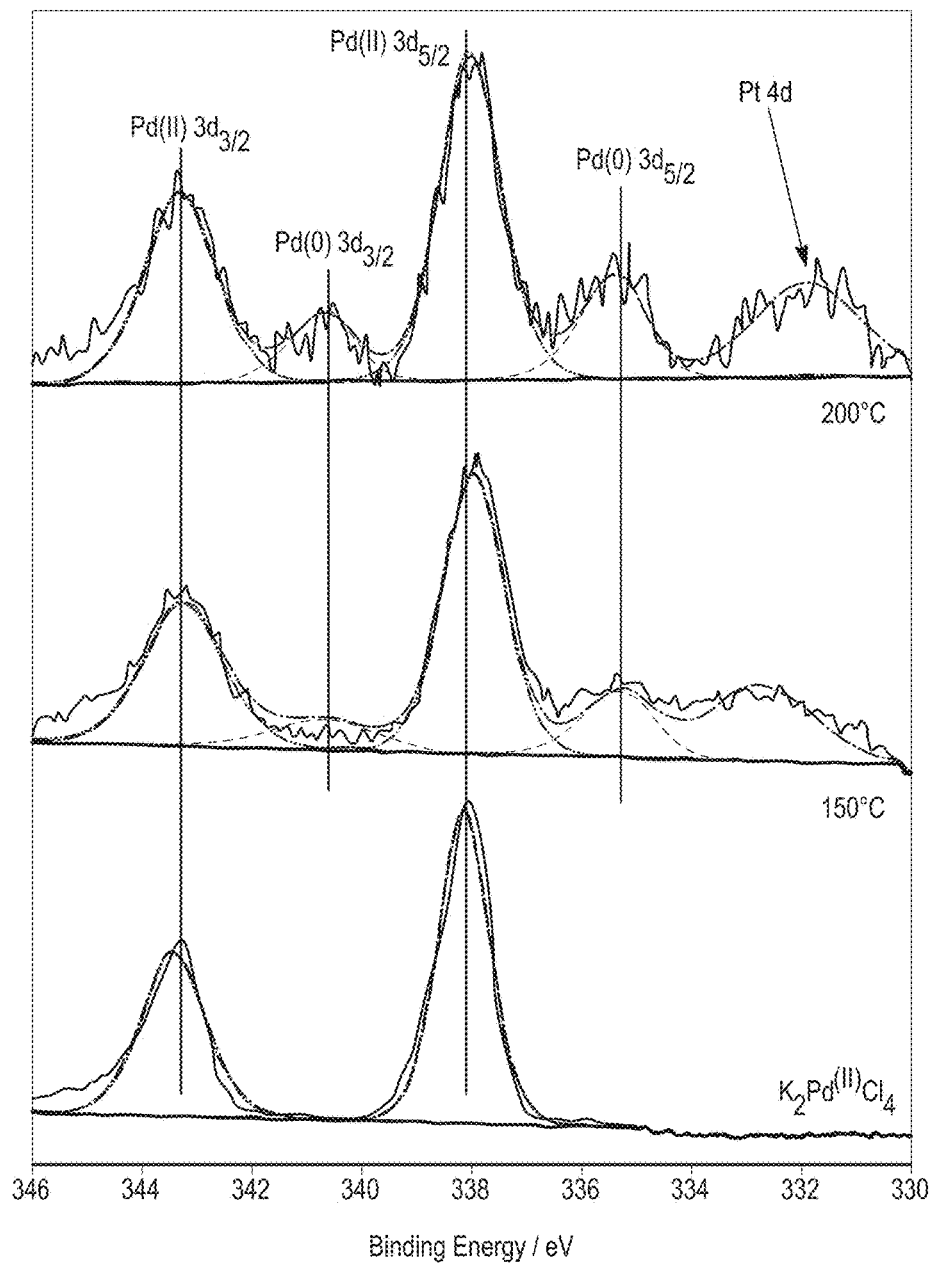
Figure 45A:
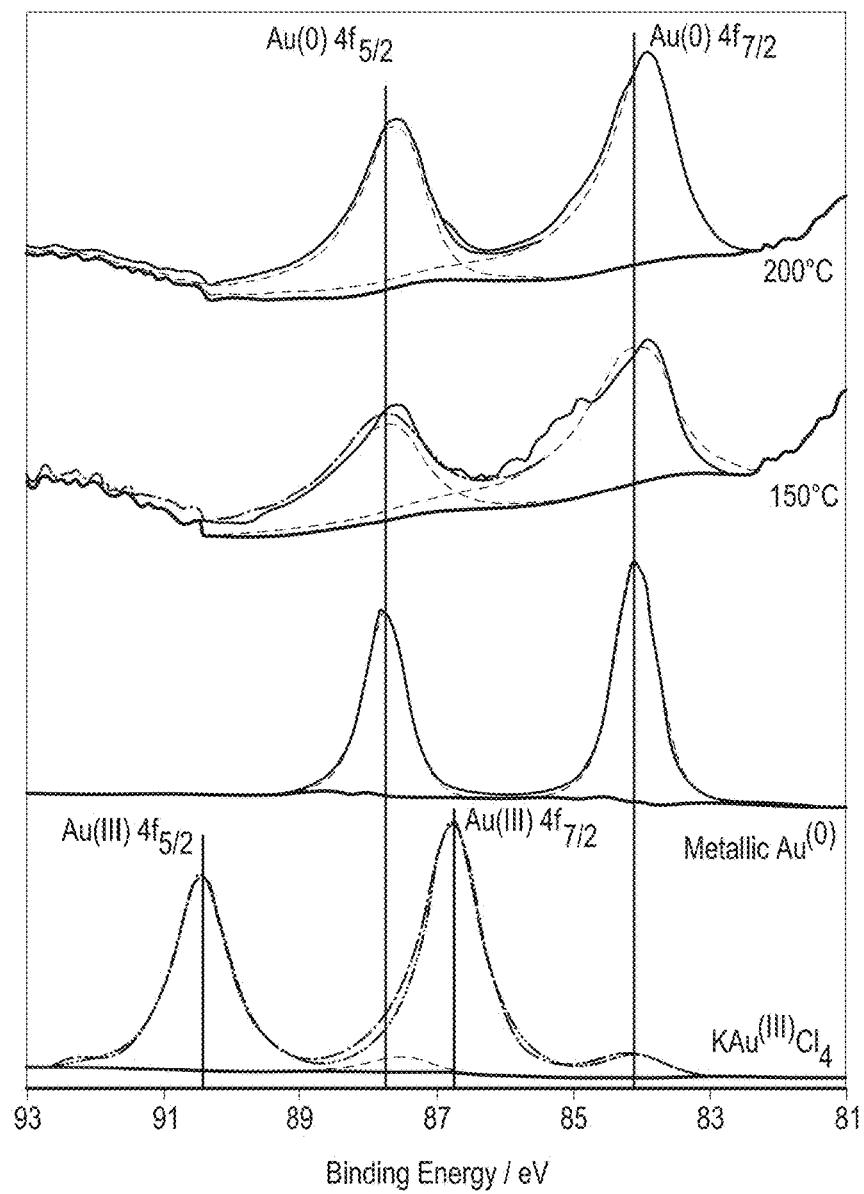
FIGS. 45A and 45B are related to Example 4 and illustrate stacked XPS spectra, with data fits and appropriate reference samples, of exemplary AuPd/CuClP catalyst materials activated at different temperatures.
Figure 45B:
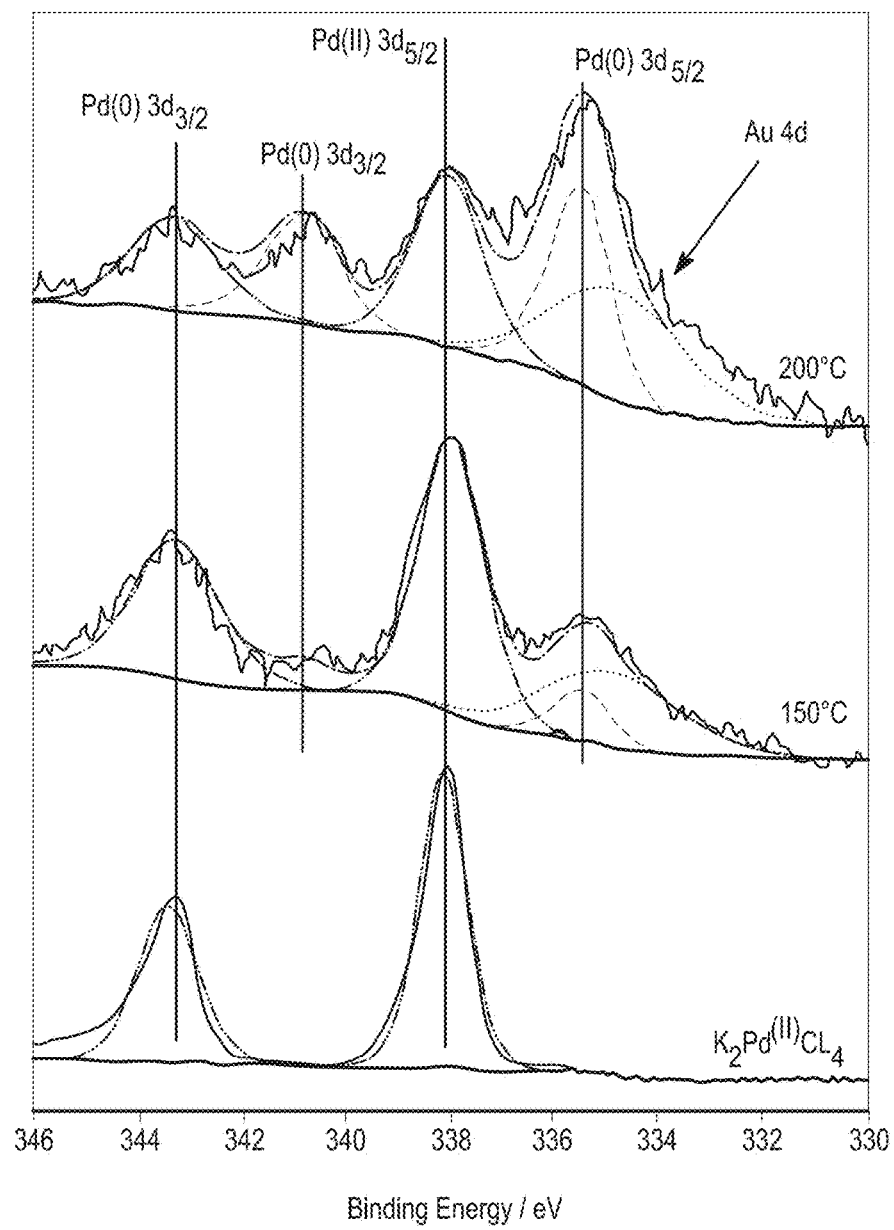
Figure 50A:
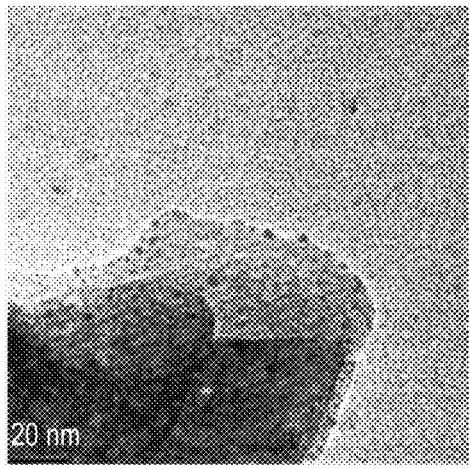
FIGS. 50A and 50B are related to Example 4 and illustrate TEM images of the AuPt/CuClP material activated at 250° C.
Figure 50B:
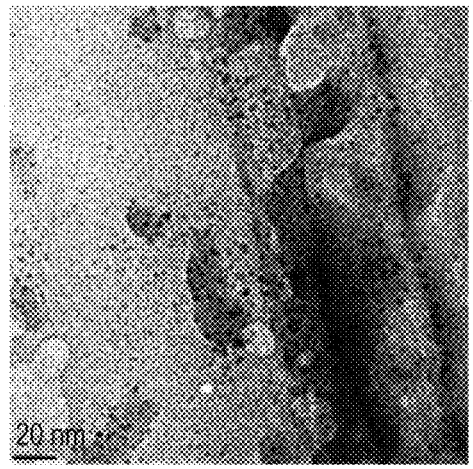
Figure 51A:
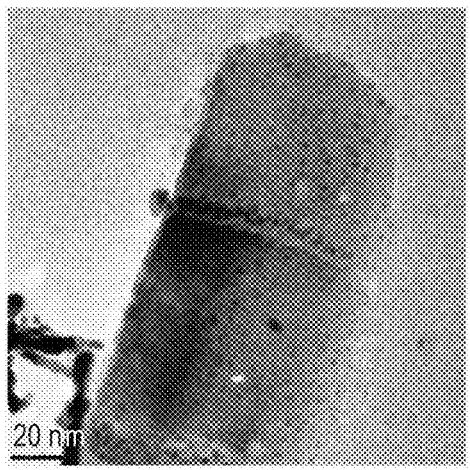
FIGS. 51A and 51B are related to Example 4 and illustrate TEM images of the AuPt/CuClP material activated at 300° C.
Figure 51B:
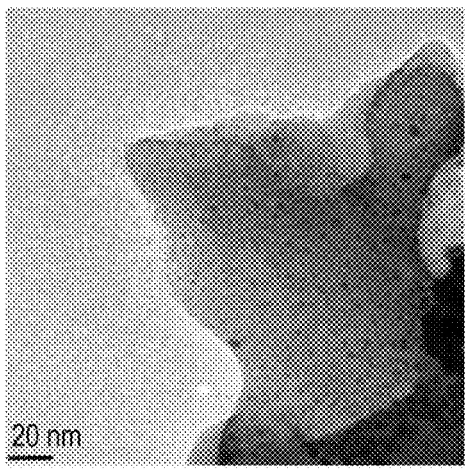

42C illustrates an EDXS sum-spectrum, obtained by summing all spectra from the spectrum image. FIG. 42D illustrates elemental maps obtained from the spectrum image by peak integration. FIG. 42D indicates significant Cu nanoparticle formation and agglomeration. Without wishing to be held to any particular theory, the slightly mottled appearance of the Au map suggests formation of Au nanoparticles may have occurred across the framework, although the relatively uniform distribution of Au also suggests that a significant fraction of Au may also still reside within the original framework material.

Example 3: Catalytic Testing

Comparative Examples

Chemicals for catalytic tests were purchased from Sigma Aldrich or Fisher Scientific and used without further purification. Catalytic reactions were carried out in a fixed-bed flow reactor using pelletized catalyst (approx. 0.1-1 g). The reactor assembly was set up and purged under the flow of air at 200° C. for one hour before the substrate feed was allowed to saturate the system. The substrate and air flow rates were adjusted to their experimental level and left to equilibrate for one hour. All reactions were carried out using an air flow of 25 mLmin$^{-1}$, a cyclohexanol flow of 7.5 μLmin$^{-1}$ or a KA-oil flow of 15 μLmin$^{-1}$ and at 200° C. unless stated otherwise. KA-oil solutions were made up of 50:50% wt. ratio of cyclohexanol and cyclohexanone.

An external standard solution of triethyleneglycol dimethyl ether (2 M) in acetone was fed into the off-stream of the reactor at the same rate as the substrate. The solution obtained was diluted at a ratio of 1:10 with acetone before being subject to GC analysis.

Samples were analyzed by GC (PerkinElmer, Clarus 480) using an Elite-5 column equipped with a flame ionization detector (FID). Products were identified against authenticated standards and quantified by calibration to obtain response factors against the known external standard.

Results for the un-doped framework in the absence of catalyst are provided in Table 4, showing minimal levels of conversion for both the un-doped framework and the reactions in the absence of catalyst.

TABLE 4

Catalytic data from the aerobic oxidation of cyclohexanol and KA-oil in Comparative Examples

| Catalyst | Substrate | Temp/ ° C. | Cyclohexanol Conversion/ mol. % | Cyclohexanone Selectivity/ mol. % | Mass Balance/ % |
|---|---|---|---|---|---|
| CuClP | Cyclohexanol | 200 | 1 | >99 | 95 |
| CuClP | Cyclohexanol | 300 | 2 | >99 | 94 |
| None | Cyclohexanol | 200 | 1 | >99 | 97 |
| None | Cyclohexanol | 300 | 2 | >99 | 92 |
| None | KA-oil | 200 | 3 | >99 | 94 |
| None | KA-oil | 300 | 3 | >99 | 93 |

Catalytic Conversion of Cyclohexanol to Cyclohexanone

The copper chloropyrophosphate framework doped with gold, platinum or palladium tetrachloride precursors were hydrothermally synthesized at 175° C. for 48 hr. Materials were post-synthetically activated under reduction for 2 hr. at specified temperatures (150° C.-250° C.) under a 150 mLmin$^{-1}$ flow of 5% hydrogen in nitrogen. The aerobic oxidation of KA-oil was studied under continuous-flow conditions under atmospheric pressure employing a custom-made fixed-bed reactor (Cambridge Reactor Design, UK).

Figure 20B:
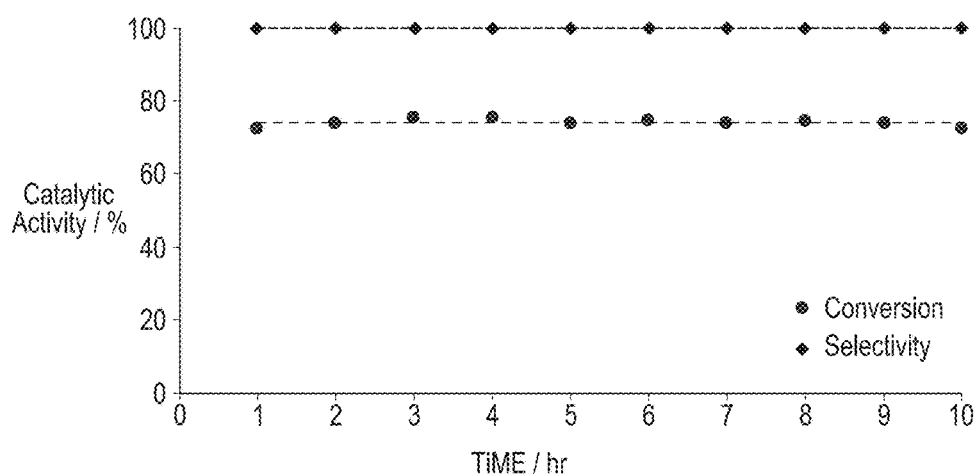
FIG. 20B is related to Example 3 and illustrates the catalytic lifetime of the Pt/CuClP catalyst.

FIG. 20A contrasts the aerobic production of cyclohexanone with supported nanoparticle/CuClP catalysts. Showing the superior activity of Pt/CuClP for this process and the ability to optimize this reaction with adroit catalyst design. FIG. 20B highlights the exceptional catalytic lifetime of the Pt/CuClP catalyst. Displaying consistent cyclohexanol conversion and cyclohexanone selectivity profiles over a 10 hr. period. Reaction temperature: 200° C., air flow: 25 mLmin$^{-1}$, substrate flow: 15 μLmin$^{-1}$, WHSV: 1.8 hr$^{-1}$. Full tabulated data is presented in Tables 5 and 6. Table 5 presents catalytic results summarizing the activities and selectivities of Au, Pt & Pd catalysts activated under specific conditions in the aerobic oxidation of KA-oil. Table 6 presents the influence of time-on-stream on activity and selectivity in KA-oil oxidation using Pt/CuClP (activated at 200° C.) catalyst.

TABLE 5

Catalytic results summarizing the activities and selectivities of activated Au, Pt & Pd catalysts in the aerobic oxidation of KA-oil.

| Catalyst | Activation Temperature/ ° C. | WHSV/ hr$^{-1}$ | Cyclohexanol Conversion/ mol. % | Cyclohexanone Selectivity/ mol. % | Mass Balance/ % |
|---|---|---|---|---|---|
| Au/CuClP | 150 | 1.84 | 4 | >99 | 95 |
| Au/CuClP | 175 | 1.65 | 4 | >99 | 91 |
| Au/CuClP | 200 | 1.76 | 3 | >99 | 98 |
| Au/CuClP | 250 | 1.71 | 1 | >99 | 94 |
| Pt/CuClP | 150 | 1.81 | 7 | >99 | 90 |
| Pt/CuClP | 175 | 1.74 | 16 | >99 | 92 |
| Pt/CuClP | 200 | 1.76 | 74 | >99 | 97 |
| Pd/CuClP | 150 | 1.84 | 1 | >99 | 99 |
| Pd/CuClP | 175 | 1.82 | 1 | >99 | 97 |
| Pd/CuClP | 200 | 1.77 | 5 | >99 | 93 |

TABLE 6

Influence of time-on-stream on activity and selectivity in KA-oil oxidation using activated Pt/CuClP catalyst.

| Time/ | Cyclohexanol Conversion/ mol. % | Cyclohexanone Selectivity/ % | Mass Balance/ % |
|---|---|---|---|
| 1 | 72 | >99 | 99 |
| 2 | 74 | >99 | 97 |
| 3 | 76 | >99 | 87 |
| 4 | 76 | >99 | 84 |
| 5 | 74 | >99 | 87 |
| 6 | 75 | >99 | 85 |
| 7 | 74 | >99 | 86 |
| 8 | 75 | >99 | 84 |
| 9 | 74 | >99 | 86 |
| 10 | 73 | >99 | 88 |

FIG. 20A highlights the superior performance of the Pt catalyst over that of its corresponding Pd and Au analogues, and it is remarkably noteworthy that the selectivity for the desired cyclohexanone was in excess of 99+% for the Pt catalyst (HPLC and GC-MS investigations did not reveal the presence of dibasic acids and esters). Not only is the Pt/CuClP a highly effective and selective aerobic oxidation catalyst (the undoped framework is inert), but the robust nature of this material is evidenced by its ability to maintain both high levels of activity and selectivity over extended periods on stream (as displayed in FIG. 20B). More importantly, the material retains its structural integrity post-catalysis (FIG. 10), and negligible metal leaching (as measured by inductively coupled plasma optical emission spectroscopy (ICP-OES)) was observed. These findings support the hypothesis that the catalytic activity of these materials can be intrinsically linked to the degree of nanoparticle formation: the $[PtCl_4]^{2-}$ precursor has a greater propensity for nanoparticle formation over a range of activation temperatures and this, in concert with the surrounding microporous architecture, bestows superior catalytic performance for the aerobic oxidation of KA-oil.

Catalytic Conversion of Cyclohexanol to Cyclohexanone—Closed Loop System

The parameters described above with respect to the KA-oil oxidation examples were used. However, in order to mimic a closed loop system new substrate feed solutions were prepared to the measured molar ratio of the appropriate out-stream. After the initial purge the substrate (15 μLmin$^{-1}$) and air (25 mLmin$^{-1}$) flow rates were set up and the system left to equilibrate for one hour. After which a sample was analyzed by GC (as above) and the cyclohexanol to cyclohexanone molar ratio determined. At which point a new substrate feed solution was made to the predetermined molar ratio of the previous sample. This process was repeated for the number of cycles shown in Table 7.

TABLE 7

Catalytic data from closed-loop experiments involving the Pt/CuClP catalyst (activated at 200° C.).

| Cycle | Substrate Feed Molar Ratio (Cyol:Cyone) | Cyclohexanol Conversion/ mol. % | Cyclohexanone Selectivity/ mol. % | Mass Balance/ % |
|---|---|---|---|---|
| 1 | 1:1 | 67 | >99 | 88 |
| 2 | 0.5:1 | 81 | >99 | 85 |
| 3 | 0.1:1 | 93 | >99 | 84 |
| 4 | 0.04:1 | 95 | >99 | 90 |

Catalytic Conversion of Cyclohexanol to Cyclohexanone—Varying Temperature and Flow Rates A 7 wt. % Pt/CuClP catalyst was prepared similar to described above and reduced at 200° C. for 2 hours under 5% hydrogen in nitrogen. A 1:1 mass ratio of cyclohexanol to cyclohexanone was provided as the feed stream. The percentage cyclohexanol, cyclohexanone and the mass balance for each sample during the reaction was plotted, and for clarity, the percentage conversion, selectivity for cyclohexanone and the normalized selectivity were also plotted. The selectivity was reported as >99% as only one product, cyclohexanone, was detected by GC. From this, the normalized selectivity was determined by taking into account the mass balance for the reaction using the equation below:

Normalised selectivity (mol %)=selectivity (mol %)×mass balance (%)/100%

Figure 21:
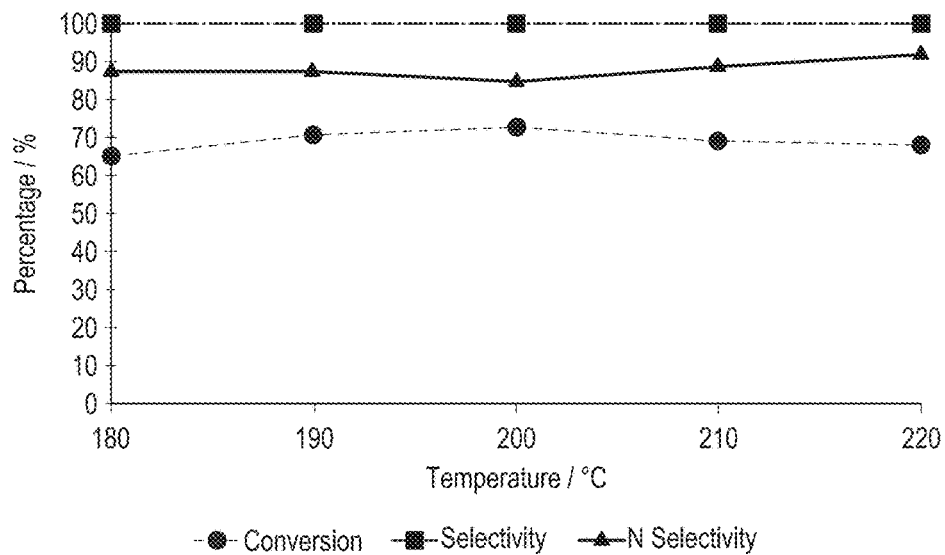
FIG. 21 is related to Example 3 and illustrates the effect of temperature on the conversion of cyclohexanol to cyclohexanone.

The effect of temperature was first investigated, as shown in FIG. 21. A 0.24 g sample of catalyst was exposed to a 15 μLmin$^{-1}$ flow of the 1:1 mixture of cyclohexanol and cyclohexanone and 25 mLmin$^{-1}$ flow of air. The reaction temperature was varied from 180° C. to 220° C. Over the temperature range investigated it can be seen that the conversion, selectivity and normalized selectivity remains fairly constant, with the highest conversion being achieved at 200° C.

Figure 22:
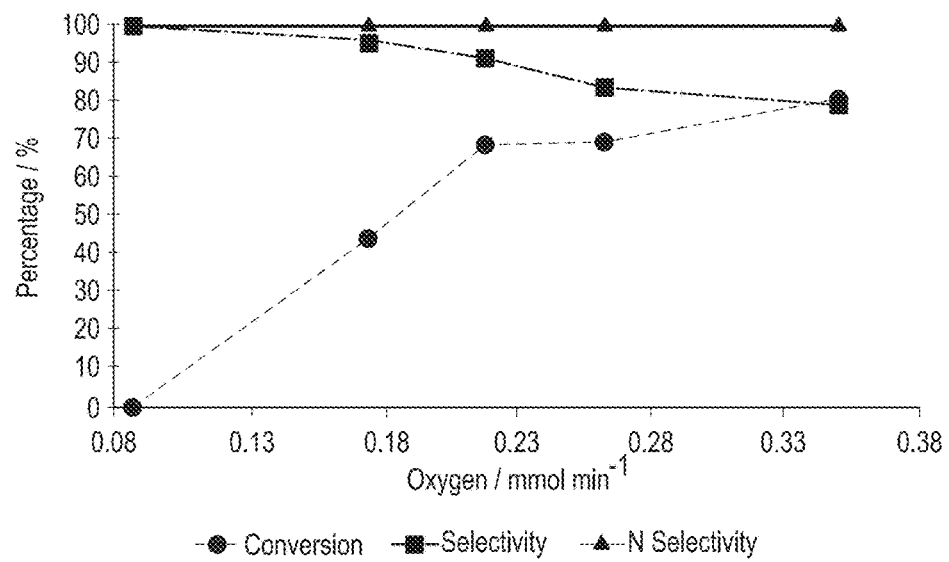
FIG. 22 is related to Example 3 and illustrates the effect of oxygen flow rate on the conversion of cyclohexanol to cyclohexanone.

Next, the effect of air flow rate was investigated. The reaction conditions were the same as for the temperature investigation, except that a reaction temperature of 200° C. was utilized, and the air flow rate was varied between 10 mLmin$^{-1}$ and 40 mLmin$^{-1}$. FIG. 22 provides the results as a function of the oxygen flow in mmolmin$^{-1}$, which increases with an increase in air flow rate. As shown in FIG. 22, the conversion starts to level off at an oxygen concentration of approximately 0.22 mmolmin$^{-1}$, and the mass balance (as reflected by the normalized selectivity) also starts to decrease around this point. Without wishing to be held to any particular theory, it is believed that the cyclohexanol is being oxidized to products that cannot be detected by GC, or is being lost in potential vapor loss during sampling and sample handling. Overall, FIG. 22 shows the trend of increased conversion with increased oxygen concentration.

Figure 23:
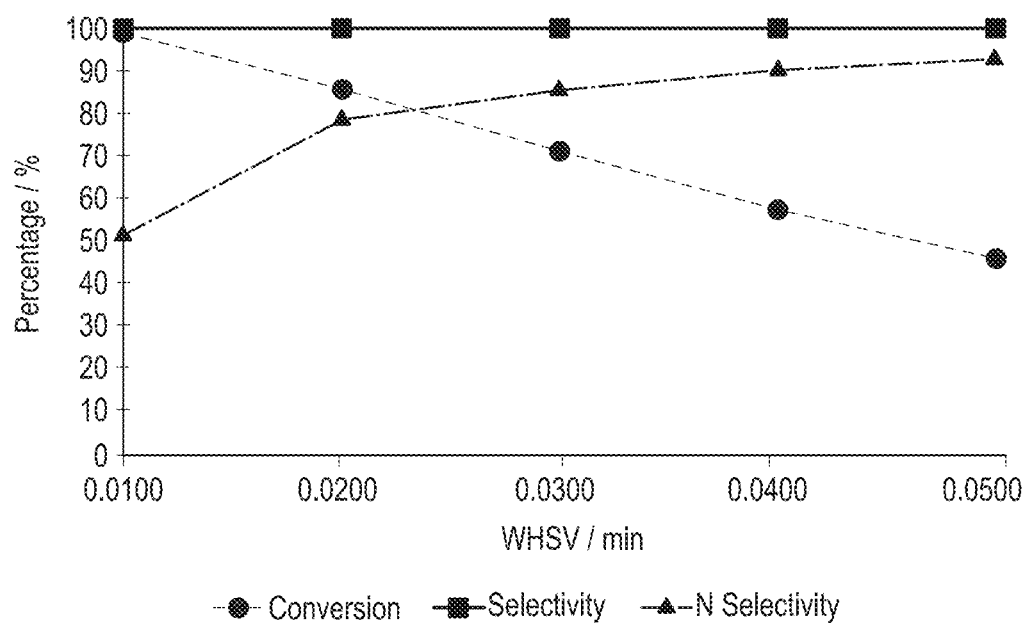
FIG. 23 is related to Example 3 and illustrates the effect of cyclohexanol flow rate on the conversion of cyclohexanol to cyclohexanone.

Next, the effect of the incoming cyclohexanol/cyclohexanone mixture flow rate was investigated. The reaction conditions were the same as for the temperature investigation, except that a reaction temperature of 200° C. was utilized, and the flow rate of the cyclohexanol/cyclohexanone mixture was varied between 5-25 μLmin$^{-1}$. FIG. 23 provides the results as a function of the weighted hourly space velocity (WHSV), which increases with the flow rate of the cyclohexanol/cyclohexanone mixture. WHSV was calculated according to the formula:

$$WHSV(hr.^{-1}) = \frac{\text{Cyclohexanol flow (g hr.}^{-1})}{\text{Mass catalyst (g)}}$$

As shown in FIG. 23, the conversion decreases with increasing WHSV. Without wishing to be held to any particular theory, it is believed that the decrease is due to lower contact times of the substrate with the catalyst.

Example 4—Bi-Metallic Examples

Synthesis, Activation, and Characterization

All chemicals were purchased from Sigma Aldrich or Fisher Scientific and used without further purification. Gases were sourced from BOC Industrial Gases and used as supplied.

Copper(II) fluoride (0.1168 g, 1.15 mmol), rubidium chloride (0.2800 g, 2.32 mmol) and two sources of metal chloride salt selected from 0.0245 g (0.072 mmol) gold(III) chloride hydrate, 0.0299 g (0.072 mmol) potassium tetrachloroplatinate, or 0.0250 g (0.077 mmol) potassium tetrachloropalladate were accurately weighed out to 4 decimal places and ground in an agate pestle and mortar for 2 minutes to homogenize.

The mixture was added to the Teflon® liner of a 23 mL hydrothermal vessel, and 85% orthophosphoric acid in water (0.20 mL, 2.92 mmol) was added dropwise wetting the entire contents. The mixture was sonicated for 5 minutes to encourage mixing. 0.24 mL (2.38 mmol) of 50 wt. % rubidium hydroxide in water was added dropwise, wetting the entire contents, and the mixture was sonicated for 10-15 minutes until the mixture was homogenous. Caution was taken due to production of hydrogen fluoride gas.

The hydrothermal vessel was sealed and heated to 175° C. for 48 hours in a convection oven. The vessels were allowed to cool naturally before collecting the product by filtration, washing with deionized water (100 mL) and drying overnight at 80° C.

Figure 24:
FIG. 24 is related to Example 4 and is a photograph of the as-synthesized bimetallic CuClP materials.

A photograph of the as-synthesized bimetallic CuClP materials is provided in FIG. 24, showing, from left to right, AuPt/CuClP, AuPd/CuClP and PtPd/CuClP. Products formed as brilliant green cuboid crystals for AuPt material, and as light brown/green crystals for the AuPd and PtPd materials.

Figure 25:
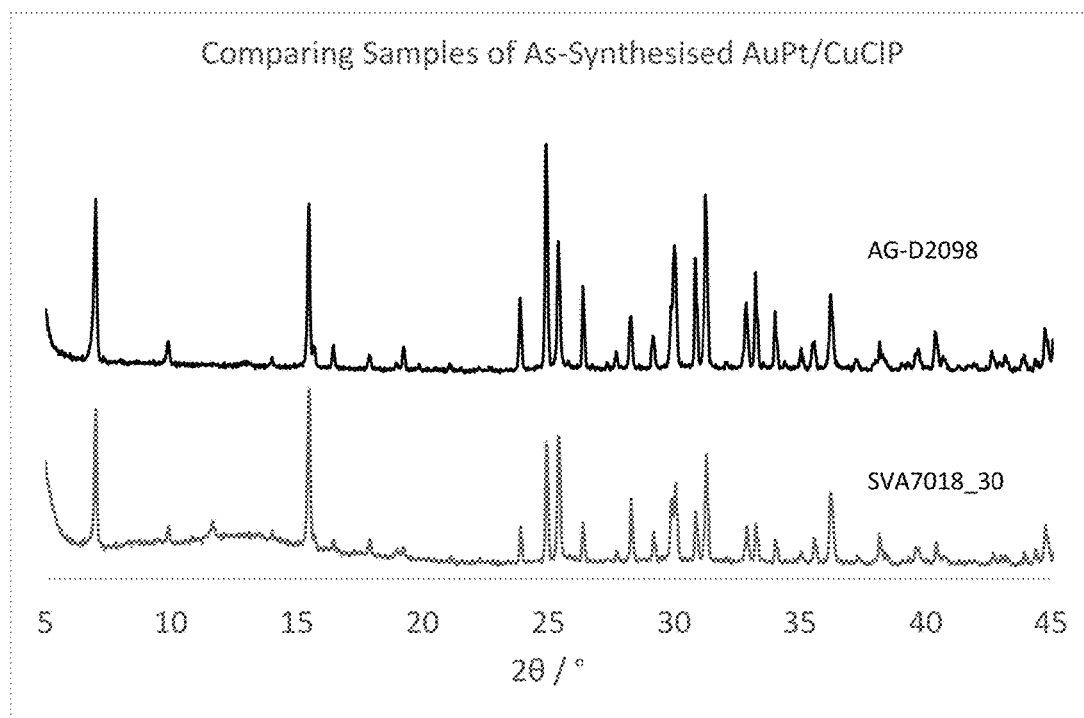
FIG. 25 is related to Example 4 and illustrates the PXRD spectra of two different as-synthesized AuPt/CuClP samples.
Figure 26:
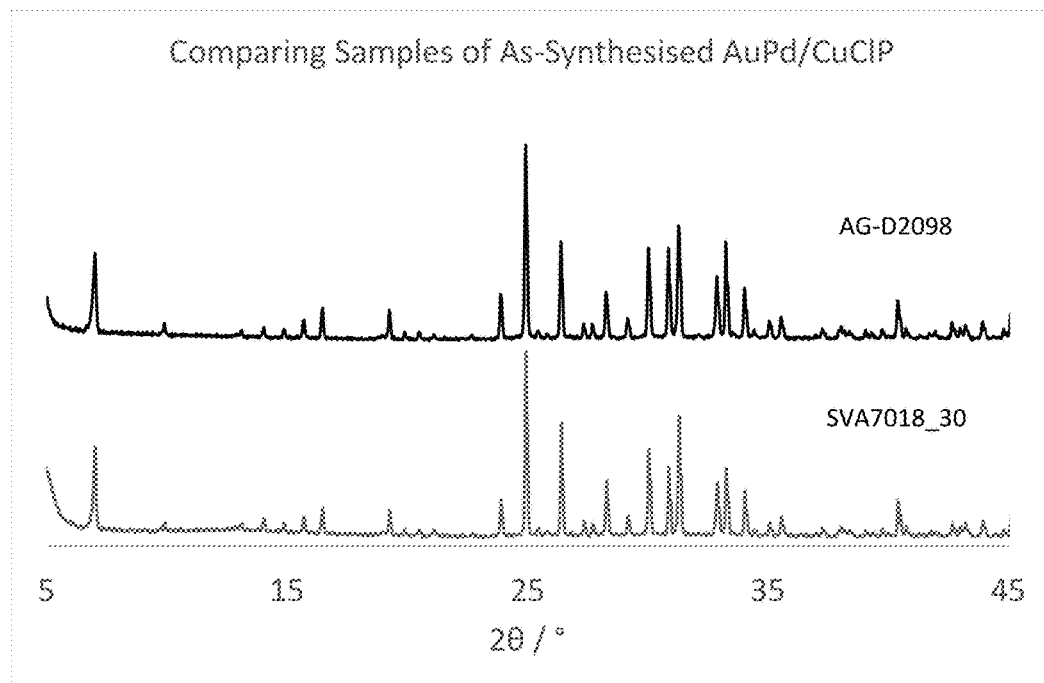
FIG. 26 is related to Example 4 and illustrates the PXRD spectra of two different as-synthesized AuPd/CuClP samples.
Figure 27:
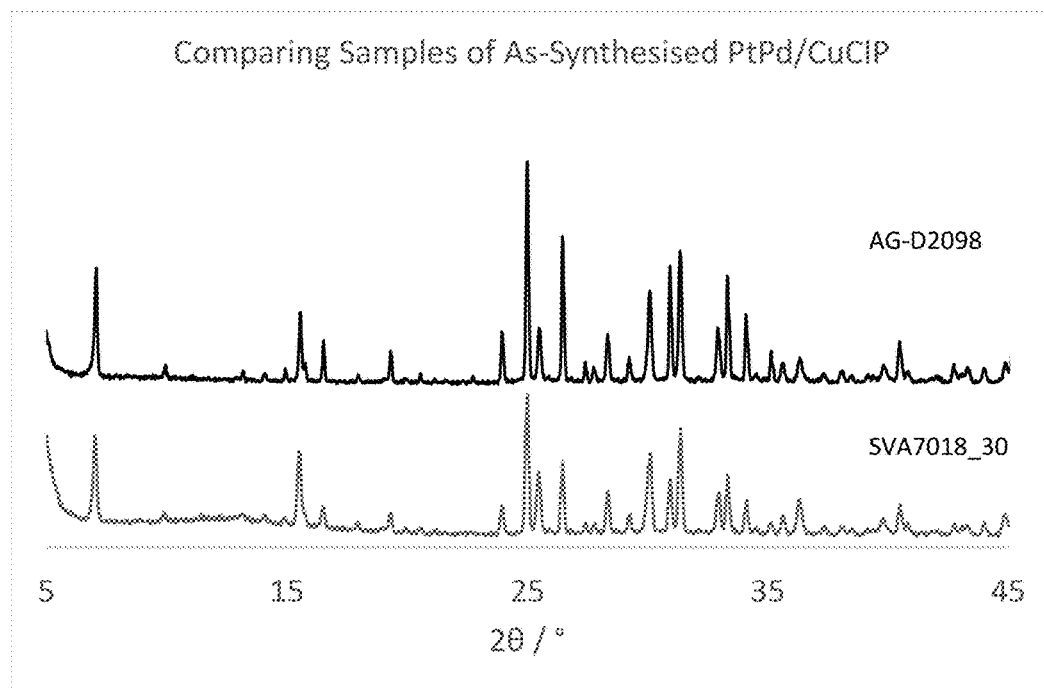
FIG. 27 is related to Example 4 and illustrates the PXRD spectra of two different as-synthesized PtPd/CuClP samples.

The PXRD spectra of the as-synthesized bi-metallic materials were obtained as discussed above with respect to the mono-metallic materials. FIG. 25 shows the PXRD spectra of two different as-synthesized AuPt/CuClP samples. FIG. 26 shows the PXRD spectra of two different as-synthesized AuPd/CuClP samples. FIG. 27 shows the PXRD spectra of two different as-synthesized PtPd/CuClP samples.

Materials were activated under reducing conditions under a flow of 5% $H_2/N_2$ at approximately 150 $mLmin^{-1}$ for 2 hours at the specified temperature.

Figure 28:
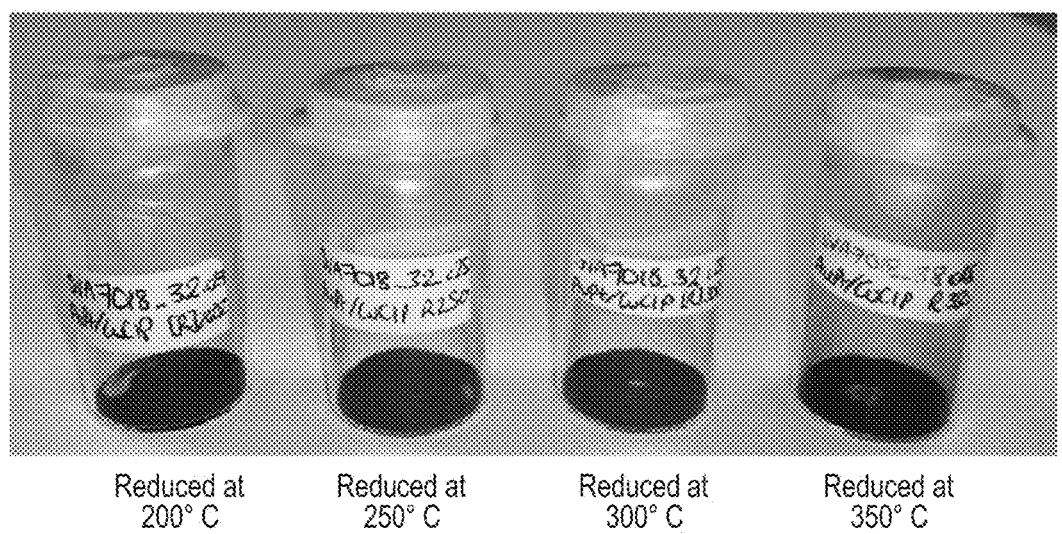
FIG. 28 is related to Example 4 and is a photograph of the bimetallic AuPt/CuClP material reduced at different temperatures.

The AuPt/CuClP bi-metallic material was reduced at temperatures of 200° C., 250° C., 300° C., and 350° C. for 2 hours under hydrogen. As shown in FIG. 28, after reduction, the AuPt material appeared progressively darker with temperature. The color of the sample reduced at 350° C. is actually a black-green color with a hint of red suggesting that gold nanoparticles have formed. Without wishing to be held to any particular theory, it is believed that that gold nanoparticles are only formed in significant amounts at temperatures of 350° C. and above.

Figure 29:
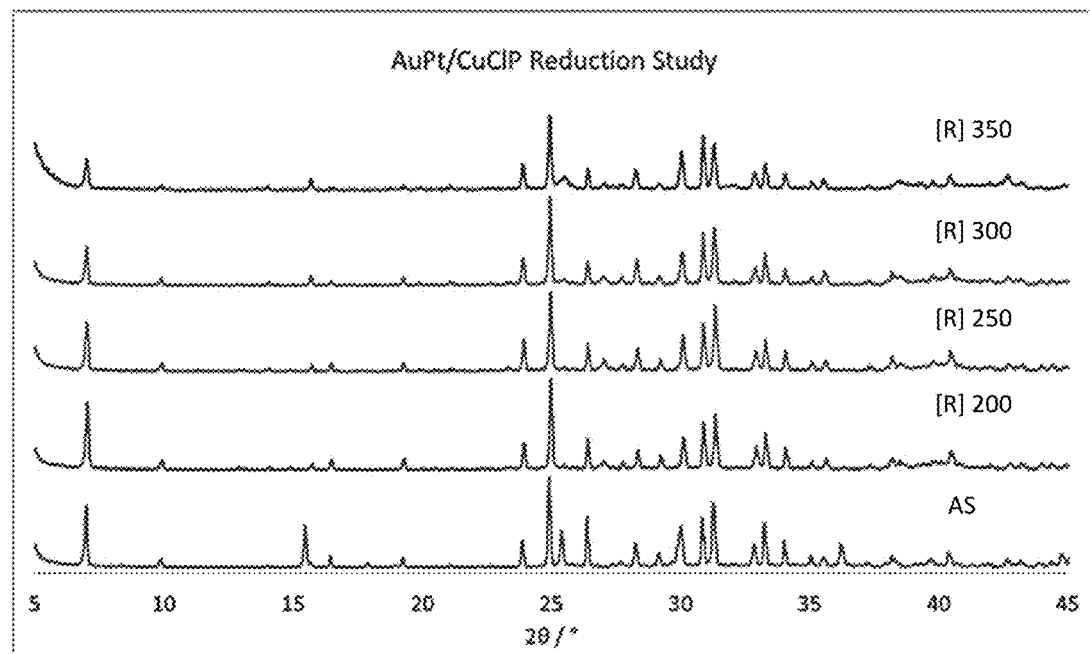
FIG. 29 is related to Example 4 and illustrates the PXRD spectra of the as-synthesized AuPt/CuClP material and samples reduced at different temperatures.
Figure 30:
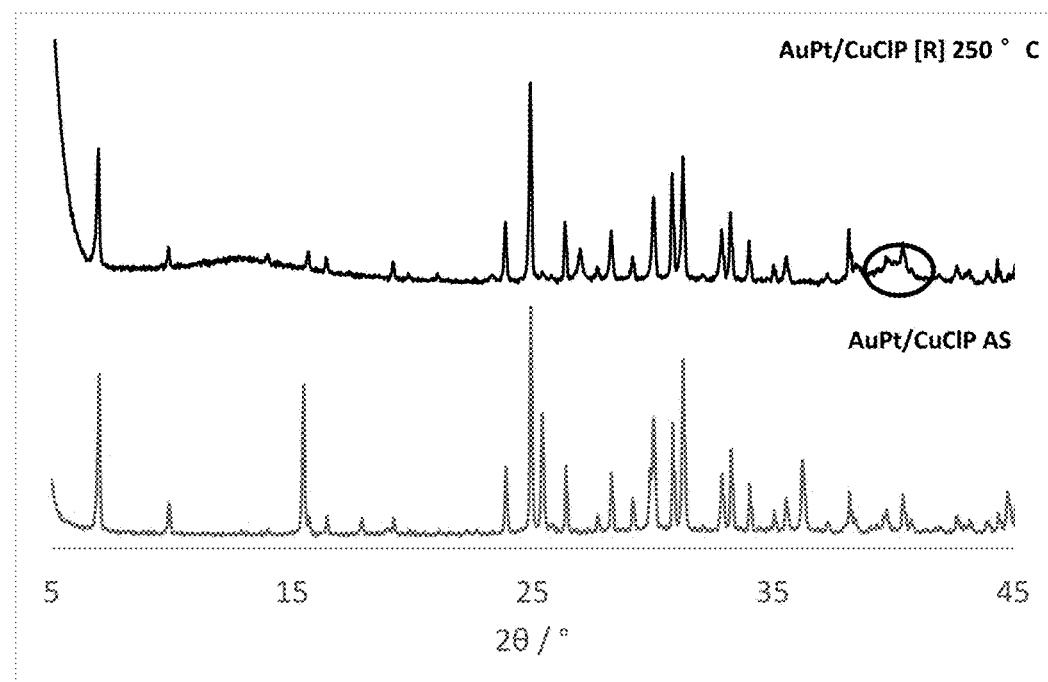
FIG. 30 is related to Example 4 and illustrates the PXRD spectra of the as-synthesized AuPt/CuClP material and samples reduced at 250° C.

FIG. 29 shows the PXRD spectra of the AuPt/CuClP samples as-synthesized and as reduced at 200° C., 250° C., 300° C., and 350° C. As indicated in FIG. 29, the PXRD patterns suggest that the framework is still intact after reduction at different activation temperatures. Broad peaks signifying the presence of nanoparticulate platinum usually appear ~40°. This can also be seen in FIG. 30, which compares the PXRD pattern of the as-synthesized AuPt/CuClP material with a sample reduced at 250° C. The nanoparticle platinum peaks are highlighted in the circled portion of the reduced spectrum.

Figure 31:
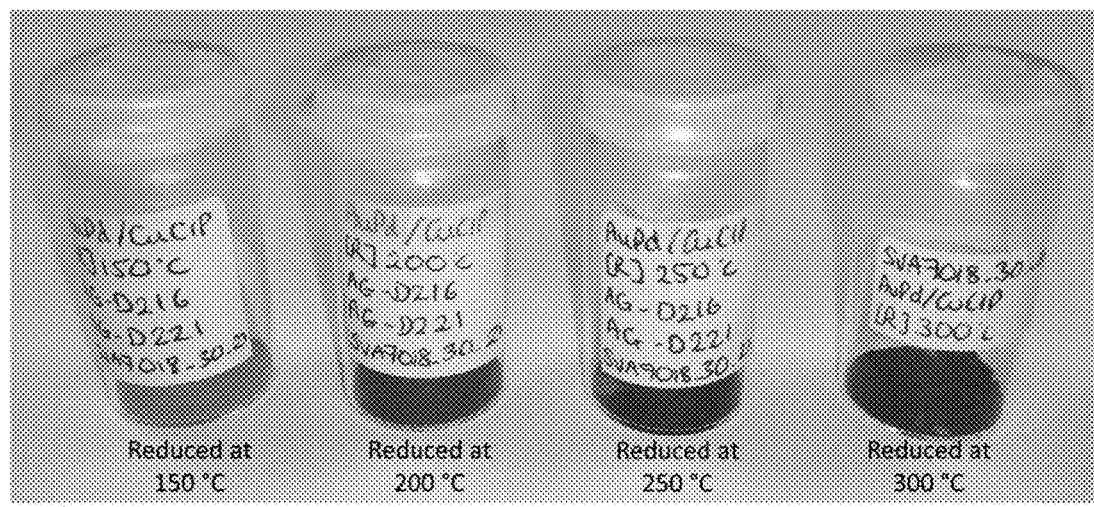
FIG. 31 is related to Example 4 and is a photograph of the bimetallic AuPd/CuClP material reduced at different temperatures.

The AuPd/CuClP bi-metallic material was reduced at temperatures of 150° C., 200° C., 250° C., and 300° C. for 2 hours under hydrogen. As shown in FIG. 31, the material changed from light brown/green to dark green from 150° C. to 200° C., and then black at temperatures higher than 250° C. where the framework degrades, as confirmed by PXRD analysis. Similarly to the AuPt/CuClP sample, the AuPd/CuClP materials also get darker at higher activation temperatures.

Figure 32:
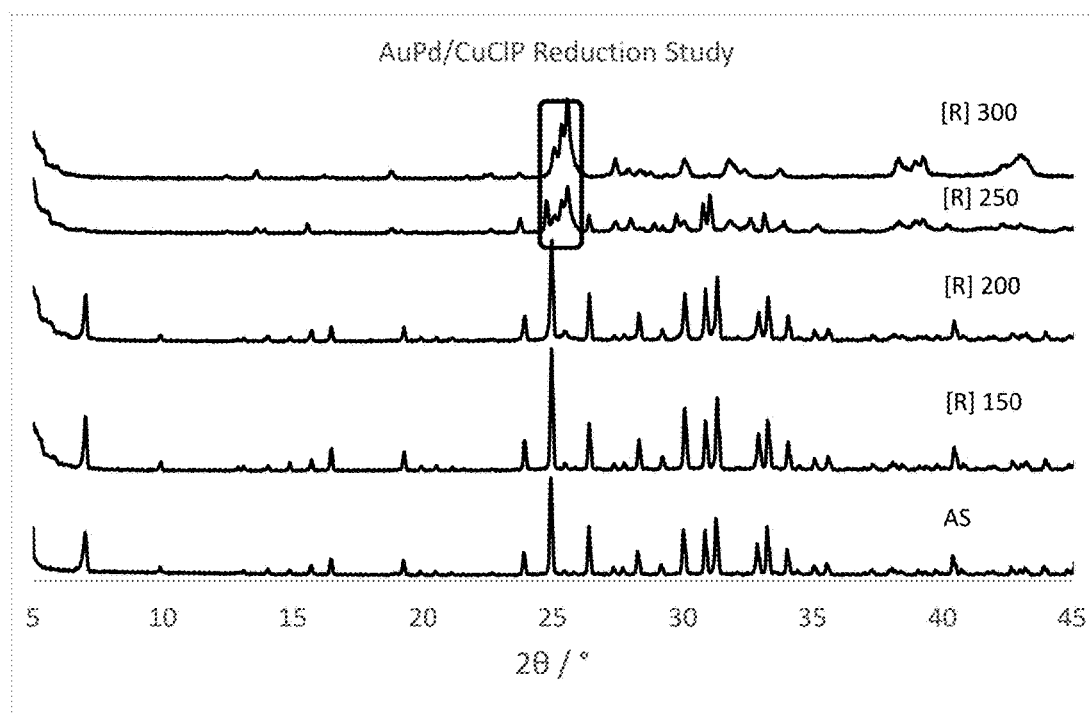
FIG. 32 is related to Example 4 and illustrates the PXRD spectra of the as-synthesized AuPd/CuClP material and samples reduced at different temperatures.

The PXRD patterns for the reduced AuPd/CuClP bi-metallic material are shown in FIG. 32 below alongside the as-synthesized material. As shown in FIG. 32, the AuPd/CuClP framework begins to degrade when reduced above 250° C., as illustrated by the decrease in signal intensity and by the disappearance of key peaks around 7 and 25°. An additional rubidium phosphate phase is also present around 25°, as highlighted by the box in FIG. 32, further suggesting the breakdown of the framework.

Figure 33:
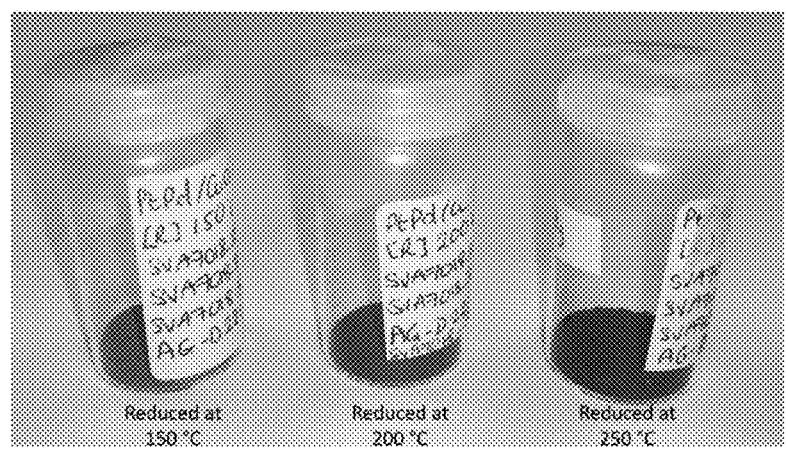
FIG. 33 is related to Example 4 and is a photograph of the bimetallic PtPd/CuClP material reduced at different temperatures.

The PtPd/CuClP bi-metallic material was reduced at temperatures of 150° C., 200° C., and 250° C. under hydrogen. As shown in FIG. 33, the material changed from light brown/green to dark green from 150° C. to 200° C., and then black at temperatures higher than 250° C. where the framework degrades, as confirmed by PXRD analysis.

Figure 34:
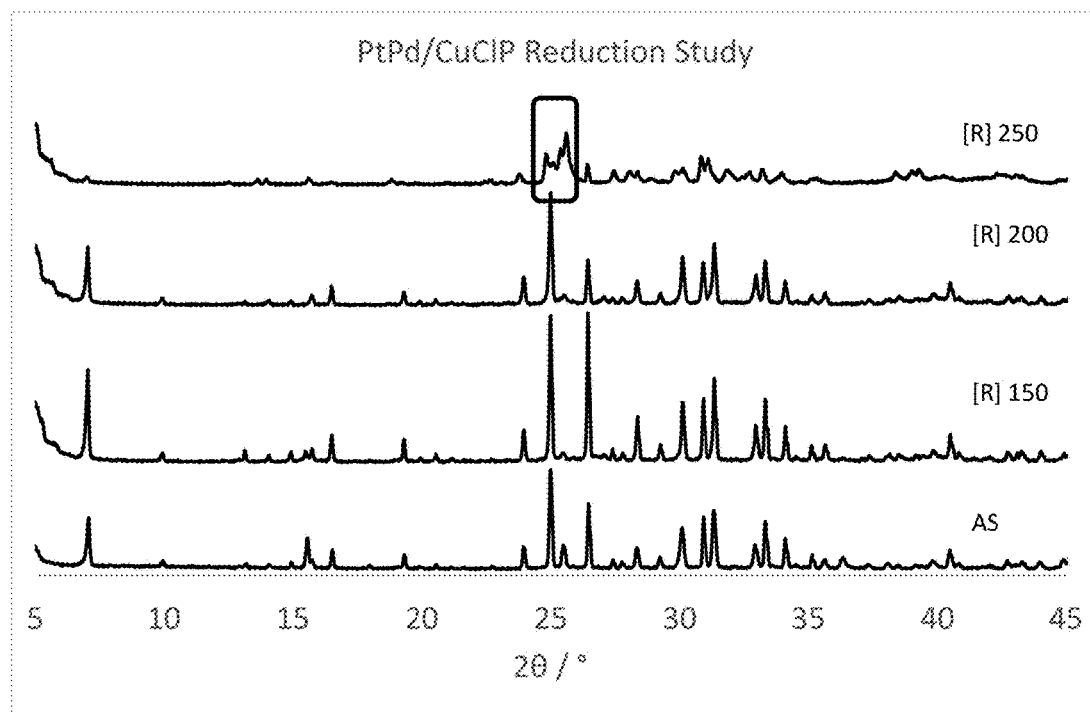
FIG. 34 is related to Example 4 and illustrates the PXRD spectra of the as-synthesized PtPd/CuClP material and samples reduced at different temperatures.

The PXRD patterns for the reduced PtPd/CuClP bi-metallic materials are shown in FIG. 34 alongside the as-synthesised material. Similarly to the AuPd/CuClP material, the sample reduced at 250° C. has started to degrade. The rubidium phosphate phase is also present in this sample, as highlighted by the box in FIG. 34, confirming the change in the sample due to degradation.

FIGS. 43-47 illustrate stacked XPS spectra, with data fits and appropriate reference samples, of various bimetallic materials activated at different temperatures. The XPS spectra for exemplary AuPt/CuClP catalyst materials activated at different temperatures is provided in FIG. 43. The XPS spectra for exemplary PtPd/CuClP catalyst materials activated at different temperatures are provided in FIGS. 44A and 44B. The XPS spectra for exemplary AuPd/CuClP catalyst materials activated at different temperatures are provided in FIGS. 45A and 45B.

FIGS. 46-51 illustrate TEM images of various bimetallic materials activated at different temperatures. FIGS. 46A and 46B illustrate TEM images of the AuPd/CuClP material activated at 200° C. FIG. 47 illustrates a TEM image of the PtPd/CuClP material activated at 150° C. FIGS. 48A-48C illustrate TEM images of the PtPd/CuClP material activated at 200° C. FIGS. 49A and 49B illustrate TEM images of the AuPt/CuClP material activated at 200° C. FIGS. 50A and 50B illustrate TEM images of the AuPt/CuClP material activated at 250° C. FIGS. 51A and 51B illustrate TEM images of the AuPt/CuClP material activated at 300° C.

Catalytic Conversion of Cyclohexanol to Cyclohexanone

Catalytic reactions were performed in a fixed-bed flow reactor (4 mm in diameter) with a glass frit, in which a layer of pelletized catalyst approximately 0.24 g) was packed between two layers of glass beads. The system was preheated to 200° C. under a 25 $mLmin^{-1}$ flow of air for 1 hour. The substrate flow rate was set to 15 $\mu Lmin^{-1}$, in order to achieve a WHSV of 1.8 $hr^{-1}$, and the system was allowed to equilibrate for 1 hour.

The KA-oil substrate feedstock solutions were made up as a 1:1 weight ratio of cyclohexanol and cyclohexanone, and an external standard solution of triethylene glycol dimethyl ether (2 M) in acetone was fed into the off-stream of the reactor at the same flow rate as the substrate. The solution obtained from the off-stream was diluted in a ratio of 1:10 with acetone before being subject to GC analysis. Samples were analyzed on an hourly basis using a Clarus 400 gas chromatogram with FID using an Elite 5 column, and the peak areas were calibrated using known response factors.

The bi-metallic CuClP materials were tested for the conversion of cyclohexanol to cyclohexanone, and a summary of the results for all three systems is tabulated below in Tables 8 and 9.

TABLE 8

Percentage conversions in the oxidation of KA-oil for the bimetallic CuClP catalysts reduced at 200° C.

| Catalyst | Percentage Conversion/mol. % |
|---|---|
| AuPt/CuClP | 36 |
| AuPd/CuClP | 0 |
| PtPd/CuClP | 69 |

TABLE 9

Percentage conversions in the oxidation of KA-oil for the AuPt/CuClP bimetallic catalyst reduced at different temperatures

| Activation Temperature/° C. | Cyclohexanol Conversion/mol. % |
|---|---|
| 200 | 36 |
| 250 | 59 |
| 300 | 93 |
| 350 | 37 |

While the present disclosure is primarily directed to the conversion of cyclohexanol to cyclohexanone, it should be understood that the features disclosed herein have application to the production of other ketones and cyclic ketones.

While this invention has been described as relative to exemplary designs, the present invention may be further modified within the spirit and scope of this disclosure. Further, this application is intended to cover such departures from the present disclosure as come within known or customary practice in the art to which this invention pertains.

What is claimed is:

1. A method of converting an alcohol to a ketone, comprising:
   reacting the alcohol in the presence of a catalyst and oxygen to produce the ketone, wherein the catalyst comprises a microporous copper chloropyrophosphate framework including a plurality of noble metal nanoparticles.

2. The method of claim 1, wherein the alcohol is a cyclic alcohol.

3. The method of claim 2, wherein the alcohol is cyclohexanol and the ketone is cyclohexanone.

4. The method of claim 3, further comprising providing a mixture of cyclohexanone and cyclohexanol, wherein the provided cyclohexanol is reacted in said reacting step.

5. The method of claim 4, wherein the mixture comprises 5 wt. % to 95 wt. % cyclohexanol, based on the total weight of the cyclohexanol and cyclohexanone.

6. The method of claim 4, wherein the mixture comprises 40 wt. % to 60 wt. % cyclohexanol, based on the total weight of the cyclohexanol and cyclohexanone.

7. The method of claim 1, wherein the noble metal nanoparticles include at least one metal selected from the group consisting of platinum, palladium, and gold.

8. The method of claim 1, wherein the noble metal nanoparticles include at least two metals selected from the group consisting of platinum, palladium, and gold.

9. A catalyst comprising a bimetallic microporous copper chloropyrophosphate framework including a plurality of platinum and gold noble metal nanoparticles, the microporous copper chloropyrophosphate framework having a general formula of $Rb_9Cu_6(P_2O_7)_4Cl_4(AuCl_4)Rb_9Cu_6(P_2O_7)_4Cl_3(PtCl_4)$.

10. The catalyst of claim 9, wherein the catalyst has been activated at a temperature of about 300° C.

11. A method of making a catalyst, the method comprising:
   mixing copper (II) fluoride, orthophosphoric acid, rubidium hydroxide, rubidium chloride, and at least one source of metal chloride;
   heating the mixture in a sealed container to form a catalyst precursor including precursor complexes; and
   activating the catalyst by heating the catalyst precursor at a temperature of at least 175° C. to converting the precursor complexes to noble metal nanoparticle sites.

12. The method of claim 11, wherein the source of metal chloride is selected from the group consisting of $K_2PtCl_4$, $K_2PdCl_4$, $HAuCl_4$, and $KAuCl_4$.

* * * * *